US009057048B2

United States Patent
Kitamura et al.

(10) Patent No.: US 9,057,048 B2
(45) Date of Patent: Jun. 16, 2015

(54) INFECTIOUS HEPATITIS C VIRUS—HIGH PRODUCING HCV VARIANTS AND USE THEREOF

(75) Inventors: Yoshihiro Kitamura, Tokyo (JP); Yoko Shimizu, Tokyo (JP); Chie Aoki, Hyogo (JP); Lijuan Yu, Beijing (CN); Takaji Wakita, Tokyo (JP)

(73) Assignees: THE UNIVERSITY OF TOKYO, Tokyo (JP); NIHON UNIVERSITY, Tokyo (JP); INSTITUTE OF MICROBIOLOGY, CHINESE ACADEMY OF SCIENCES, Beijing (CN); TORAY INDUSTRIES, INC., Tokyo (JP); JAPAN AS REPRESENTED BY DIRECTOR-GENERAL OF NATIONAL INSTITUTE OF INFECTIOUS DISEASES, Tokyo (JP); TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 274 days.

(21) Appl. No.: 13/636,904

(22) PCT Filed: Mar. 25, 2011

(86) PCT No.: PCT/JP2011/057271
§ 371 (c)(1),
(2), (4) Date: Dec. 13, 2012

(87) PCT Pub. No.: WO2011/118743
PCT Pub. Date: Sep. 29, 2011

(65) Prior Publication Data
US 2013/0078277 A1    Mar. 28, 2013

(30) Foreign Application Priority Data
Mar. 25, 2010    (CN) .......................... 2010 1 0139886

(51) Int. Cl.
| | |
|---|---|
| A61K 39/29 | (2006.01) |
| C12N 7/02 | (2006.01) |
| C12N 15/06 | (2006.01) |
| C12N 1/02 | (2006.01) |
| C12N 7/00 | (2006.01) |
| C07K 14/18 | (2006.01) |
| C07K 14/005 | (2006.01) |

(52) U.S. Cl.
CPC ........ *C12N 7/00* (2013.01); *C12N 2770/24222* (2013.01); *C12N 2770/24243* (2013.01); *C12N 2770/24251* (2013.01); *A61K 39/29* (2013.01); *C07K 14/1833* (2013.01); *C12N 2770/24221* (2013.01); *C07K 14/005* (2013.01)

(58) Field of Classification Search
CPC ............ A61K 39/29; A61K 2039/525; A61K 2039/5258
See application file for complete search history.

(56) References Cited

FOREIGN PATENT DOCUMENTS

| | | |
|---|---|---|
| CN | 101748149 B | 9/2012 |
| WO | WO 2008/022401 A1 | 2/2008 |
| WO | WO 2010/017818 A1 | 2/2010 |

OTHER PUBLICATIONS

Rollier et al. Control of Heterologous Hepatitis C Virus Infection in Chimpanzees is Associated with the Quality of Vaccine-Induced Peripheral T-Helper Immune Response. J Virol. 2004, 78(1): 187-196.*
Shirai et al. An Epitope in Hepatitis C Virus Core Region Recognized by Cytotoxic T Cells in Mice and Humans. J Virol, 1994, 68(5): 3334-3342.*
Huang et al. Recent development of therapeutics for chronic HCV infection. Antiviral Res 71 (2006) 351-362.*
Tan et al. Strategies for hepatitis C therapeutic intervention: now and next. Curr Opin in Pharmacology, 2004, 4: 465-470.*
Racanelli et al. Presentation of HCV antigens to naive CD8+T cells: why the where, when, what and how are important for virus control and infection outcome. Clin Immunol. Jul. 2007;124(1):5-12.*
Koziel et al. Hepatitis C virus (HCV)-specific cytotoxic T lymphocytes recognize epitopes in the core and envelope proteins of HCV. J Virol. Dec. 1993;67(12):7522-32.*
Berzofsky et al. Progress on new vaccine strategies against chronic viral infections. J Clin Invest. Aug. 2004;114(4):450-62.*
Search Report dated Jan. 8, 2014 for European Application No. 11 75 9547.
Japanese Office Action cited in Japanese Patent Application No. 2012-507076 on Jan. 27, 2015.
Akuta et al., "Analysis of Hepatitis C virus factors determining therapeutic effect of PEG-interferon/Ribavirin combination therapy," Okinaka Memorial Institute for Medical Research Annual Report, No. 35, 2009, pp. 33-35.
Angus et al., "Requirement of cellular DDX3 for hepatitis C virus replication is unrelated to its interaction with the viral core protein," Journal of General Virology, vol. 91, 2010, pp. 122-132.
International Search Report issued in PCT/JP2011/057271, mailed on May 10, 2011.
Kaul et al., "Cell Culture Adaptation of Hepatitis C Virus and in Vivo Viability of an Adapted Variant," Journal of Virology, vol. 81, No. 23, Dec. 2007, pp. 13168-13179.
Kobayashi et al., "Influence of Amino-Acid Polymorphism in the Core Protein on Progression of Liver Disease in Patients Infected With Hepatitis C Virus Genotype 1b," Journal of Medical Virology, vol. 82, 2010, pp. 41-48.
Mateu et al., "Intragenotypic JFH1 based recombinant hepatitis C virus produces high levels of infectious particles but causes increased cell death," Virology, vol. 376, 2008, pp. 397-407.

(Continued)

*Primary Examiner* — Michelle S Horning
(74) *Attorney, Agent, or Firm* — Birch, Stewart, Kolasch & Birch, LLP

(57) ABSTRACT

An objective of this invention is to provide an HCV strain with a high capacity for virus production in a cell culture system. This invention provides a nucleic acid encoding a polyprotein precursor of the hepatitis C virus JFH1 strain having one or more amino acid substitutions, wherein the polyprotein precursor comprises at least substitution of glutamine at position 862 with arginine, as determined with reference to the amino acid sequence as shown in SEQ ID NO: 2 in the Sequence Listing.

10 Claims, 18 Drawing Sheets
(1 of 18 Drawing Sheet(s) Filed in Color)

(56) References Cited

OTHER PUBLICATIONS

Mishima et al., "Cell culture and in vivo analyses of cytopathic hepatitis C virus mutants," Virology, vol. 405, 2010, pp. 361-369.

Wakita et al., "Construction of infectious hepatitis C virus strain and library of sensitive cultured cells," Research Report of Political General Research of Drug Discovery, The Japan Health Sciences Foundation, 2008, pp. 181-191.

Wakita et al., "Production of infectious hepatitis C virus in tissue culture from a cloned viral genome," Nature Medicine, vol. 11, No. 7, Jul. 2005, pp. 791-796.

Written Opinion of the International Searching Authority issued in PCT/JP2011/057271, mailed on May 10, 2011.

* cited by examiner

Fig. 4

| Clone No. | Core | E1 | E2 | p7 | NS2 | NS3 |
|---|---|---|---|---|---|---|
| 5-2 | K74T* | Y297H* A330T* | S395P* N417S* D483G A501T | | Q862R* Q931R* S961A* | A1411V |
| 5-4 | V31A* K74T* | | G451R* | V756A V786A | Q862R* | |
| 5-5 | K74T* | P241S Y297H* A330T* | S395P* N417S* L541P | | Q862R* L905P S961A* | |
| 5-7 | G28C K74T* | Y297H* A330T* | S395P* N417S* | | Q862R* | |
| 5-8 | N14S K74T* | C226R Q296R Y297H* A330T* | S395P* N417S* T597A I700S | | Q862R* S961A* | |
| 5-9 | R9K V31A* S71P K74T* | | G451R* | V757A | Q862R* I883T | R1393K |

* Amino acid mutation observed in two or more of six clones

Fig. 6
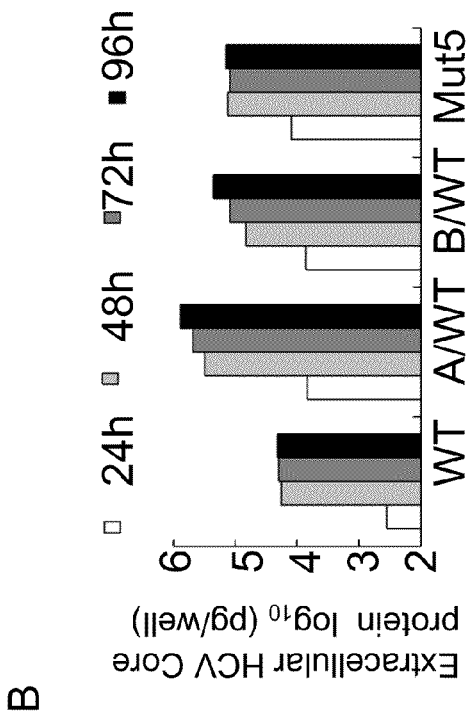
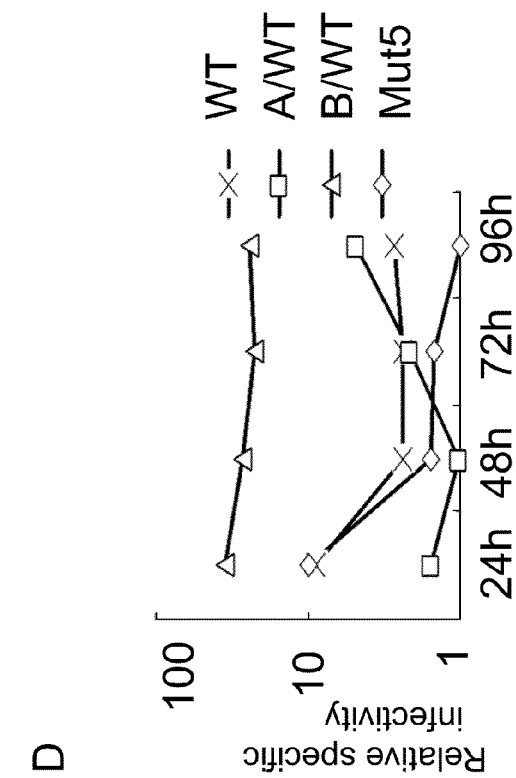
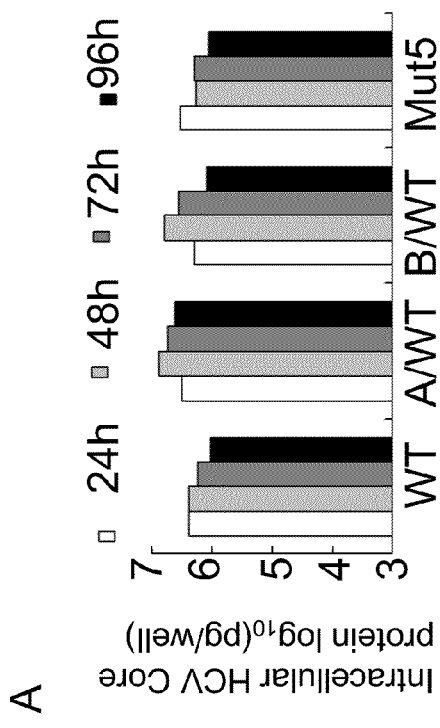
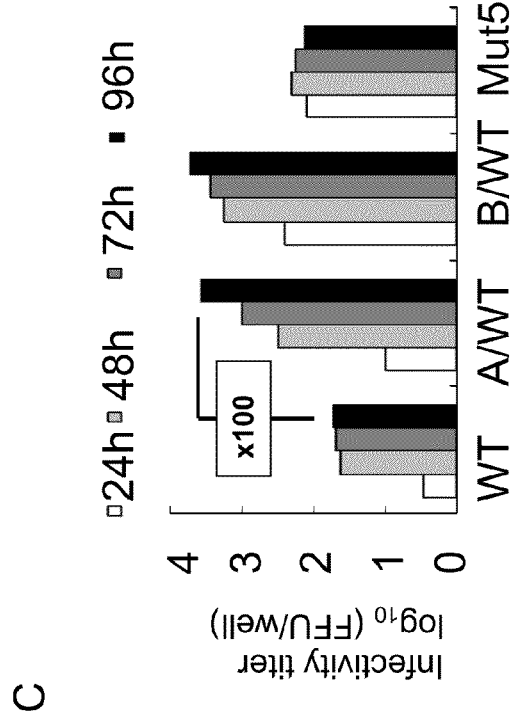

Fig. 10

| | | | | | | | | | | |
|---|---|---|---|---|---|---|---|---|---|---|
| 5' | C | E1 | E2 | | 2 | 3 | 4A | 4B | 5A | 5B | 3' | 31+(V31A) |
| 5' | C | E1 | E2 | | 2 | 3 | 4A | 4B | 5A | 5B | 3' | 74+(K74T) |
| 5' | C | E1 | E2 | | 2 | 3 | 4A | 4B | 5A | 5B | 3' | 451+(G451R) |
| 5' | C | E1 | E2 | | 2 | 3 | 4A | 4B | 5A | 5B | 3' | 756+(V756A) |
| 5' | C | E1 | E2 | | 2 | 3 | 4A | 4B | 5A | 5B | 3' | 786+(V786A) |
| 5' | C | E1 | E2 | p7 | 2 | 3 | 4A | 4B | 5A | 5B | 3' | 862+(Q862R) |

Fig. 16

INFECTIOUS HEPATITIS C VIRUS—HIGH PRODUCING HCV VARIANTS AND USE THEREOF

TECHNICAL FIELD

The present invention relates to a hepatitis C virus (HCV) variant with a high capacity for production of infectious HCV, a genomic nucleic acid thereof, and a cell into which the genomic nucleic acid has been introduced. In addition, the present invention relates to a method for producing infectious HCV particles and a method for screening for an anti-HCV agent.

BACKGROUND ART

The hepatitis C virus (HCV) was discovered and identified as the causative virus of non-A, non-B hepatitis by Choo et al. in 1989 (Non-Patent Document 1). HCV infection causes chronic hepatitis, and the chronic hepatitis progresses to cirrhosis with persistent HCV infection, and then to liver cancer. It is said that approximately 170,000,000 patients are infected with HCV in the whole world, and approximately 2,000,000 patients are infected therewith in Japan. HCV is mainly transmitted through blood. Although the number of patients newly infected with HCV was sharply reduced since screening of blood for transfusion was made possible, it is considered that a large number of virus carriers still exists.

At present, treatment of chronic hepatitis C is mainly carried out via administration of pegylated interferon or combination therapy with pegylated interferon and the anti-virus agent ribavirin. Up to the present, HCV has been classified into 6 different genotypes. Infection with HCV genotypes 1b and 2a are major cases in Japan. In particular, viruses of HCV of genotype 1b cannot be completely removed from the body by the administration of interferon in combination with ribavirin, and the therapeutic effects are not satisfactory (Non-Patent Documents 2 and 3). Accordingly, development of novel anti-viral agents or vaccines aimed at the prevention of development of hepatitis C or the elimination of HCV viruses has been awaited.

Virus vaccines are classified based on antigens; that is, component vaccines using viral proteins as antigens; vaccines using virus particles as antigens; and DNA vaccines using viral protein-encoding genes. Vaccines using virus particles as antigens are classified as attenuated live vaccines or inactivated vaccines. When vaccines using virus particles as antigens are produced, a system for producing highly purified virus particles is necessary, and such system requires a culture system for producing large quantities of virus particles.

The hepatitis C virus (HCV) comprises a plus single-stranded RNA genome of approximately 9.6 kb. The HCV single-stranded RNA genome encodes a single polyprotein (i.e., a polyprotein precursor) containing 10 types of proteins (i.e., Core, E1, E2, p7, NS2, NS3, NS4A, NS4B, NS5A, and NS5B proteins). A polyprotein precursor translated from the HCV RNA genome is cleaved into individual proteins, so as to serve as viral proteins.

A replicon system that allows autonomous replication of HCV RNA in a cell culture system has been developed and employed in many studies regarding HCV. A typical subgenomic replicon is prepared by substituting a structural protein region of HCV genome with a marker gene, such as a drug resistance gene, and inserting IRES from encephalomyocarditis virus (EMCV) into a site downstream thereof. Replication of HCV RNA is observed in cultured cells into which the subgenomic replicon RNA has been introduced (Patent Document 1). Studies on the replication of HCV subgenomic replicon show that genetic mutations of the HCV genome may exhibit the effect to enhance the replication efficiency of replicon, and such genetic mutations are referred to as adaptive mutations (Patent Document 1).

NK5.1 strain (Con1/NK5.1), which is a variant of the subgenomic replicon pFK-I389neo/NS3-39/wt (Con1/wt) derived from the Con1 strain of genotype 1b and has an adaptive mutation in the NS3-NS5A region, is reported to have proliferative capacity approximately 10 times higher than that of the wild-type Con1/wt strain (Non-Patent Document 4). Meanwhile, the literature describing the results of sequence analysis of replicons in replicon-replicating cells having subgenomic replicons derived from the HCV JFH1 strain of genotype 2a isolated from a patient with fulminant hepatitis (Non-Patent Document 5) discloses that several mutations were observed in the HCV genome-derived regions in 5 out of 6 resulting clones, but no common mutations were observed among them. In addition, the literature discloses that a nucleotide mutation in the other one clone would not cause amino acid mutation. This indicates that the JFH1 strain is capable of proliferating in Huh7 cells without adaptive mutations.

Regarding HCV production in a cell culture system, Wakita et al. showed that infectious HCV particles were successfully produced via introduction of the full-length HCV genomic replicon derived from the JFH1 strain into Huh7 cells (Patent Document 2 and Non-Patent Document 6). Also, Kaul et al. reported that the mutations in the NS5A protein of the JFH1 strain resulted in the production of viruses in amounts approximately 10 times higher than that of the wild-type JFH1 strain (Non-Patent Document 7).

It is reported that the capacity of the JFH1 strain for virus particle production in a cell culture system is $4.6 \times 10^4$ FFU/ml (Non-Patent Document 8), which is much lower than the capacity of influenza virus for virus particle production in a cell culture system, i.e., about $4 \times 10^9$ PFU/ml (Non-Patent Document 9). Production of vaccines using HCV particles as antigens requires the development of HCV strains with a higher capacity for virus particle production.

REFERENCES

Patent Documents

Patent Document 1: International Publication WO 2004/104198
Patent Document 2: International Publication WO 2005/080575

Non-Patent Documents

Non-Patent Document 1: Choo et al., Science, 1989, 244 (4902), pp. 359-362
Non-Patent Document 2: Fried et al., N. Engl. J. Med., 2002, Vol. 347, No. 13, pp. 975-982
Non-Patent Document 3: Lusida et al., J. Clin. Microbiol., 2001, 39 (11), pp. 3858-3864
Non-Patent Document 4: Krieger et al., J. Virol., 2001, 70: 4614-4624
Non-Patent Document 5: Kato et al., Gastroenterology, 2003, 125: 1808-1817
Non-Patent Document 6: Wakita et al., Nat. Med., 2005, 11 (7), pp. 791-796
Non-Patent Document 7: Kaul et al., J. Virol., 2007, 81 (23), pp. 13168-13179

Non-Patent Document 8: Zhong et al., Proc. Natl. Acad. Sci. U.S.A., 2005, 102 (26), pp. 9294-9299

Non-Patent Document 9: Tree et al., Vaccine, 2001, 19 (25-26), pp. 3444-3450

SUMMARY OF THE INVENTION

Problem to be Solved by the Invention

An objective of the present invention is to provide an HCV strain with a high capacity for virus production in a cell culture system.

Means for Solving the Problem

The present inventors have conducted concentrated studies in order to solve the above objective, and then they found that some amino acid mutations would significantly increase the virus production capacity of the JFH1 strain. This has led to the completion of the present invention.

Specifically, the present invention includes the following.

[1] A nucleic acid comprising a sequence encoding a polyprotein precursor of the hepatitis C virus JFH1 strain having one or more amino acid substitutions, wherein the polyprotein precursor comprises at least substitution of glutamine at position 862 with arginine, as determined with reference to the amino acid sequence as shown in SEQ ID NO: 2 in the Sequence Listing.

In a preferred embodiment, this nucleic acid may comprise the 5'-untranslated region and the 3'-untranslated region of the genome of the hepatitis C virus JFH1 strain.

[2] The nucleic acid according to [1] above, wherein the polyprotein precursor is selected from the group consisting of (a) to (f):

(a) a polyprotein precursor having substitutions of lysine at position 74 with threonine, tyrosine at position 297 with histidine, alanine at position 330 with threonine, serine at position 395 with proline, asparagine at position 417 with serine, aspartic acid at position 483 with glycine, alanine at position 501 with threonine, glutamine at position 862 with arginine, glutamine at position 931 with arginine, and serine at position 961 with alanine, as determined with reference to the amino acid sequence as shown in SEQ ID NO: 2 in the Sequence Listing;

(b) a polyprotein precursor having substitutions of valine at position 31 with alanine, lysine at position 74 with threonine, glycine at position 451 with arginine, valine at position 756 with alanine, valine at position 786 with alanine, and glutamine at position 862 with arginine, as determined with reference to the amino acid sequence as shown in SEQ ID NO: 2 in the Sequence Listing;

(c) a polyprotein precursor having substitutions of lysine at position 74 with threonine, glycine at position 451 with arginine, valine at position 756 with alanine, valine at position 786 with alanine, and glutamine at position 862 with arginine, as determined with reference to the amino acid sequence as shown in SEQ ID NO: 2 in the Sequence Listing;

(d) a polyprotein precursor having substitutions of valine at position 31 with alanine, lysine at position 74 with threonine, glycine at position 451 with arginine, valine at position 786 with alanine, and glutamine at position 862 with arginine, as determined with reference to the amino acid sequence as shown in SEQ ID NO: 2 in the Sequence Listing;

(e) a polyprotein precursor having substitutions of valine at position 31 with alanine, lysine at position 74 with threonine, glycine at position 451 with arginine, valine at position 756 with alanine, and glutamine at position 862 with arginine, as determined with reference to the amino acid sequence as shown in SEQ ID NO: 2 in the Sequence Listing; and (f) a polyprotein precursor having only one substitution of glutamine at position 862 with arginine, as determined with reference to the amino acid sequence as shown in SEQ ID NO: 2 in the Sequence Listing.

[3] The nucleic acid according to [2] above, which consists of the nucleotide sequence as shown in SEQ ID NO: 3, 4, or 5 in the Sequence Listing.

[4] The nucleic acid according to [1] or [2] above, wherein a nucleic acid encoding a reporter protein is inserted into a region encoding the NS5A protein in the polyprotein precursor.

[5] The nucleic acid according to [4] above, wherein the reporter protein is incorporated into the sequence of amino acids at positions 2394 to 2397 of the amino acid sequence as shown in SEQ ID NO: 2 in the Sequence Listing to be translated as a fusion protein.

[6] The nucleic acid according to [5] above, which consists of the nucleotide sequence as shown in SEQ ID NO: 6 or 7 in the Sequence Listing.

[7] A hepatitis C virus particle which contains the nucleic acid according to [1] to [3] above.

[8] A cultured cell which produces the hepatitis C virus particle according to [7] above.

[9] A hepatitis C virus vaccine obtained by inactivating the hepatitis C virus particle according to [7] above.

The present invention also includes the following.

[10] A hepatitis C virus particle which contains the nucleic acid according to [4] to [6] above.

[11] A cultured cell which produces the hepatitis C virus particle according to [10] above.

[12] A vector comprising the nucleic acid according to any of [1] to [6] above.

[13] A method for screening for an anti-hepatitis C virus substance comprising the steps of:

culturing the cultured cell producing a hepatitis C virus particle containing the nucleic acid according to [4] or [6] above, in the presence of a test substance; and detecting the reporter protein in the resulting culture, wherein if an expression level of the reporter protein is lower, the test substance is determined to have an anti-hepatitis C virus activity.

[14] An anti-hepatitis C virus antibody which recognizes the hepatitis C virus particle according to [7] above as an antigen.

Effects of the Invention

The present invention provides a strain with a high capacity for production of infectious HCV particles. With the use of such strain with a high capacity for production of infectious HCV particles, a high-level HCV-producing system can be provided.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 3 shows a comparison of properties of JFH1a and wild-type JFH1wt. The vertical axis represents relative replication rate (%) compared to the control sample without IFN-α added. A open circle represents the data of JFH1wt and a filled square represents the data of JFH1a.

FIG. 4 shows amino acid mutations from wild-type JFH1wt, found by sequence analysis of six clones of JFH1a. In FIG. 4, amino acid mutations observed in 2 or more out of 6 clones are denoted with an asterisk.

FIG. 6 shows the results of a comparison of infectivity of the wild-type JFH1wt strain and variants thereof "WT" denotes JFH1wt, "A/WT" denotes JFH1-A/WT, "B/WT" denotes JFH1-B/WT, and "Mut5" denotes JFH1-mut5. The same applies to the other parts of the description and the drawings of the present application. FIG. 6A shows a comparison of the amounts of intracellular Core protein after transfection, FIG. 6B shows a comparison of the amounts of Core proteins released into a culture supernatant; FIG. 6C shows a comparison of infectivity titers of culture supernatants, and FIG. 6D shows a comparison of specific activities (relative specific infectivity; specific activity=[infectivity titer of culture supernatant]/[amounts of Core proteins in culture supernatant]). Bar graphs in A to C each show, from left to right, data after 24 hours (24 h), 48 hours (48 h), 72 hours (72 h), and 96 hours (96 h).

FIG. 8A shows JFH1-A/WT, FIG. 8B shows JFH1-B/WT, FIG. 8C shows JFH1a, FIG. 8D shows JFH1-Mut5, and FIG. 8E shows JFH1wt.

FIG. 10 shows structure diagrams of the full-length HCV genomes (i.e., the polyprotein precursor coding regions and the untranslated regions) of 6 types of variants in which each one out of 6 amino acid mutations in JFH1-B/WT is introduced into the wild-type JFH1wt. A star indicates a site into which an amino acid mutation from the JFH1-B/WT has been introduced.

FIG. 11A shows infectivity titers of culture supernatants of the variants, indicating the level of extracellular release of infectious virus particles. FIG. 11B shows the amounts of extracellular Core proteins released by the variants into culture supernatants. FIG. 11C shows the specific activity (relative specific infectivity; specific activity=[infectivity titer of culture supernatant]/[amounts of Core proteins in culture supernatant]), the value being expressed relative to the specific activity of WT (=1). 31-, 74-, 451-, 756-, 786-, 862-, 451+, WT, and B/WT denote 31-(A31V), 74-(T74K), 451-(R451G), 756-(A756V), 786-(A786V), 862-(R862Q), 451+ (G451R), JFH1wt, and JFH1-B/WT, respectively. The same applies to the other parts of the description and the drawings of the present application.

FIG. 12A shows infectivity titers of culture supernatants of the mutants, indicating the level of extracellular release of infectious virus particles. FIG. 12B shows the amounts of extracellular Core proteins released by the variants into culture supernatants. FIG. 12C shows the specific activity (relative specific infectivity; specific activity=[infectivity titer of culture supernatant]/[amounts of Core proteins in culture supernatant]). The value is written relative to the specific activity of WT (=1). 31+, 74+, 451+, 756+, 786+, 862+, WT, and B/WT denote 31+(V31A), 74+(K74T), 451+(G451R), 756+ (V756A), 786+(V786A), 862+(Q862R), JFH1wt, and JFH1-B/WT, respectively. The same applies to the other parts of the description and the drawings of the present application.

FIG. 13A shows the amounts of extracellular Core proteins in culture supernatants of the variants. FIG. 13B shows the infectivity titers of culture supernatants of the variants.

FIG. 14A shows the amounts of extracellular Core proteins in culture supernatants of the variants. FIG. 14B shows the infectivity titers of culture supernatants of the variants.

FIG. 16 shows the infectivity titer of culture supernatants of wild-type JFH1wt-Rluc, and variants JFH1-A/WT-Rluc and JFH1-B/WT-Rluc, into which the reporter gene has been incorporated. In the figure, WT denotes JFH1wt, and WT-Rluc, A/WT-Rluc, and B/WT-Rluc denote JFH1wt-Rluc, JFH1-A/WT-Rluc, and JFH1-B/WT-Rluc resulting from incorporation of the Rluc gene into JFH1wt, JFH1-A/WT, and JFH1-B/WT, respectively. The same applies to FIG. 18.

17B) at 100 FFU, 50 FFU, 25 FFU, 12 FFU, 6 FFU, 3 FFU, and 0 FFU, which demonstrate that luciferase activity was detected depending on the amounts of viruses.

Figure 18:
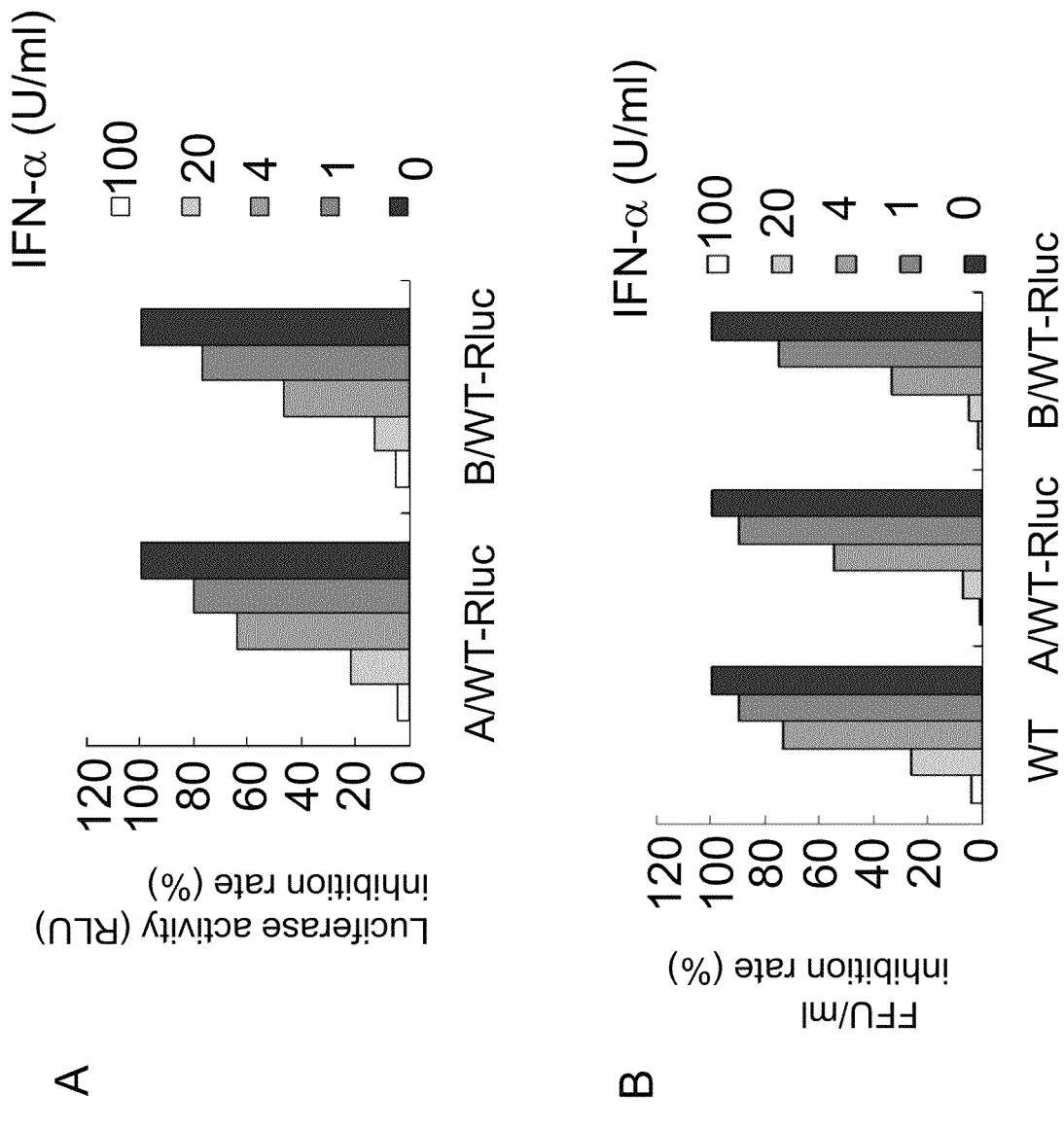

FIG. 18 shows the test results of the anti-HCV activity of interferon (IFN) using an infection/replication system in cultured cells with JFH1-A/WT-Rluc and JFH1-B/WT-Rluc viruses. The vertical axis in FIG. 18A indicates the inhibition rate (%) relative to the luciferase activity without IFN-α added (=100%). The vertical axis in FIG. 18B indicates the infection inhibition rate (%) relative to the infection titer without IFN-α added (=100%). Doses of IFN-α (in concentrations) are 100 U/ml (white bar), and 20, 4, 1, and 0 U/ml from left to right. FIG. 18A shows the inhibition rate of luciferase activity (RLU) in the presence of interferon as determined by luciferase assay. FIG. 18B shows the inhibition rate of infection titer (FFU/ml) in the presence of interferon.

EMBODIMENTS FOR CARRYING OUT THE INVENTION

The present inventors had carried out a prolonged culture in a full-length HCV replicon replication system with the JFH1 strain for 2 years, screened such cultured cells for adapted variants with improved virus particle multiplication capacity, and then found strains with high capacity for production of JFH1 viruses. Further, they prepared highly infectious virus particles having a full-length HCV genome that expresses a reporter gene. This has led to the completion of the present invention.

The present invention relates to a highly productive HCV JFH1 variant that may be isolated from Huh7 cells which comprise the full-length HCV genome sequence, continuously replicates the full-length genome sequence, and produce infectious virus particles.

The present invention can be implemented using conventional molecular biology and virology techniques within the scope of the relevant technical field. Such techniques are thoroughly described in literatures, such as Sambrook et al., Molecular Cloning: A Laboratory Manual, Cold Spring Harbor Laboratory, vol. 3, 2001 or Mahy et al., Virology: A Practical Approach, 1985, IRL PRESS.

All publications, patents, and patent applications cited herein are incorporated herein by reference in their entirety.
(1) Variant Nucleic Acids Derived from HCV JFH1 Genome Sequence The present invention relates to a nucleic acid comprising a genome sequence of a virus variant of HCV JFH1 comprising an adaptive mutation in its genome that significantly increases the capacity to produce virus particles. The nucleic acid according to the present invention preferably comprises a full-length HCV genome sequence.

Specifically, the nucleic acid according to the present invention comprises a sequence encoding a polyprotein precursor comprising an amino acid mutation in the polyprotein precursor of the hepatitis C virus JFH1 strain (preferably, the polyprotein precursor consisting of the amino acid sequence as shown in SEQ ID NO: 2). More specifically, the nucleic acid comprises a sequence encoding a polyprotein precursor of the hepatitis C virus JFH1 strain comprising one or more amino acid substitutions in a region spanning from Core to NS2 of the polyprotein precursor.

A polyprotein precursor encoded by the nucleic acid according to the present invention comprises HCV structural and non-structural proteins. HCV structural proteins are Core, E1, E2, and p7 proteins, which constitute the HCV virus particles. "Core" is a core protein, "E1" and "E2" are envelope proteins, and "p7" is a protein forming an ion channel that functions on cellular membranes of host cells. HCV non-structural proteins are NS2, NS3, NS4A, NS4B, NS5A, and NS5B, which are enzyme proteins having activities involved in virus genome replication or HCV protein processing. While various HCV genotypes are known, it is known that HCV genomes of various genotypes have similar gene structures (see, for example, FIG. 1). A polyprotein precursor encoded by the nucleic acid according to the present invention preferably comprises Core, E1, E2, p'7, NS2, NS3, NS4A, NS4B, NS5A, and NS5B protein regions in that order from the N terminus to the C terminus. A polyprotein precursor encoded by the nucleic acid according to the present invention may further comprise a foreign protein, such as a selection marker protein or reporter protein.

The full-length genome sequence in the nucleic acid according to the present invention comprises a 5'-untranslated region at the 5' end, a polyprotein precursor-coding region at the 3' side of the 5'-untranslated region, and a 3'-untranslated region at the 3' side of the polyprotein precursor-coding region and at the 3' end. The full-length genome sequence may consist of the 5'-untranslated region, the Core protein coding sequence, the E1 protein coding sequence, the E2 protein coding sequence, the p7 protein coding sequence, the NS2 protein coding sequence, the NS3 protein coding sequence, the NS4A protein coding sequence, the NS4B protein coding sequence, the NS5A protein coding sequence, the NS5B protein coding sequence, and the 3'-untranslated region, in that order in the 5' side to 3' side.

The HCV 5'-untranslated region (also referred to as "5' UTR" or "5' NTR") is a region of N terminal about 340 nucleotides of the full-length HCV genome, which provides an internal ribosome recognition site (IRES) for protein translation and an element necessary for replication.

The HCV 3'-untranslated region (also referred to as "3' UTR" or "3' NTR") has a function of assisting HCV replication, and it comprises an additional region of about 100 nucleotides in addition to a poly U region.

In the present invention, the term "replicon RNA" refers to RNA having the capacity for self-replication (autonomous replication) within a cell. Replicon RNA introduced into a cell self-replicates, and RNA copies thereof are divided to daughter cells during cell division. With the use of replicon RNA, accordingly, foreign genes can be stably introduced into a cell. The nucleic acid according to the present invention is a replicon RNA if it is RNA consists of the full-length genome sequence (full-length genomic RNA) containing the 5'-untranslated region at the 5' end, a polyprotein precursor-coding region at the 3' side of the 5'-untranslated region, and the 3'-untranslated region at the 3' side of and the polyprotein precursor-coding region at the 3' end.

In the present invention, a "nucleic acid" encompasses RNA and DNA. The term "protein coding region" or "sequence encoding a protein" used herein refers to a nucleotide sequence that encodes an amino acid sequence of a given protein and that may or may not comprise an initiation codon and a termination codon. The "polyprotein precursor coding region" and the "sequence encoding a polyprotein precursor" should be understood in the same manner.

When a nucleotide sequence or nucleotide of RNA that is a nucleic acid according to the present invention is specified herein with a SEQ ID NO: in the Sequence Listing, T (thymine) in the nucleotide sequence as shown in the SEQ ID NO: shall be deemed to be replaced with U (uracil).

In the present description, the expression "an amino acid at position 'Y' as determined with reference to the amino acid sequence as shown in SEQ ID NO: 2 in the Sequence Listing"

refers to an amino acid residue located at the "Y$^{th}$" position counted from the first amino acid (methionine) at the N terminus in the amino acid sequence as shown in SEQ ID NO: 2, or an amino acid corresponding to the amino acid residue located at the "Y$^{th}$" position of SEQ ID NO: 2 in another amino acid sequence aligned with the sequence of SEQ ID NO: 2.

In the present invention, the hepatitis C virus JFH1 strain is an HCV strain of genotype 2a isolated from a patient with fulminant hepatitis by Wakita et al. (e.g., see, WO 2005/080575). HCV "genotypes" used herein mean those determined in accordance with the international classification designated by Simmonds et al. An amino acid sequence of a polyprotein precursor of the hepatitis C virus JFH1 strain is preferably the sequence (SEQ ID NO: 2) encoded by the full-length genome sequence disclosed under the GenBank Accession No. AB047639. The full-length genome sequence of the JFH1 strain is preferably the nucleotide sequence (SEQ ID NO: 1) disclosed under the GenBank Accession No. AB047639.

According to a preferred embodiment, the nucleic acid according to the present invention comprises a sequence encoding a polyprotein precursor of the hepatitis C virus JFH1 strain having one or more amino acid substitutions, wherein the one or more amino acid substitutions comprises a substitution of glutamine at position 862 as determined with reference to the amino acid sequence as shown in SEQ ID NO: 2 in the Sequence Listing with at least one arginine. Specifically, the nucleic acid according to the present invention is preferably a nucleic acid comprising a sequence encoding a polyprotein precursor of the hepatitis C virus JFH1 strain having one or more amino acid substitutions, wherein glutamine at position 862 of the polyprotein precursor, as determined with reference to the amino acid sequence as shown in SEQ ID NO: 2 in the Sequence Listing, has been preferably substituted with arginine. It is more preferred that the nucleic acid comprise the 5'-untranslated region at the 5' end, a polyprotein precursor-coding region at the 3' side of the 5'-untranslated region, and the 3'-untranslated region at the 3' side of and the polyprotein precursor-coding region and at the 3' end. The polyprotein precursor-coding sequence may further comprise a nucleotide sequence encoding a foreign protein, such as a selection marker protein or reporter protein.

One or more amino acid substitutions introduced into the polyprotein precursor comprise at least substitution of glutamine at position 862 with arginine (Q862R). It is also preferred that one or more amino acid substitutions introduced into the polyprotein precursor further comprise one or more of amino acid substitutions of the following (1) to (13):

(1) substitution of valine at position 31 with alanine (V31A);
(2) substitution of lysine at position 74 with threonine (K74T);
(3) substitution of tyrosine at position 297 with histidine (Y297H);
(4) substitution of alanine at position 330 with threonine (A330T);
(5) substitution of serine at position 395 with proline (5395P);
(6) substitution of asparagine at position 417 with serine (N4175);
(7) substitution of glycine at position 451 with arginine (G451R);
(8) substitution of aspartic acid at position 483 with glycine (D483G);
(9) substitution of alanine at position 501 with threonine (A501 T);
(10) substitution of valine at position 756 with alanine (V756A);
(11) substitution of valine at position 786 with alanine (V786A);
(12) substitution of glutamine at position 931 with arginine (Q931R); and
(13) substitution of serine at position 961 with alanine (S961A).

In the present description, for example, "amino acid mutation Q862R" refers to a mutation that is a substitution of amino acid residue Q (glutamine) at position 862 with R (arginine). Notation for other amino acid mutations is understood in the same manner. Amino acids are indicated herein with one-letter notation that is commonly used in the field of biology (Sambrook et al., Molecular Cloning: A Laboratory Manual Second Edition, 1989).

In the present description, amino acids or amino acid residues are indicated with one-letter or three-letter notation commonly used in the field of biology. The indicated amino acids also include amino acids subjected to post-translational modifications such as hydroxylation, glycosylation, or sulfation.

With the use of the nucleic acid according to the present invention, replicon RNA capable of producing JFH1 variant viruses with significantly improved capacity for virus particle production can be produced.

A preferred example of the nucleic acid according to the present invention is a nucleic acid comprising a sequence encoding a polyprotein precursor resulting from substitutions of lysine at position 74 with threonine, tyrosine at position 297 with histidine, alanine at position 330 with threonine, serine at position 395 with proline, asparagine at position 417 with serine, aspartic acid at position 483 with glycine, alanine at position 501 with threonine, glutamine at position 862 with arginine, glutamine at position 931 with arginine, and serine at position 961 with alanine, as determined with reference to the amino acid sequence as shown in SEQ ID NO: 2, in the amino acid sequence of the polyprotein precursor of the hepatitis C virus JFH1 strain (preferably, the amino acid sequence as shown in SEQ ID NO: 2). SEQ ID NO: 3 shows a preferred example of such nucleic acid.

Another preferred example of the nucleic acid according to the present invention is a nucleic acid comprising a sequence encoding a polyprotein precursor resulting from substitutions of valine at position 31 with alanine, lysine at position 74 with threonine, glycine at position 451 with arginine, valine at position 756 with alanine, valine at position 786 with alanine, and glutamine at position 862 with arginine, as determined with reference to the amino acid sequence as shown in SEQ ID NO: 2, in the amino acid sequence of the polyprotein precursor of the hepatitis C virus JFH1 strain (preferably, the amino acid sequence as shown in SEQ ID NO: 2). SEQ ID NO: 4 shows a preferred example of such nucleic acid.

Another preferred example of the nucleic acid according to the present invention is a nucleic acid comprising a sequence encoding a polyprotein precursor resulting from substitution of glutamine at position 862 with arginine, as determined with reference to the amino acid sequence as shown in SEQ ID NO: 2, in the amino acid sequence of the polyprotein precursor of the hepatitis C virus JFH1 strain (and preferably, the amino acid sequence as shown in SEQ ID NO: 2). SEQ ID NO: 5 shows a preferred example of such nucleic acid.

Another preferred example of the nucleic acid according to the present invention is a nucleic acid comprising a sequence encoding a polyprotein precursor resulting from substitutions of lysine at position 74 with threonine, glycine at position 451 with arginine, valine at position 756 with alanine, valine at position 786 with alanine, and glutamine at position 862 with arginine, as determined with reference to the amino acid sequence as shown in SEQ ID NO: 2, in the amino acid sequence of a polyprotein precursor of the hepatitis C virus JFH1 strain (and preferably, the amino acid sequence as shown in SEQ ID NO: 2).

Another preferred example of the nucleic acid according to the present invention is a nucleic acid comprising a sequence encoding a polyprotein precursor resulting from substitutions of valine at position 31 with alanine, lysine at position 74 with threonine, glycine at position 451 with arginine, valine at position 786 with alanine, and glutamine at position 862 with arginine, as determined with reference to the amino acid sequence as shown in SEQ ID NO: 2, in the amino acid sequence of a polyprotein precursor of the hepatitis C virus JFH1 strain (and preferably, the amino acid sequence as shown in SEQ ID NO: 2).

Another preferred example of the nucleic acid according to the present invention is a nucleic acid comprising a sequence encoding a polyprotein precursor resulting from substitutions of valine at position 31 with alanine, lysine at position 74 with threonine, glycine at position 451 with arginine, valine at position 756 with alanine, and glutamine at position 862 with arginine, as determined with reference to the amino acid sequence as shown in SEQ ID NO: 2, in the amino acid sequence of a polyprotein precursor of the hepatitis C virus JFH1 strain (and preferably, the amino acid sequence as shown in SEQ ID NO: 2).

In order to function as replicon RNA, it is more preferred that these nucleic acids comprise a 5'-untranslated region at the 5' end, a polyprotein precursor-coding region at the 3' side of the 5'-untranslated region, and a 3'-untranslated region at the 3' side of the polyprotein precursor-coding region and at the 3' end.

Replicon RNA, which is the nucleic acid according to the present invention as described above, replicon RNA prepared from the nucleic acid, or in particular, full-length genome replicon RNA (full-length genomic HCV RNA) has a significantly increased capacity for virus production compared with replicon RNA of the wild-type JFH1 strain. The term "the capacity for virus production" (or "the capacity to produce viruses") used herein refers to the capacity to produce virus particles (and preferably, the capacity to produce infectious virus particles) preferably in a cell culture system. The nucleic acid according to the present invention or replicon RNA prepared from the nucleic acid has a capacity for virus production that is twice or more as high, preferably 10 times or more as high, and typically 10 to 10,000 times or more as high (e.g., 10 to 1,000 times or more as high) as that of full-length genome replicon RNA of the wild-type JFH1 strain, for example. Also, full-length genome replicon RNA, which is the nucleic acid according to the present invention, has the capacity for virus production that is twice or more as high, and preferably 10 times or more as high as that of full-length genome replicon RNA derived from the JFH1 strain encoding a polyprotein precursor in which valine at position 2440 of the amino acid sequence as shown in SEQ ID NO: 2 has been substituted with leucine. SEQ ID NO: 1 shows the full-length genome sequence of the wild-type JFH1 strain. The sequence as shown in SEQ ID NO: 2 is an amino acid sequence of a polyprotein precursor encoded by the full-length genome sequence of the wild-type JFH1 strain shown in SEQ ID NO: 1.

The capacity for virus production can be determined by measuring infectivity titers of culture supernatants. Infectivity titers can be measured by any method. In the present description, infectivity titers of culture supernatants as measured by a focus assay method are used as the criterion of the capacity for virus production. Specifically, infectivity titers may be determined by the method described in the Examples below.

The nucleic acid according to the present invention or replicon RNA prepared from such nucleic acid exhibits high efficiency for virus particle formation. Such properties are advantageous for mass production of viral proteins necessary for production of virus vaccines or for other purposes. The efficiency for virus particle formation can be determined by calculating the specific activity (=[infectivity titer of culture supernatant]/[amounts of Core proteins in culture supernatant]; relative infectivity titer) and using the determined value as the indicator. Specifically, the specific activity may be determined by the method described in the examples below.

Among the nucleic acids according to the present invention, the nucleic acids consisting of the nucleotide sequences as shown in SEQ ID NOs: 3 to 5 (full-length genome replicon RNAs) are excellent in terms of the capacity for virus production. Also, a nucleic acid comprising a full-length genome sequence comprising the 5'-untranslated region of the JFH1 strain, a sequence encoding a mutant polyprotein precursor encoded by the nucleotide sequence as shown in any of SEQ ID NOs: 3 to 5, and the 3'-untranslated region of the JFH1 strain (i.e., full-length genome replicon RNA) has a high capacity for virus production.

The nucleic acid according to the present invention may comprise a nucleotide sequence encoding a foreign protein, such as a selection marker protein or reporter protein (e.g., a marker gene). A marker gene encompasses a selection marker gene capable of imparting selectivity to a cell, so that the cell in which the gene is expressed is exclusively selected (i.e., a nucleotide sequence encoding a selection marker protein) and a reporter gene encoding a gene product that serves as an indicator of the gene expression (i.e., a nucleotide sequence encoding a reporter protein). Examples of preferred selection marker genes in the present invention include, but are not limited to, neomycin resistance genes, thymidine kinase genes, kanamycin resistance genes, pyrithiamin resistance genes, adenylyltransferase genes, zeocin resistance genes, hygromycin resistance genes, and puromycin resistance genes. Examples of preferred reporter genes in the present invention include, but are not limited to, transposon Tn9-derived chloramphenicol acetyltransferase genes, *Escherichia coli*-derived β-glucuronidase or β-galactosidase genes, luciferase genes, green fluorescent protein genes, jellyfish-derived aequorin genes, and secreted placental alkaline phosphatase (SEAP) genes.

The nucleic acid according to the present invention may comprise a nucleotide sequence encoding a foreign protein such as a selection marker protein or reporter protein, for example, a marker gene, within the polyprotein precursor-coding region. In such a case, a foreign protein such as a selection marker protein or reporter protein, to be inserted into the polyprotein precursor is not limited, but a reporter protein is preferred, and luciferase is more preferred, and *Renilla reniformis* luciferase is further preferred. An example of a nucleotide sequence of a gene encoding *Renilla reniformis* luciferase is shown in SEQ ID NO: 9.

When a foreign protein, such as a selection marker protein or reporter protein, including *Renilla reniformis* luciferase (a reporter protein is preferred, and luciferase is more preferred) is inserted into a polyprotein precursor, it is preferred that such foreign protein be inserted within the amino acid sequence of amino acids at positions 2394 to 2397 of the amino acid sequence as shown in SEQ ID NO: 2. When a foreign protein is inserted into a polyprotein precursor, specifically, it may be inserted between amino acids at positions 2394 and 2395, between amino acids at positions 2395 and 2396, or between amino acids at positions 2396 and 2397, as determined with reference to the amino acid sequence as shown in SEQ ID NO: 2. In the present invention, "a foreign protein is inserted (or incorporated) into the amino acid sequence of amino acids at positions 2394 to 2397 as determined with reference to the amino acid sequence as shown in SEQ ID NO: 2" refers to a situation in which an amino acid sequence comprising a foreign protein is added to any position within the sequence of amino acids at positions 2394 to 2397 as determined with reference to the amino acid sequence as shown in SEQ ID NO: 2, when providing a sequence alignment between an amino acid sequence of a polypeptide into which an amino acid sequence comprising a foreign protein has been inserted and the amino acid sequence as shown in SEQ ID NO: 2, regardless of the site into which a DNA fragment encoding the foreign protein is actually inserted. When a DNA fragment comprising an ORF encoding a foreign protein and the XhoI recognition sites at the 5' and 3' sides (5'-CTCGAG-3') is cleaved with XhoI and inserted into the AbsI recognition site (5'-CCTCGAGG-3') of DNA encoding the amino acid sequence as shown in SEQ ID NO: 2, for example, a foreign protein comprising an amino acid sequence starting from the amino acid sequence Leu-Glu corresponding to the XhoI recognition site would be incorporated into the amino acid sequence consisting of amino acids at positions 2394 to 2397 (i.e., Pro-Leu-Glu-Gly) of the amino acid sequence as shown in SEQ ID NO: 2, corresponding to the AbsI recognition site. In such a case, a site into which a foreign protein can be actually inserted between the amino acid residue at position 2394 (Pro) and the amino acid residue at position 2395 (Leu) of the amino acid sequence as shown in SEQ ID NO: 2. However, the insertion site may be defined to be between the amino acid residue at position 2395 (Leu) and the amino acid residue at position 2396 (Glu), or between the amino acid residue at position 2396 (Glu) and the amino acid residue at position 2397 (Gly). Thus, it would not be appropriate to precisely identify a site into which a fragment was actually inserted. In this case, also, it is apparent that the additional amino acid sequence containing a foreign protein in any position within the amino acid sequence consisting of the amino acids at positions 2394 to 2397 of SEQ ID NO: 2 is present. Accordingly, such foreign protein is inserted (or incorporated) into the amino acid sequence of the amino acids at positions 2394 to 2397.

Virus particles containing the full-length genomic nucleic acid comprising a sequence encoding a polyprotein precursor into which a foreign protein has been inserted in the manner as described above exhibit infectivity titers 5 times or more as high and preferably 10 times or more as high than those of virus particles of the wild-type JFH1 strain. Examples of preferred full-length HCV genome sequences encoding a polyprotein precursor in which a foreign protein has been inserted into the amino acid sequence of the amino acids at positions 2394 to 2397 as determined with reference to the amino acid sequence as shown in SEQ ID NO: 2 (e.g., the insertion site can be also defined to be between the amino acids at positions 2394 and 2395) are shown in SEQ ID NOs: 6 and 7.

It is also preferred that the nucleic acid according to the present invention further comprise an IRES sequence. In the present invention, the term "IRES sequence" refers to an internal ribosome entry site, which allows for translation initiation via binding of a ribosome in the middle of RNA. Preferred examples of IRES sequences in the present invention include, but are not limited to, EMCV IRES (the internal ribosome entry site of the encephalomyocarditis virus), FMDV IRES, and HCV IRES. When the nucleic acid comprises an IRES sequence, it is preferred that a reporter gene (a nucleotide sequence encoding a reporter protein) followed by an IRES sequence be inserted between a 5'-untranslated region (5' NTR) and a Core protein-coding nucleotide sequence of the HCV genome sequence.

The nucleic acid according to the present invention can be prepared by introducing nucleotide substitutions that cause one or more amino acid substitutions described above into a nucleic acid comprising a sequence encoding a polyprotein precursor of the HCV JFH1 strain by a genetic engineering technique known in the art. A nucleic acid comprising a sequence encoding a polyprotein precursor of the HCV JFH1 strain may be, for example, DNA comprising the nucleotide sequence as shown in SEQ ID NO: 1 or a recombinant vector comprising the same (e.g., a recombinant plasmid vector), although a nucleic acid is not limited thereto.

The nucleotide substitutions that cause amino acid substitutions described above can be easily identified by comparing an amino acid codon after substitution with an amino acid codon before substitution based on the genetic code table that is well-known in the biology field.

The present invention also provides a vector comprising the nucleic acid according to the present invention. A vector comprising the nucleic acid according to the present invention may be a recombinant vector, and more preferably, an expression vector. It is preferred that the nucleic acid according to the present invention be inserted downstream of a transcriptional promoter in a vector. The nucleic acid according to the present invention is operably ligated to the transcriptional promoter so as to be placed under the control of the transcriptional promoter. Examples of transcriptional promoters include, but are not limited to, T7 promoters, SP6 promoters, and T3 promoters, and particularly preferably, T7 promoters. Examples of vectors to be used include, but are not limited to, pUC19 (TaKaRa), pBR322 (TaKaRa), pGEM-T (Promega), pGEM-T Easy (Promega), pGEM-3Z (Promega), pSP72 (Promega), pCRII (Invitrogen), and pT7Blue (Novagen). HCV replicon RNA can be synthesized from an expression vector with the use of, for example, the MEGAscript T7 kit (Ambion). Prepared HCV replicon RNA may be extracted and purified by RNA extraction techniques, purification techniques, or other techniques well-known in the art.

(2) Production of Cells Producing Infectious HCV Particles

The present invention also relates to HCV particles produced with the use of the mutant nucleic acid according to the present invention described in (1). Preferably, such HCV particles are infectious virus particles.

The HCV particles according to the present invention (preferably, infectious HCV particles) can be prepared by introducing full-length genome RNA comprising the nucleic acid of (1) into a cell and culturing the same. The present invention also provides HCV particles comprising the nucleic acid according to the present invention described in (1) above.

RNA may be introduced into any cells, provided that such cells permit formation of HCV particles, and preferably, cultured cells. Examples of such cells include cultured cells such as Huh7 cells, HepG2 cells, IMY-N9 cells, HeLa cells, 293 cells, and derivatives of any of such cells. More preferred examples are liver-derived cultured cells, such as the Huh7 cells. Preferred examples further include the Huh7 cells and derivatives of the Huh7 cells (e.g., Huh7.5 and Huh7.5.1 cells). Preferred examples also include Huh7 cells, HepG2 cells, IMY-N9 cells, HeLa cells, or 293 cells genetically engineered to express the CD81 and/or Claudin1 genes therein. Particularly, Huh7 cells or derivatives of Huh7 cells are preferably used. In the present invention, the term "derivative" refers to cell strains derived from cells of interest. The derivatives are generally subclones of cells of interest.

RNA can be introduced into a cell by any known introduction technique. Examples of such techniques include the calcium phosphate coprecipitation method, the DEAE-dextran method, lipofection, microinjection, and electroporation, and preferably, lipofection and electroporation, and more preferably, electroporation.

The capacity of cells to produce virus particles can be detected using antibodies against elements constituting HCV particles (e.g., Core proteins, E1 proteins, or E2 proteins) released into a culture solution. Also, HCV genome RNA from HCV particles in a culture solution may be amplified by RT-PCR using specific primers and detected, so that the presence of HCV particles can be detected indirectly.

Whether or not the produced viruses have infectivity can be determined by applying (adding) a supernatant obtained by culturing cells into which HCV RNA had been introduced in the manner described above to HCV-permissive cells (e.g., Huh7 cells), and immunostaining the cells with anti-Core antibodies after 48 hours to count the number of infected cells. Alternatively, cell extracts of the treated cells are subjected to electrophoresis on SDS-polyacrylamide gel, and Core proteins are detected via Western blotting for the determination of the virus infectivity. Herein, infectious HCV particles produced from cells into which genome RNA of the JFH1 strain has been introduced are also referred to as the JFH1 viruses.

The cells prepared in the manner described above into which full-length genome RNA has been introduced may be regularly subcultured. Thus, cells that continuously produce infectious HCV particles can be obtained. Such cell strains are capable of long-time culture. Cells capable of long-time culture that continuously produce infectious HCV particles are excellent in terms of the capacity to continuously produce HCV particles necessary for HCV vaccines.

The present invention also relates to cells (and preferably cultured cells) that produce HCV particles of the JFH1 variant prepared in the manner described above.

(3) Analysis of Adaptive Mutation

It was expected that continuous subculture of cell strains that continuously produce HCV particles prepared in (2) above would cause adaptive mutations in the HCV genome, which would in turn significantly increase HCV particle productivity. In general, subculture is carried out more than 10 times for 1 to 2 months. In the present invention, subculture was continued for one year, and preferably two years, in order to introduce adaptive mutation.

It is reported that, depending on combinations of adaptive mutations, the efficiency for RNA replication may be increased to 200 times or more or reduced to one-fifth or lower, and thus mere increase in the number of adaptive mutations is not necessarily sufficient and conditions are complicated (Lohmann, V. et al. J. Virol., 77: 3007-3019, 2003). A different HCV strain exhibits different effects of adaptive mutations, and the way that adaptive mutation affects the efficiency for HCV genome replication is not known in detail. The nucleic acid according to the present invention described in (1) above can be an adapted variant obtained via introduction of such adaptive mutations.

(4) Use of HCV Particles

The HCV particles obtained in (2) above are preferably used for vaccines and as antigens for preparing anti-HCV antibodies.

Specifically, HCV particles can be used as vaccines without any processing; however, HCV particles can be attenuated or inactivated by methods known in the art. Viruses can be inactivated by adding an inactivating agent, such as formalin, β-propiolactone, or glutaldialdehyde, to, e.g., a virus suspension, mixing the same, to allow the inactivating agent to react with viruses (Appaiahgari, M. B. & Vrati, S., Vaccine, 22: 3669-3675, 2004). Accordingly, the present invention also relates to HCV vaccines obtained by inactivating the HCV particles obtained in (2).

The vaccine of the present invention is generally prepared in such a manner that it can be administered in the form of a liquid or suspension. The vaccine of the present invention may be prepared in the form of a solid suitable for dissolution or suspension into a liquid. The preparation may be in the form of a liquid emulsion or encapsulated into a liposome. Active immunogenic components, such as HCV particles, are often mixed with pharmaceutically acceptable excipients that are compatible with the active components. Examples of suitable excipients include water, physiological saline, dextrose, glycerol, ethanol, and a mixture of any thereof. In addition, the vaccine may comprise, if desired, a small amount of auxiliary material (e.g., a moistening agent or emulsifier), pH buffer, and/or at least one adjuvant for enhancing vaccine efficacy.

An adjuvant is a non-specific stimulatory factor to immunological systems. The adjuvant enhances the immune responses of a host against the HCV vaccine. Examples of possible effective adjuvants include, but are not limited to, aluminum hydroxide, N-acetyl-muramyl-L-threonyl-D-isoglutamine (thr-MDP), N-acetyl-nor-muramyl-L-alanyl-D-isoglutamine (CGP11637, referred to as "nor-MDP"), N-acetylmuramyl-L-alanyl-D-isoglutaminyl-L-alanine-2-(1'-2'-dipalmitoyl-sn-glycero-3-hydroxyphosphoryloxy)-ethylamine (CGP19835A, referred to as "MTP-PE"), and RIBI. RIBI comprises three components extracted from bacteria (i.e., monophosphoryl lipid A, trehalose dimycolate, and a cell wall skeleton (HPL+TDM+CWS)) in a 2% squalene/Tween®80 emulsion. Adjuvant efficacy can be determined by measuring the amounts of antibodies generated upon administration of the vaccines derived from HCV particles.

The vaccine of the present invention is generally administered parenterally, for example, by injection such as subcutaneous injection or intramuscular injection. Other dosage forms suitable for other administration embodiments include suppositories and, optionally, oral preparations.

In the case of injection preparations administered subcutaneously, intracutaneously, intramuscularly, or intravenously, for example, the HCV vaccine of the present invention can be administered in combination with a pharmaceutically acceptable carrier, a diluent, or the like, for example, stabilizers, carbohydrates (e.g., sorbitol, mannitol, starch, sucrose, glucose, and dextran), proteins such as albumin and casein, protein-containing substances such as bovine serum or defatted milk, and buffer (e.g., phosphate buffer).

Conventional binders and carriers used for suppositories can contain polyalkylene glycol or triglyceride, for example. Such suppositories can be prepared from a mixture containing active ingredients at a concentration of 0.5% to 50%, and preferably 1% to 20%. Oral preparations comprise excipients that are generally used. Examples of excipients include pharmaceutical-grade mannitol, lactose, starch, magnesium stearate, saccharin sodium, cellulose, and magnesium carbonate.

The vaccine of the present invention is in the form of a solution, suspension, tablet, pill, capsule, sustained-release formulation, or powder. It contains active ingredients (virus particles or part thereof) at a concentration of 10% to 95%, and preferably 25% to 70%.

The vaccine of the present invention is administered by a method suitable for a given dosage form and at an amount sufficient to exhibit preventive and/or therapeutic effects. A dose is generally 0.01 µg to 100,000 µg of antigens for a single administration. It varies depending on the patient to be treated, the capacity for antibody synthesis in the immune system of the patient, the degree of defense desired, and the route of administration, such as oral, subcutaneous, intracutaneous, intramuscular, or intravenous administration.

The vaccine of the present invention can be administered on single-dosing schedules, or preferably on multiple-dosing schedules. In the case of multiple-dosing schedules, 1 to 10 separate administrations are carried out at the initial stage of inoculation, and further administrations can be carried out at intervals required for maintaining and/or enhancing the immune responses. For example, the next administration can be carried out 1 to 4 months later. If necessary, subsequent administration can be carried out several months later. The administration regimen is also, at least partially, determined depending on an individual's needs, and it depends on the judgment made by a doctor.

In addition, the vaccine comprising the HCV particles of the present invention can be administered in combination with another immunosuppressive agent (e.g., immunoglobulin).

Further, the vaccine of the present invention may be administered to a healthy individual to induce immune responses against HCV, for preventing a healthy individual from being newly infected with HCV. Furthermore, the vaccine of the present invention may be used as a therapeutic vaccine for eliminating HCV by administering the vaccine to a patient infected with HCV to induce a potent immune response against HCV in the body.

The HCV particles of the present invention are useful as antigens for antibody production. The HCV particles of the present invention are administered to mammalian animals or avian species, so that antibodies can be prepared. Examples of mammalian animals include mice, rats, rabbits, goats, sheep, horses, cattle, guinea pigs, *Camelus dromedarius, Camelus bactrianus*, and *Lama glama*. *Camelus dromedarius, Camelus bactrianus*, and *Lama glama* are preferably used to prepare heavy (H) chain antibodies. Examples of avian species include chickens, geese, and ostriches. Blood sera are collected from animals to which the HCV particles of the present invention have been administered, and antibodies can be obtained therefrom in accordance with known techniques.

Cells of animals immunized with the HCV particles of the present invention may be used to prepare hybridomas, i.e., monoclonal antibody-producing cells. Methods for preparing hybridomas are well-known, and the method described in Antibodies: A Laboratory Manual (Cold Spring Harbor Laboratory, 1988) can be employed.

Monoclonal antibody-producing cells may be prepared by cell fusion. Alternatively, monoclonal antibody-producing cells may be prepared via other techniques, such as introduction of DNA of a cancer gene or immortalization of B lymphocytes by infection with Epstein-Barr viruses.

Monoclonal or polyclonal antibodies obtained by those techniques are useful for diagnosis, treatment, or prevention of HCV. Anti-HCV antibodies that recognize the HCV particles of the present invention as antigens are also within the scope of the present invention.

Antibodies prepared with the use of the HCV particles of the present invention are administered in combination with pharmaceutically acceptable solubilizers, additives, stabilizers, buffers, or other substances. Any route of administration may be used. Subcutaneous, intracutaneous, or intramuscular administration is preferred and intravenous administration is more preferred.

(5) Use in Screening for Anti-HCV Agent

Because of a lack of animals that effectively reflect virus infection other than chimpanzees and effective in vitro virus culture systems, it has been difficult to thoroughly evaluate drugs. Such disadvantages have been impediments to the development of therapeutic agents against HCV infection. In recent years, however, a subgenomic HCV replicon system capable of evaluating HCV-RNA replication was developed (Lohmann, V. et al., Science, 285: 110-113, 1999), and such development has led to significant progress in realizing a system for screening for HCV inhibitors associated with inhibition of virus replication.

The subgenomic HCV replicon system, however, suffered from a drawback to the effect that it could not be used to evaluate functions of HCV structural proteins. In fact, a Core protein, which is one of HCV structural proteins, is known to influence a transcriptional factor of a host. When phenomena that occur in cells infected with HCV are evaluated, accordingly, the use of the subgenomic HCV replicon system is insufficient. It is deduced that drugs selected via screening using a subgenomic HCV replicon system may not be capable of sufficiently inhibiting HCV replication.

In order to overcome the drawbacks of the subgenomic HCV replicon system, a full-length genome HCV replicon system was developed using the HCV N strain (genotype 1b), the HCV Con-1 strain (genotype 1b), and the HCV H77 strain (genotype 1a) (Ikeda, M. et al., J. Virol., 76: 2997-3006, 2002; Pietschmann, T. et al., J. Virol., 76: 4008-4021, 2002; and Blight, K. J. et al., J. Virol., 77: 3181-3190, 2003). While a full-length RNA comprising the structural protein regions of such HCV strains was introduced into cells, no virus particles were released into a culture solution (Blight, K. J. et al., J. Virol., 77: 3181-3190, 2003). With such full-length genome HCV replicon system, disadvantageously, viruses could not be released, and therapeutic agents acting during infection could not be screened.

When screening for an anti-HCV agent using HCV replicons, infectious HCV particles and cells that permit HCV infection, such as Huh7 cells, are cultured in the presence of a test substance, and HCV replication and/or particle production are assayed to evaluate anti-HCV effects of the test substance. In order to monitor HCV replication and particle production, it is necessary to assay the amount of HCV genomes by PCR or Northern blotting or to perform detection and assay of the Core proteins or non-structural proteins (e.g., NS3 proteins) by EIA or cellular immunostaining (Aoyagi, K. et al., J. Clin. Microbiol., 37: 1802-1808, 1999). These assay techniques are complicated, high-throughput assays are difficult to perform, and such techniques are thus cost-ineffective. Accordingly, development of evaluation techniques that can be carried out in a simple and cost-effective manner has been awaited for anti-HCV agent screening. Thus, a method comprising preparing a replicon by incorporating a reporter gene into the full-length genome HCV and monitoring a reporter protein translated from the reporter gene in the genome as a result of autoreproduction of the replicon was invented. For example, Luc-JFH1, Luc-Jc1, and Luc-Con1 vectors in which the luciferase gene as a reporter gene and EMCV IRES have been inserted between 5' NTR and a Core protein-coding gene in JFH1, J6CF/JFH1 (Jc-1), and Con1/JFH1, were prepared, and functions thereof were tested (Koutsoudakis, G, et al. J. Virol., 80: 5308-5320, 2006). When viruses having such reporter-selectable full-length genome HCV replicons are prepared and the Huh7 cells are infected therewith, a luciferase gene as a reporter gene is expressed and luciferase is synthesized in an infected cell. Since effects of infection can be evaluated by assaying luciferase activity, assays of the HCV genomes or proteins become unnecessary. Thus, such technique is very convenient.

With the insertion of a foreign gene such as a reporter gene, however, the genome size is increased, and the replication efficiency is likely to decline significantly. Compared with JFH1, in fact, the replication capacity of Luc-JFH1 is 5 times lower, and the infectivity titer is 3 to 10 times lower (Koutsoudakis, G, et al. J. Virol., 80: 5308-5320, 2006). In order to use virus particles having full-length HCV genomes expressing reporter genes for screening, accordingly, development of HCV viruses with higher infectivity titer is necessary.

According to the present invention, a full-length genome replicon derived from a JFH1 variant that retains high replication capacity even though a reporter gene had been introduced thereinto was prepared. With the use of the full-length genome replicon of the present invention, an efficient screening method can be provided. Such screening method is also within the scope of the present invention.

In this screening method, HCV RNA (full-length genome replicon RNA) having a full-length genome sequence comprising a marker gene inserted into the polyprotein precursor-coding sequence, and in particular, at a site corresponding to within the sequence of the amino acids at positions 2394 to 2397 as determined with reference to the amino acid sequence as shown in SEQ ID NO: 2 (e.g., a site between the amino acids at positions 2394 and 2395 as determined with reference to the amino acid sequence as shown in SEQ ID NO: 2), can be used with advantage. A reporter protein is preferably used as a marker gene.

The JFH1 variant-derived full-length genome replicon into which a reporter protein-coding sequence has been incorporated that can be preferably used for the screening method of the present invention can be a nucleic acid comprising, in the 5' to 3' direction, the 5'-untranslated region of the adapted variant of JFH1 of the present invention, a reporter protein coding sequence, the IRES sequence of EMCV (encephalomyocarditis virus), and the Core protein coding sequence, the E1 protein coding sequence, the E2 protein coding sequence, the p7 protein coding sequence, the NS2 protein coding sequence, the NS3 protein coding sequence, the NS4A protein coding sequence, the NS4B protein coding sequence, the NS5A protein coding sequence, the NS5B protein coding sequence and the 3'-untranslated region of the adapted variant of JFH1.

More preferably, the replicon can be a nucleic acid comprising, in the 5' to 3' direction, the 5'-untranslated region, the Core protein coding sequence, the E1 protein coding sequence, the E2 protein coding sequence, the p7 protein coding sequence, the NS2 protein coding sequence, the NS3 protein coding sequence, the NS4A protein coding sequence, the NS4B protein coding sequence, a sequence encoding a protein in which a reporter protein is inserted functionally (i.e., in-frame) into the NS5A protein, the NS5B protein coding sequence, and the 3'-untranslated region of the adapted variant of JFH1 of the present invention.

As the adapted variant of JFH1 of the present invention, the nucleic acid according to the present invention described in (1) above can be preferably used.

Particularly preferably, the replicon can be a nucleic acid encoding a protein in which a reporter protein is inserted functionally (in-frame) into the amino acid sequence of the amino acids at positions 2394 to 2397 counted from the N terminus of the HCV polyprotein precursor (e.g., between the amino acids 2394 and 2395).

Examples of reporter proteins include luciferase, secreted alkaline phosphatase, green fluorescent protein (GFP), β-lactamase, chloramphenicol acetyltransferase, and a fusion protein of neomycin phosphotransferase and luciferase. Luciferase is preferred, and *Renilla reniformis* luciferase is more preferred. An example of a nucleotide sequence of a gene encoding *Renilla reniformis* luciferase is shown in SEQ ID NO: 9.

A particularly preferred sequence of a replicon comprising a reporter gene incorporated into the full-length genome HCV is a nucleic acid consisting of the nucleotide sequence as shown in SEQ ID NO: 6 or 7. When the nucleic acid is RNA, nucleotide "T" in the nucleotide sequence is replaced with "U." The infectious HCV particles of the present invention can be prepared using HCV genome RNA or HCV genome DNA. With the use of such full-length genome replicon HCV RNA, a highly sensitive assay system for HCV infection using luciferase activity as an indicator can be provided.

The screening method involving the use of a replicon comprising a reporter protein-coding sequence incorporated into the full-length genomic HCV RNA of the present invention may be a method for screening for an anti-hepatitis C virus substance comprising, for example: introducing the replicons into cultured cells to prepare cultured cells producing hepatitis C virus particles; culturing (i) the resulting cultured cells producing hepatitis C virus particles or (ii) the hepatitis C virus particles released from the cells into a culture supernatant in combination with hepatitis C virus-sensitive cells (cells that permit HCV infection) in the presence of a test substance; and detecting reporter proteins in the culture product. Such screening method can be used as a drug evaluation system.

A specific example of such drug evaluation system is a method for screening for a substance having anti-HCV activity. Such method comprises: (1) culturing infectious HCV particles comprising a replicon having a reporter gene integrated into the full-length HCV genome as the genome, together with cells that permit HCV infection (e.g., Huh7 cells), in the presence of a test substance; (2) assaying the reporter proteins produced upon HCV replication and particle production; and (3) comparing the level of the produced reporter proteins with that of the reporter proteins detected in a control sample without test substance added to evaluate the anti-HCV effects of the test substance.

Another example of the screening method of the present invention comprises: (1) culturing infectious HCV particle-producing cells comprising, as the genome, a replicon having a reporter gene integrated into full-length HCV genome in the presence of a test substance; (2) assaying the reporter proteins produced upon HCV replication and particle production; and (3) comparing the level of the produced reporter proteins with that of the reporter proteins detected in a control sample without test substance added to evaluate the anti-HCV effects of the test substance.

More specifically, this screening method may be a method for screening for an anti-hepatitis C virus substance comprising a step of culturing cultured cells producing a hepatitis C virus particles containing the nucleic acid according to the present invention, which is the full-length genomic HCV RNA of a JFH1 variant into which a nucleic acid encoding a reporter protein has been inserted, in the presence of a test substance, and a step of detecting the reporter protein in the resulting culture and determining the test substance as having an anti-hepatitis C virus activity when the reporter protein expression level is lower.

(6) Summary of SEQ ID NOs

SEQ ID NO 1: full-length genome sequence of wild-type JFH1 (JFH1wt)

SEQ ID NO: 2: amino acid sequence of polyprotein precursor encoded by full-length genome sequence of wild-type JFH1 (JFH1wt)

SEQ ID NO: 3: full-length genome sequence of variant JFH1-A/WT; a region spanning from nucleotides 341 to 9442 being a polyprotein precursor coding sequence.

SEQ ID NO: 4: full-length genome sequence of variant JFH1-B/WT; a region spanning from nucleotides 341 to 9442 being a polyprotein precursor coding sequence.

SEQ ID NO: 5: full-length genome sequence of variant JFH1-Q862R; a region spanning from nucleotides 341 to 9442 being a polyprotein precursor coding sequence.

SEQ ID NO: 6: full-length genome sequence of variant JFH1-A/WT-Rluc; a region spanning from nucleotides 341 to 10381 being a protein coding sequence.

SEQ ID NO: 7: full-length genome sequence of variant JFH1-B/WT-Rluc; a region spanning from nucleotides 341 to 10381 being a protein coding sequence.

SEQ ID NO: 8: full-length genome sequence of variant JFH1wt-Rluc; a region spanning from nucleotides 341 to 10381 being a protein coding sequence.

SEQ ID NO: 9: full-length sequence of *Renilla reniformis* luciferase gene

SEQ ID NOs: 10 to 18: PCR primers

EXAMPLES

Hereafter, the present invention is described in greater detail with reference to the examples, but the technical scope of the present invention is not limited to these examples.

Example 1

Preparation of Adapted Variant of JFH1 for Enhanced Production of JFH1 Virus Particles pJFH-1 (Wakita, T. et al., Nat. Med., 11, 2005, pp. 791-796 and International Publication WO 2004/104198) was used as a source of DNA. pJFH-1 is a plasmid DNA in which cDNA of the entire genome RNA region (full genome cDNA; SEQ ID NO: 1) of the hepatitis C virus (HCV) JFH1 strain of genotype 2a isolated from a Japanese patient with fulminant hepatitis (GenBank Accession No: AB047639; JP 2002-171978 A) was cloned into the EcoRI-XbaI site located downstream of the T7 promoter sequence in the T7 promoter-inserted pUC19 plasmid vector. pJFH-1 was cleaved with XbaI, Mung Bean Nuclease 20 U (the total amount of reaction solution: 50 µl) was added thereto, and the resultant was incubated at 30° C. for 30 minutes to give blunt-ends from XbaI-cleaved end. Subsequently, phenol-chloroform extraction and ethanol precipitation were carried out to obtain an XbaI fragment from which 4 nucleotides (CTAG) at the cleaved end had been removed. This DNA fragment was used as a template to synthesize RNA using the MEGAscript T7 kit (Ambion). The synthesized full-length genomic HCV RNA of the JFH1 strain was introduced into cells in the manner described below.

Huh7 cells (1×10$^6$ cells) were seeded in a 10-cm culture dish on the previous day and cultured in an antibiotic-free medium. Full-length genomic HCV RNA of the JFH1 strain (6 µg) suspended in 1 ml of OPTI-MEM (Invitrogen) was added to 30 µl of a mixture of Lipofectamine 2000 (Invitrogen) and OPTI-MEM (Invitrogen), and the reaction was allowed to proceed at room temperature for 20 minutes to form an RNA-Lipofectamin complex. The RNA-Lipofectamin complex was added to the Huh7 cells prepared on the previous day. After 24 hours, a supernatant was exchanged with a fresh medium. Thereafter, subculture was continuously carried out for 2 years. This subculture duration is considerably longer than a general culture duration, during which subculture is carried out more than 10 times for 1 to 2 months, to obtain culture-adapted variants. The virus strain produced by the cell after the completion of the subculture was designated as "JFH1a."

Figure 1:
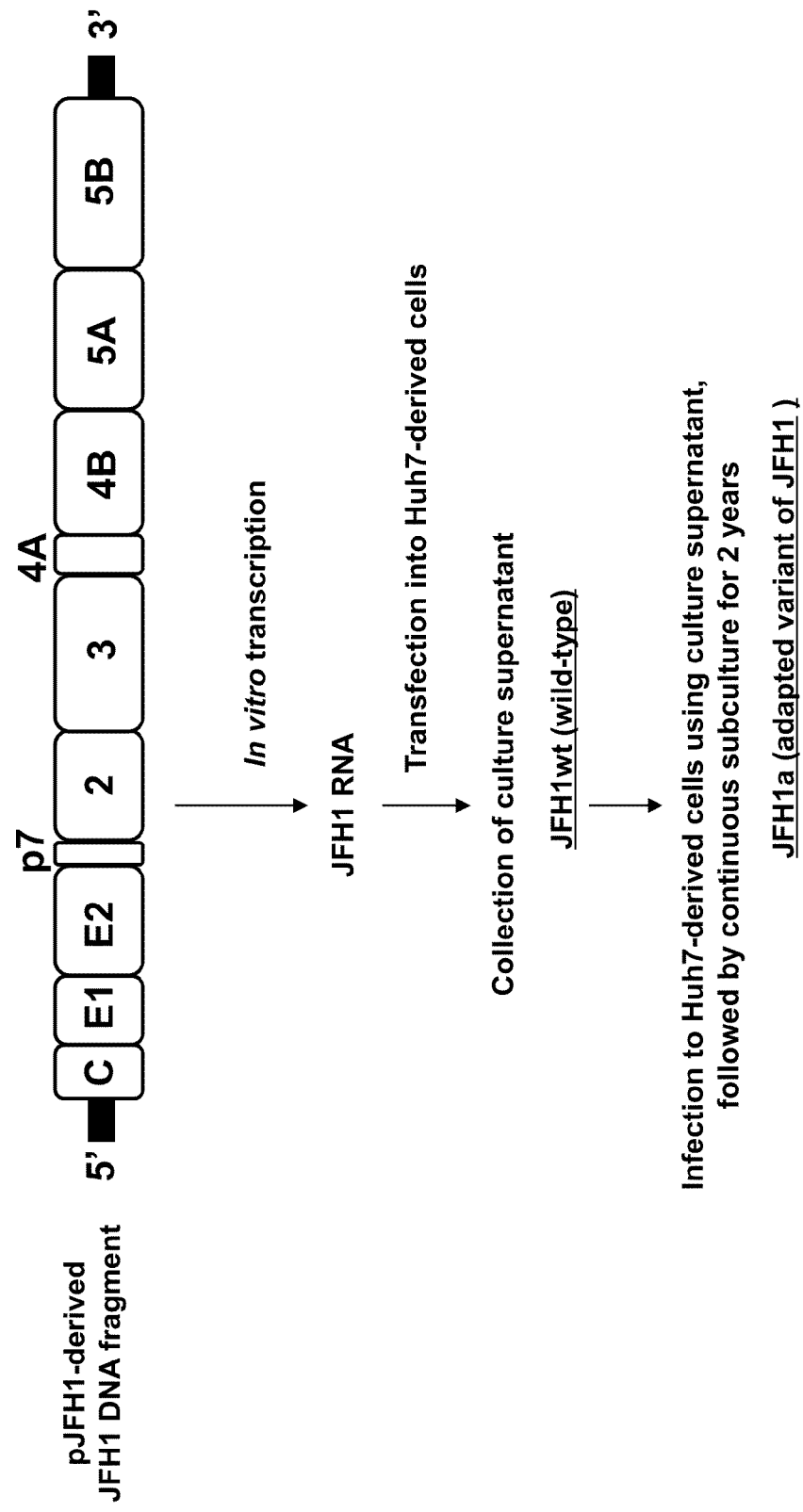
FIG. 1 shows a scheme of an experiment conducted to obtain an adapted variant of JFH1. In the figure, "C" denotes a region encoding a Core protein, "E1" denotes a region encoding E1 protein, "E2" denotes a region encoding E2 protein, "p'7" denotes a region encoding p7 protein, "2" denotes a region encoding NS2 protein, "3" denotes a region encoding NS3 protein, "4A" denotes a region encoding NS4A protein, "4B" denotes a region encoding NS4B protein, "5A" denotes a region encoding NS5A protein, and "5B" denotes a region encoding NS5B protein. A region at the 5' end adjacent to C (Core) is the 5'-untranslated region and a region at the 3' end adjacent to 5B (NS5B) is the 3'-untranslated region. The same applies to FIGS. 5, 9, 10, and 15.

Meanwhile, full-length genomic HCV RNA of the JFH1 strain, which was synthesized in the manner described above (full-length genomic HCV RNA synthesized from the wild-type JFH1 strain), was introduced into the Huh7.5.1 cell in the manner described above. A virus strain generated by a cell into which RNA of the wild-type JFH1 strain had been introduced immediately after the initiation of culture was designated as "JFH1wt." FIG. 1 shows a scheme of an experiment conducted in the Example.

Example 2

Characterization of JFH1a, Which is an Adapted Variant of JFH1

Figure 2:
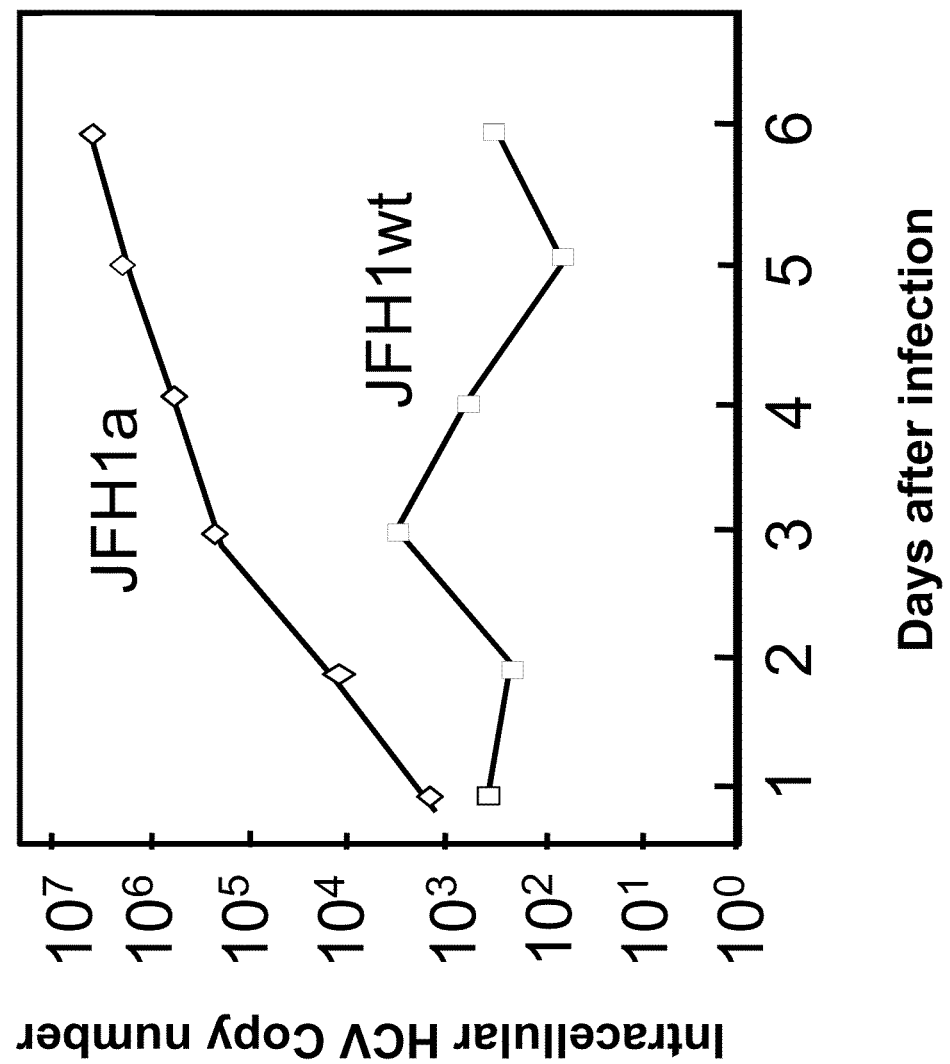
FIG. 2 shows the replication capacity of the adapted variant of JFH1 (JFH1a) obtained by subculturing the JFH1 virus-infected cells for 2 years.

Huh7.5.1 cells were seeded in a 24-well plate at 2×10$^4$ cells/well 24 hours before virus infection. Subsequently, Huh7.5.1 cells were infected with the JFH1wt or JFH1a virus particles prepared in Example 1 at the multiplicity of infection (M.O.I.) of 0.006 at 37° C. for 2 hours. A virus solution was removed, a fresh medium was added, and culture was conducted at 37° C. for consecutive 7 days. Cells were collected over time and total RNA was extracted. Total RNA was extracted using a commercially available RNA extraction reagent (Isogen, Nippon Gene) in accordance with the accompanying protocols. RNA was quantified via two-step RT-PCR and converted into cDNA using the ReverTra Ace qPCR RT Kit (TOYOBO), and PCR was carried out via SYBR Green I detection. The obtained PCR product was analyzed using a Light Cycler (Roche) and intracellular HCV RNA was quantified. Sequences of primers used for detecting JFH1a genome were designed to amplify the HCV NS3 region as follows: 5'-CTTTGACTCCGTGATCGACC-3' (SEQ ID NO: 10) and 5'-CCCTGTCTTCCTCTACCTG-3' (SEQ ID NO: 11). Primers for amplifying the actin gene for normalization, 5'-TGGCACCCAGCACAATGAA-3' (SEQ ID NO: 12) and 5'-CTAAGTCATAGTCCGCCTA-GAAGCA-3' (SEQ ID NO: 13) were used to carry out quantification by two-step RT-PCR in the same manner, and the copy number of the HCV RNA per 100 ng of total RNA was determined based on the obtained data (FIG. 2). As a result, JFH1a was found to exhibit a replication capacity approximately 1,000 times as more high as that of JFH1wt on the 6th day of culture.

Figure 3:
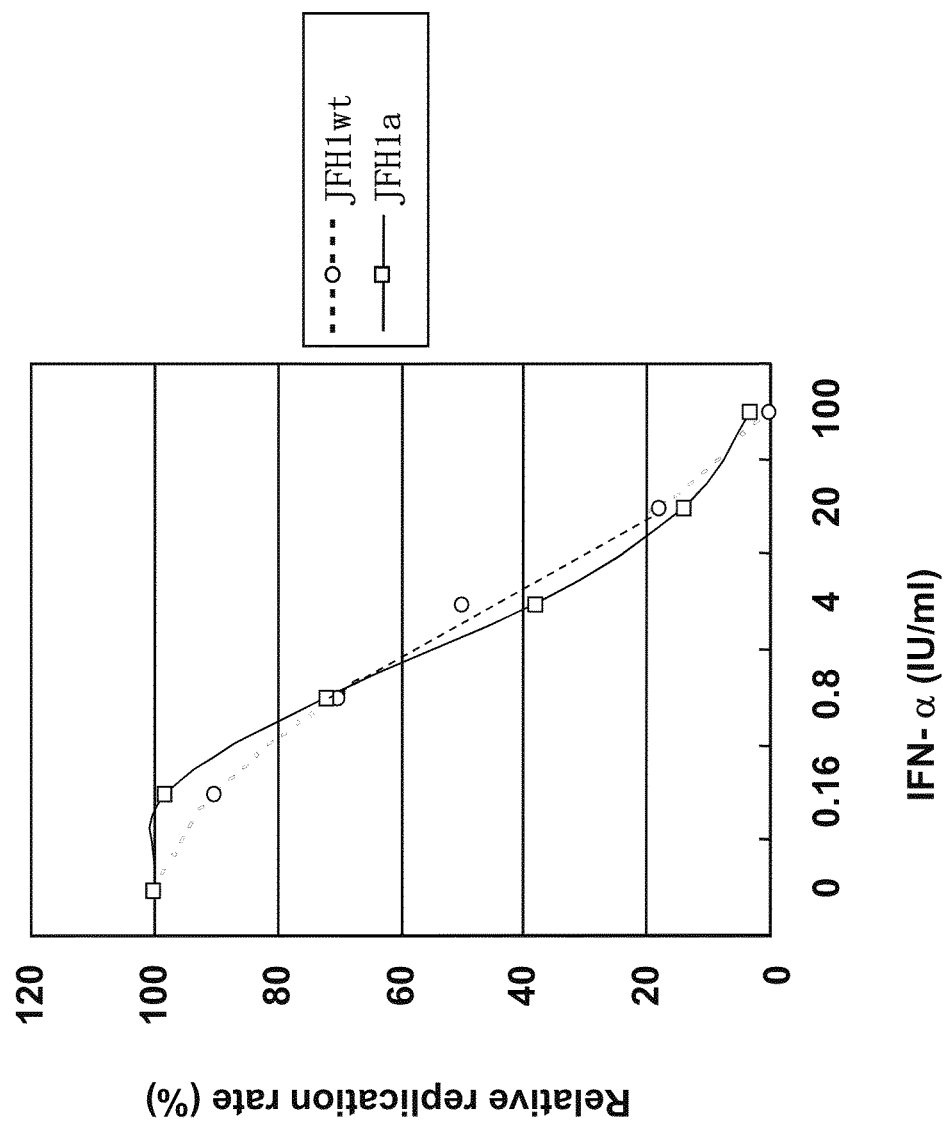

Subsequently, interferon sensitivity of JFH1wt and JFH1a was analyzed. Huh7.5.1 cells were seeded in a 24-well plate at 3×10$^4$ cells/well 24 hours before virus infection. On the following day, the cells were infected with the JFH1wt and JFH1a at M.O.I. of 0.006 for 2 hours. Thereafter, the cells were washed three times with PBS (−) and then cultured in media containing interferon α (IFN-α) (Universal Type I Interferon; PBL InterferonSource) at the concentrations indicated in FIG. 3 (0, 0.16, 0.8, 4, 20, and 100 IU/ml) for 72 hours. The amount of intracellular HCV RNA treated at the IFN-α concentrations indicated in FIG. 3 was quantified via quantitative RT-PCR in the manner described above. The relative replication rate (%) compared to the control without interferon α (IFN-α) added (corresponding to 0 IU/ml of IFN-α indicated in FIG. 3) was determined based on the obtained data. As a result, JFH1a was found to exhibit interferon sensitivity similar to that of the wild-type JFH1wt strain (FIG. 3).

Example 3

Analysis of Mutations in JFH1a

In this Example, the JFH1a genome was first subjected to sequence analysis in order to identify adaptive mutations critical for the high capacity of JFH1a for virus particle production. Total RNA was extracted from the JFH1a-virus-infected cells obtained in Example 2 using ISOGEN-LS (Nippon Gene) and cDNA was synthesized via reverse transcription. Reverse transcription for cDNA synthesis was carried out using the specific primer A9482 (5'-GGAACAGT-TAGCTATGGAGTGTACC-3' (SEQ ID NO: 16)) and the Transcriptor First Strand cDNA Synthesis Kit (Roche). Reverse transcription was carried out in accordance with the accompanying protocols. The resulting cDNA was used as a template to amplify, via PCR, a sequence encoding a region spanning from the Core protein to the NS3 protein. PCR primers S58 (5'-TGTCTTCACGCAGAAAGCGCCTAG-3' (SEQ ID NO: 17) and AS4639 (5'-CTGAGCTGGTATTATG-GAGACGTCC-3' (SEQ ID NO: 18)) were used. A DNA fragment obtained by PCR was ligated into the pGEM-T Easy vector (Promega), transformed into *E. coli* DH5a, and cultured on an ampicillin-containing LB agar medium to select transformed *E. coli* cells. 6 colonies were picked up and cultured in an LB medium overnight, and plasmids were extracted and purified therefrom using the Wizard Plus SV Miniprep DNA Purification System (Promega), and a nucleotide sequence of a DNA fragment amplified via PCR was verified.

As a result, a large number of amino acid substitutions (mutations) was observed in a region spanning from the Core protein to the NS3 protein of the JFH1a polyprotein precursor (i.e., the N-terminal half region of the polyprotein precursor) compared with the JFH1 polyprotein precursor sequence (SEQ ID NO: 2) (FIG. 4). Amino acid mutations that are common in two or more of 6 clones were observed (indicated by * in FIG. 4).

Example 4

Construction of Variant Plasmid

Plasmids having adaptive mutations necessary for the high capacity of JFH1a for virus particle production observed in Example 3 were constructed. Based on the patterns of mutated amino acids commonly observed in the nucleotide sequences of 6 clones as shown in FIG. 4, JFH1a was found to include at least 2 types of variant strains. They are referred to as Group A and Group B, respectively. Clone 5-2 was selected from Group A, Clone 5-4 was selected from Group B, and two types of chimeric variants were prepared using them. Clone 5-2 and Clone 5-4 were digested with AgeI and SpeI restriction enzymes, and DNA fragments of PCR-amplified regions having 5' side-mutations were obtained. These DNA fragments were ligated to the pJFH-1 vector fragments obtained by treatment with AgeI and SpeI restriction enzymes to prepare pJFH1-A/WT and pJFH1-B/WT, respectively.

Figure 5:
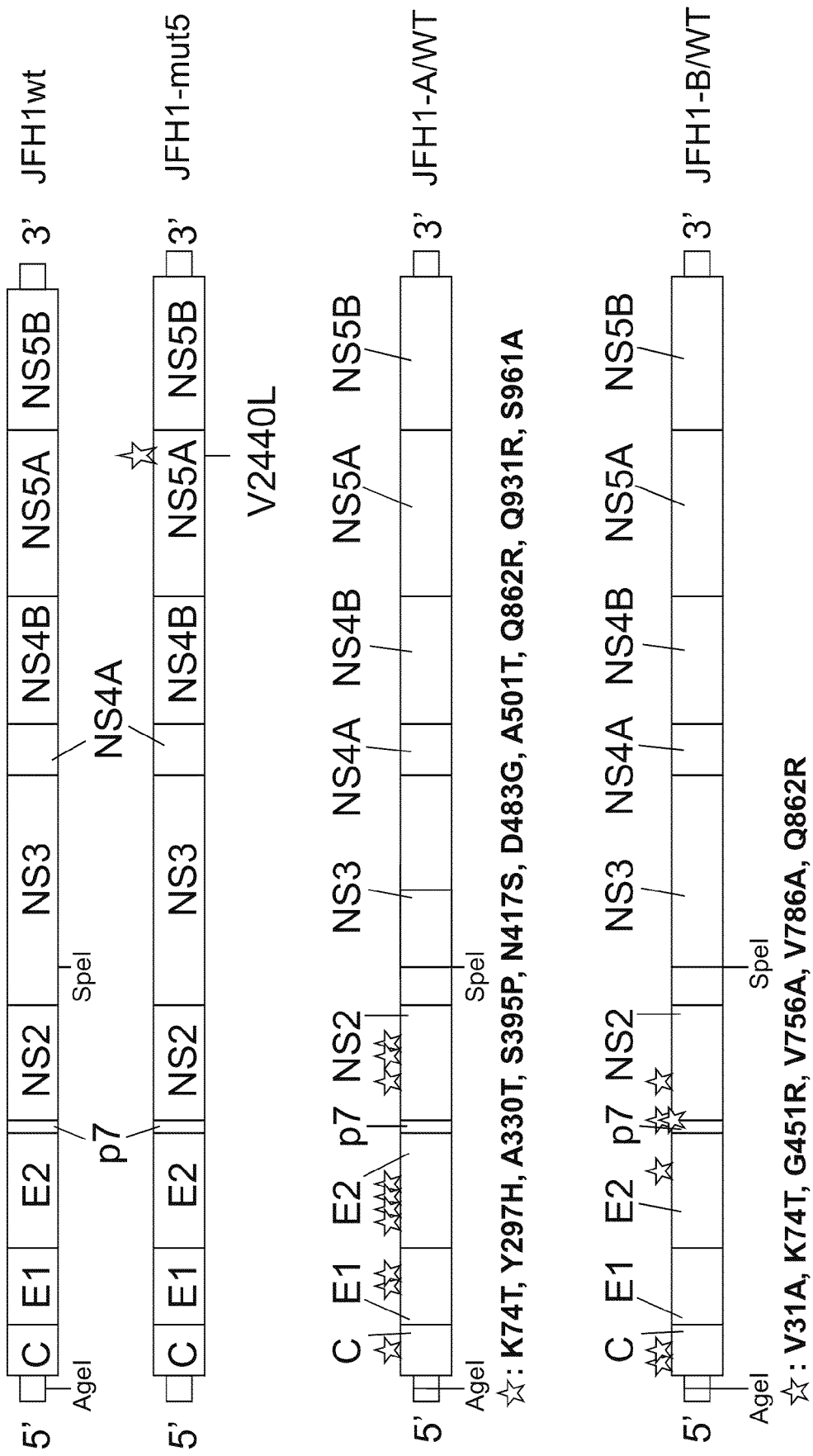
FIG. 5 is a schematic view showing the structures and mutation-introduced sites of the full-length HCV genomes (polyprotein precursor coding regions and untranslated regions) of the wild-type JFH1wt strain and variants thereof used for analysis of replication capacity and infectivity. Regions subjected to mutation analysis (AgeI-SpeI fragments) are denoted in gray. Mutation-introduced sites are indicated with stars.

FIG. 5 is a schematic view showing mutation-introduced sites in the HCV variant full-length genomes prepared from the variant plasmids. The HCV variant JFH1-A/WT expressed from the variant plasmid pJFH1-A/WT has the full-length genome sequence (SEQ ID NO: 3) encoding a protein comprising 10 amino acid substitutions (K74T, Y297H, A330T, S395P, N417S, D483G, A501T, Q862R, Q931R, and S961A) introduced into the N-terminal half region (from Core to part of NS3) of the amino acid sequence (SEQ ID NO: 2) of the polyprotein precursor of the wild-type JFH1 virus (also referred to as "JFH1wt"). The HCV variant JFH1-B/WT expressed from the variant plasmid pJFH1-B/WT has the full-length genome sequence (SEQ ID NO: 4) encoding a protein comprising 6 amino acid substitutions (V31A, K74T, G451R, V756A, V786A, and Q862R) introduced into the N-terminal half region (from Core to part of NS3) of the amino acid sequence (SEQ ID NO: 2) of the polyprotein precursor of the wild-type JFH1 virus (also referred to as "JFH1wt").

As a control, a plasmid in which the full-length genome sequence of the HCV variant JFH1-mut5 comprising the amino acid substitution V2440L introduced into the amino acid sequence of the JFH1wt polyprotein precursor is cloned under the control of the T7 RNA promoter was used. It is reported that the capacity of the JFH1-mut5 virus for virus production is 10 times or more high as that of JFH1wt (Kaul et al., J. Virol., 2007, 81: 13168-13179).

Example 5

Analysis of Capacity of HCV Adapted Variant for HCV Particle Production

The wild-type JFH1wt strain and three types of adapted variants thereof (JFH1-A/WT, JFH1-B/WT, and JFH1-mut5) were compared in terms of the capacities for virus particle production.

At the outset, the full-length genomic HCV RNAs of the four virus strains (i.e., JFH1wt, JFH1-A/WT, JFH1-B/WT, and JFH1-mut5) were synthesized by the method described in Example 1 using pJFH-1 and variant plasmids prepared in Example 4 as templates. Subsequently, the synthesized 4 types of HCV RNAs (4 μg each) were mixed with 100 μl of a suspension of Huh7.5.1 cells in Buffer R ($5 \times 10^6$ cells/ml) included in the Microporation kit (Digital Bio), and the resultant was subjected to electroporation for transfection using the MicroPorator (Digital Bio) by applying a single pulse (pulse voltage: 1350 V; pulse width: 30 ms). The cells were suspended in 10 ml of a medium and seeded in a 6-well plate at 2 ml ($2 \times 10^5$ cells)/well. The cells and the culture supernatant were collected 4, 24, 48, 72, and 96 hours after the transfection, and the amount of Core proteins newly produced in the cells was quantified by the Ortho HCV antigen IRMA test (Aoyagi et al., J. Clin. Microbiol., 37, 1999, pp. 1802-1808) (FIG. 6A). The amount of Core proteins in the culture supernatant was measured at some time points in the same manner (FIG. 6B). Transfection efficiency was corrected using the amount of intracellular Core proteins after 4 hours.

Virus infectivity titers of JFH1wt, JFH1-A/WT, JFH1-B/WT, and JFH1-mut5 in culture supernatants at the time points were determined by virus titer assay (focus forming assay). More specifically, Huh7.5.1 cells were seeded in a 96-well plate at $6 \times 10^3$ cells/well, the cells were infected with a culture supernatant serially diluted in a medium on the following day, and culture was then conducted at 37° C. for 72 hours. Virus-infected cells were detected via immunostaining based on antigen-antibody reactions. The cells at 72 hours after infection were fixed in a 10% formalin/PBS (−) solution at room temperature for 20 minutes and then treated with 0.5% Triton X-PBS (−) at room temperature for 10 minutes. Thereafter, an anti-HCV-Core (clone CP14) monoclonal antibody diluted in 5% skimmed milk-PBS (−) (300-fold diluents) were added as a primary antibody and the reaction was allowed to proceed at room temperature for 1 hour. Further, the samples were washed three times with PBS (−), the HRP-labeled goat anti-mouse antibodies (300-fold diluents) were added, and the reaction was allowed to proceed at room temperature for 1 hour. After the samples were washed three times with PBS (−), a Konica immunostain HRP-1000 (Konica Minolta) was added, and the number of blue-stained virus antigen-positive cell populations (also referred to as "immunofocus" or "focus") was counted under a microscope (FIG. 6C).

Based on the amount of Core proteins and the infectivity titer determined, the specific activity (relative specific infectivity) was calculated by the following formula: specific activity=(infectivity titer of culture supernatant)/(amounts of Core proteins in culture supernatant). The results are shown in FIG. 6D.

JFH1-A/WT and JFH1-B/WT exhibited the infectivity titers that are 100 times or more as high and 10 times or more as high as that of the wild-type JFH1wt strain and the JFH1-mut5 strain, respectively, in the Huh7.5.1 cells (FIG. 6C). The results demonstrating the high infectivity of JFH1-A/WT and JFH1-B/WT and enhanced extracellular release of virus proteins indicate that such viruses have released large amounts of infectious virus particles into a culture supernatant. That is, JFH1-A/WT and JFH1-B/WT were found to have the very high capacity for producing infectious virus particles (FIG. 6B and FIG. 6C).

In addition, the specific activity of JFH1-B/WT was found to be significantly high, as shown in FIG. 6D. Such result indicates that JFH1-B/WT has potent infectivity or is capable of forming virus particles very efficiently. Such highly effective capacity for virus particle formation is an excellent property that is advantageous for HCV particle production aimed at vaccine production or other applications.

Example 6

Analysis of Infection Transmission of Adapted Variant Virus

Figure 7:
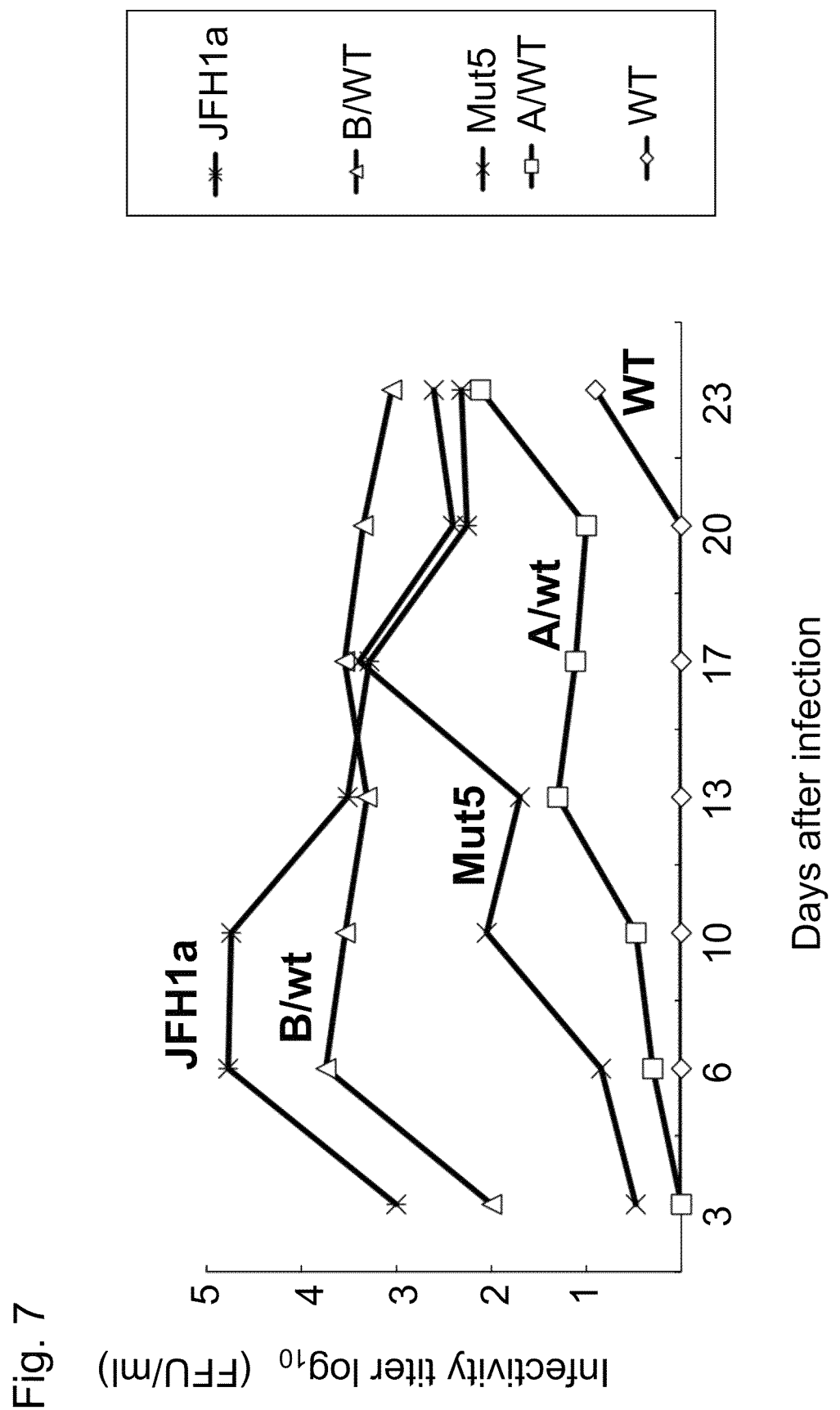
FIG. 7 shows changes over time in the infectivity titers of the wild-type JFH1wt and variants thereof during prolonged culture (prolonged infection). The symbol "*" denotes JFH1a, a open triangle denotes JFH1-B/WT, a cross mark denotes JFH1-Mut5, a square denotes JFH1-A/WT, and a diamond shape denotes JFH1wt.

Subsequently, the capacities of 5 HCV strains (JFH1wt, JFH1a, JFH1-A/WT, JFH1-B/WT, and JFH1-mut5) for infection transmission were analyzed. Huh7.5.1 cells were seeded in a 6-well plate at 1×10$^5$ cells/well 20 to 24 hours before virus infection. The cells were infected with these 5 virus strains at M.O.I. of 0.001 (100 FFU/ml, 1 ml) at 37° C. for 2 hours on the following day. A virus solution was removed 2 hours later, 2 ml of a fresh medium was added, and the cells were continuously cultured at 37° C. for 23 days. About 20% of the cells were collected every 3 or 4 days and subjected to subculture, and a supernatant was collected every time and stored at −80° C. The virus infectivity titer of the collected culture supernatant was determined by the virus titer assay (focus forming assay) described in Example 5. As a result, the virus infectivity titers of JFH1a and JFH1-B/WT were found to rapidly increase after infection, and transmission of infection therewith proceeded rapidly. Thus, these 2 viruses were found to have the high capacity for infection transmission (FIG. 7).

Figure 8:
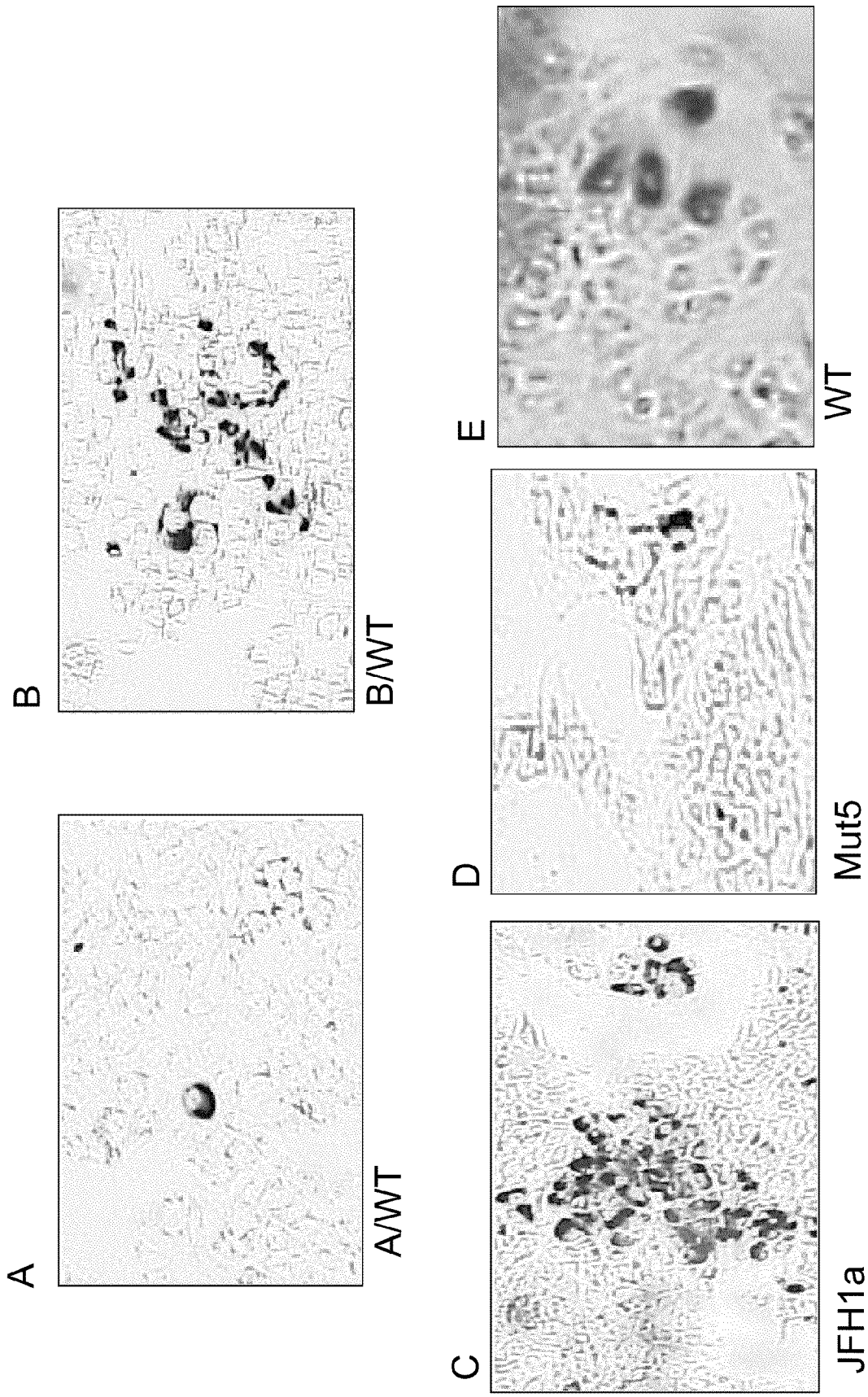
FIG. 8 shows photographs showing sizes of foci formed 72 hours after cell infection with the wild-type JFH1wt and variants thereof. Stained regions are foci. The size of a focus indicates the capacity for transmission of infection.

In order to confirm that JFH1-B/WT has the high capacity for infection transmission, Huh7.5.1 cells (6×10$^3$ cells) were infected with the 5 virus strains (50 FFU each), and sizes of foci formed 72 hours after infection were compared from each other. Foci were stained and observed in accordance with the procedures of the virus titer assay (focus forming assay) described in Example 5. As a result, focus sizes of JFH1a and JFH1-B/WT were found to be particularly larger, and the capacity for infection transmission was found to be particularly high, as shown in FIG. 8.

Example 7

Analysis of Adapted Variant Virus JFH1-B/WT

Regarding the adapted variant virus of JFH1, JFH1-B/WT, having the capacity for high production of viruses and the high capacity for infection transmission, amino acid mutations (amino acid substitutions) at 6 sites thereof were thoroughly analyzed. In general, a point mutation is introduced into a gene via a site-directed mutagenesis method. Variants were prepared with the QuickChange II XL Site-Directed Mutagenesis Kit (Stratagene), according to the accompanying protocols, using a plasmid comprising a cloned full-length genome sequence of JFH1-B/WT or JFH1wt as a template, and primers for introduction of point mutations. The point mutation thus introduced into the HCV genome sequence was verified by sequencing using a DNA sequencer.

Figure 9:
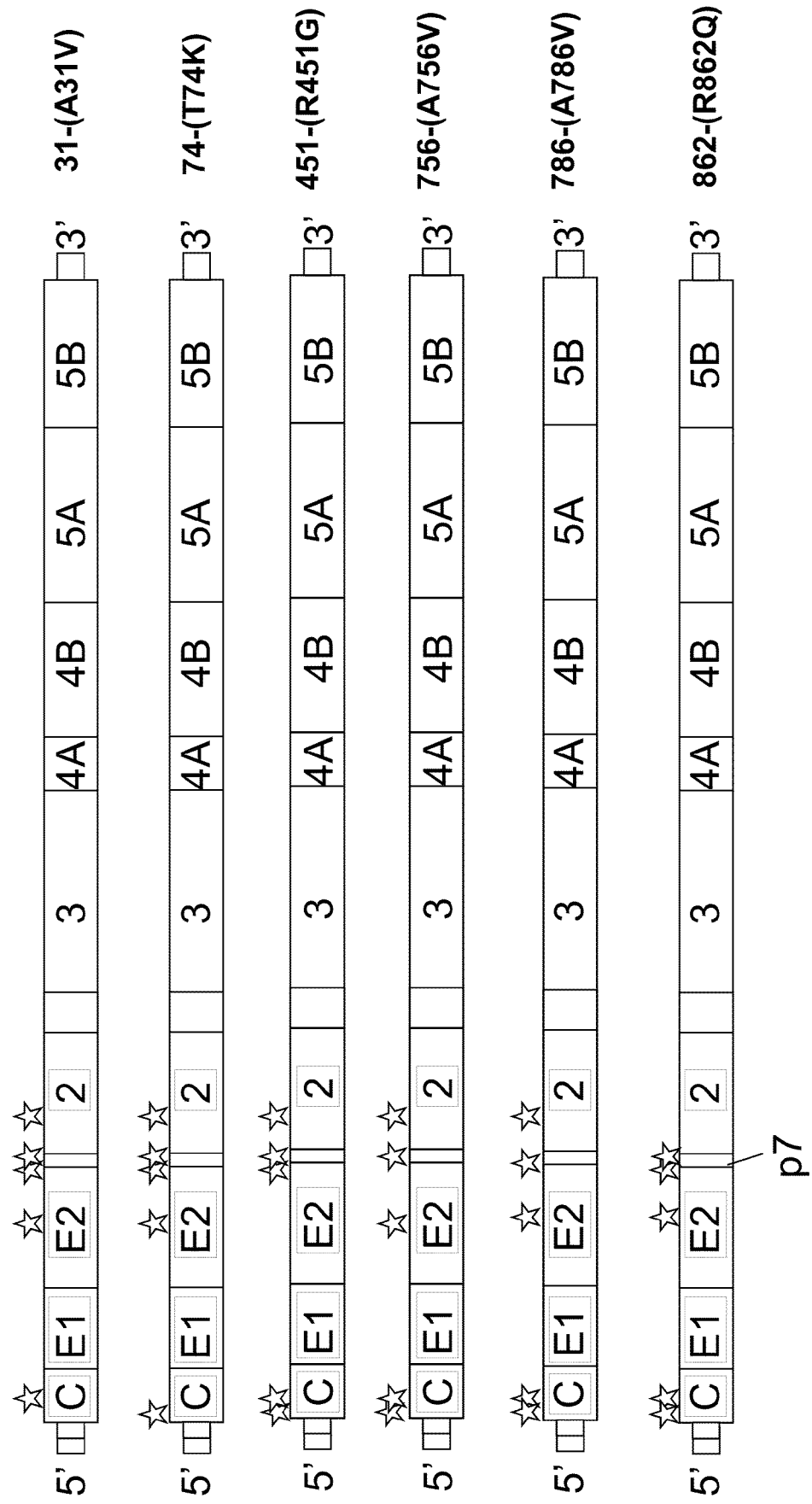
FIG. 9 shows structure diagrams of the full-length HCV genomes (i.e., the polyprotein precursor coding regions and the untranslated regions) of 6 types of variants in which only one out of 6 amino acid mutations in the JFH1-B/WT has been restored to the wild-type amino acid. A star indicates a site in which an amino acid mutation in the JFH1-B/WT is maintained.

FIG. 9 and FIG. 10 show variants in which any one of the amino acid mutations at 6 sites generated in the variant (V31A, K74T, G451R, V756A, V786A, and Q862R) has been restored to the wild-type amino acid; and variants in which any one of such amino acid mutations at 6 sites has been introduced into JFH1wt (wild-type), respectively.

6 types of HCV variants prepared by introducing a nucleotide mutation that restores any one amino acid mutation of the amino acid mutations at 6 sites in JFH1-B/WT to the wild-type amino acid into the JFH1-B/WT full-length genome sequence, were designated as 31-(A31V), 74-(T74K), 451-(R451G), 756-(A756V), 786-(A786V), and 862-(R862Q), respectively (FIG. 9). These variants result from introduction of substitutions indicated below into JFH1-B/W: amino acid substitution A31V (for 31-(A31V)); amino acid substitution T74K (for 74-(T74K)); amino acid substitution R451G (451-(R451 G)); amino acid substitution A756V (for 756-(A756V)); amino acid substitution A786V (for 786-(A786V)); and amino acid substitution R862Q (for 862-(R862Q)). Variant plasmids into which the full-length genome sequences of such variants had been cloned were prepared in the same manner as in Example 4.

Also, 6 types of HCV variants prepared by introducing a nucleotide mutation causing any one of the amino acid mutations at 6 sites of JFH1-B/WT into the full-length genome sequence of the wild-type JFH1wt strain, were designated as 31+(V31A), 74+(K74T), 451+(G451R), 756+(V756A), 786+(V786A), and 862+(Q862R), respectively (FIG. 10). These variants result from introduction of substitutions indicated below into JFH1wt: amino acid substitution V31A (for 31+(V31A)); amino acid substitution K74T (for 74+(K74T)); amino acid substitution G451R (for 451+(G451R)); amino acid substitution V756A (for 756+(V756A)); amino acid substitution V786A (for 786+(V786A)); and amino acid substitution Q862R (862+(Q862R)). Variant plasmids into which the full-length genome sequences of such variants had been cloned were prepared in the same manner as in Example 4.

Further, the variant plasmids prepared were used as templates to synthesize full-length genomic HCV RNA by the method described in Example 1.

Subsequently, full-length genomic HCV RNAs of the 6 types of variant viruses shown in FIG. 9 (31-(A31V), 74-

Figure 11:
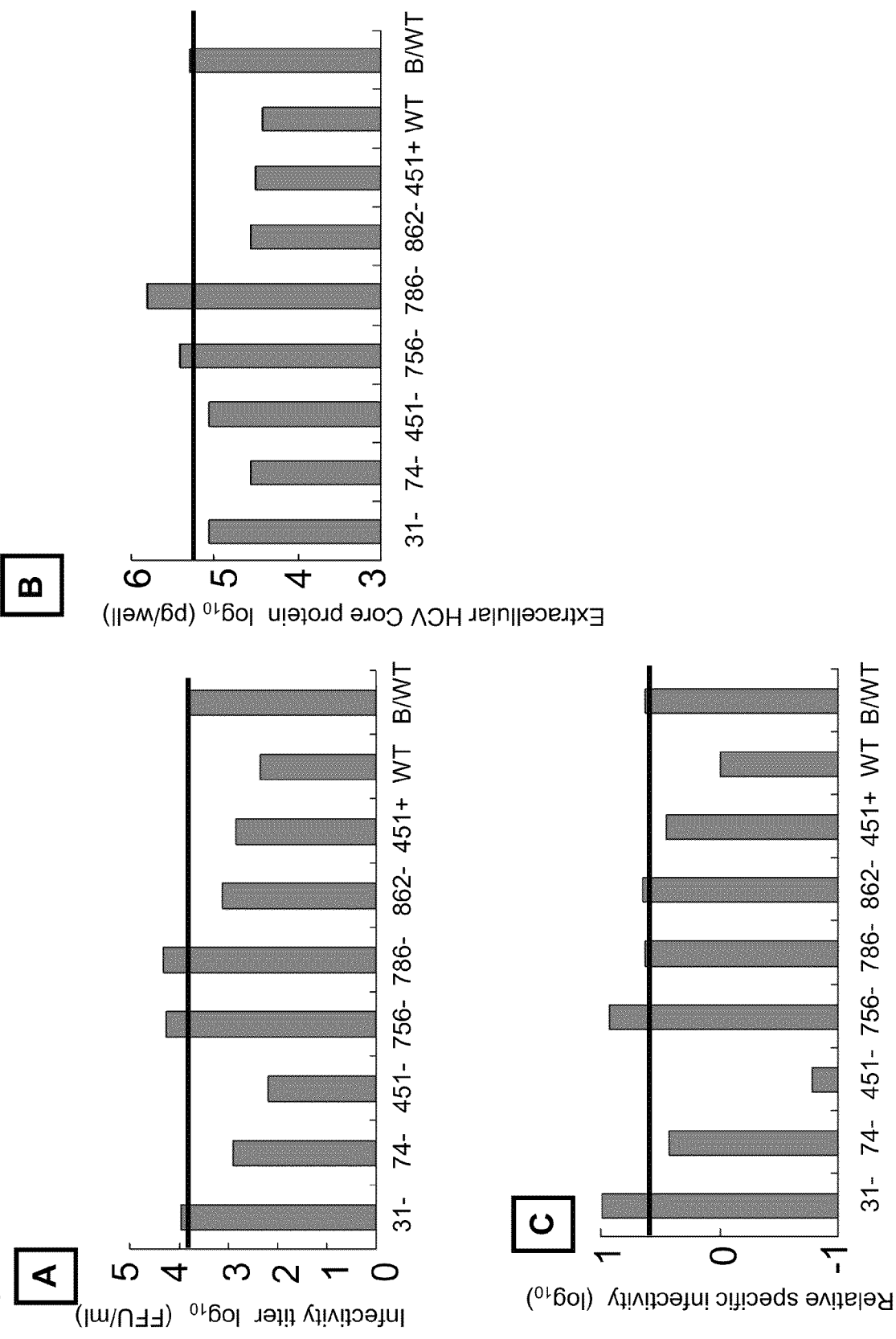
FIG. 11 shows the infectivity titer and the virus production amount of the HCV variants (clones) shown in FIG. 9.

(T74K), 451-(R451G), 756-(A756V), 786-(A786V), and 862-(R862Q)), full-length genomic HCV RNA of the variant virus shown in FIG. 10 451+(G451R), and full-length genomic HCV RNAs of JFH1wt and JFH1-B/WT (4 μg each) were separately transfected into the Huh7.5.1 cells ($1 \times 10^6$ cells) by electroporation in the same manner as in Example 5. The transfected cells were suspended in 10 ml of medium, and the suspension was seeded in a 6-well plate at 2 ml ($2 \times 10^5$ cells)/well. The virus infectivity titer (FFU/ml) and the amount of Core proteins (pg/well) in culture supernatants at 24, 48, 72, and 96 hours after transfection were determined by the methods described in Example 5. FIG. 11 shows the assay results for samples at 72 hours after transfection. As shown in FIGS. 11A, 11B, and 11C, specific activity significantly decreased in the case that the amino acid at position 451 was restored to wild-type G (glycine). The specific activity (relative specific infectivity) was determined by dividing the infectivity titer of the culture supernatant by the amount of Core proteins in the culture supernatant. Potent specific activity indicates the potent infectivity or the capacity for virus particle formation with high efficiency. This demonstrates that the G451R mutation is important for the increase of the infectivity or the capacity for virus particle formation with high efficiency.

Figure 12:
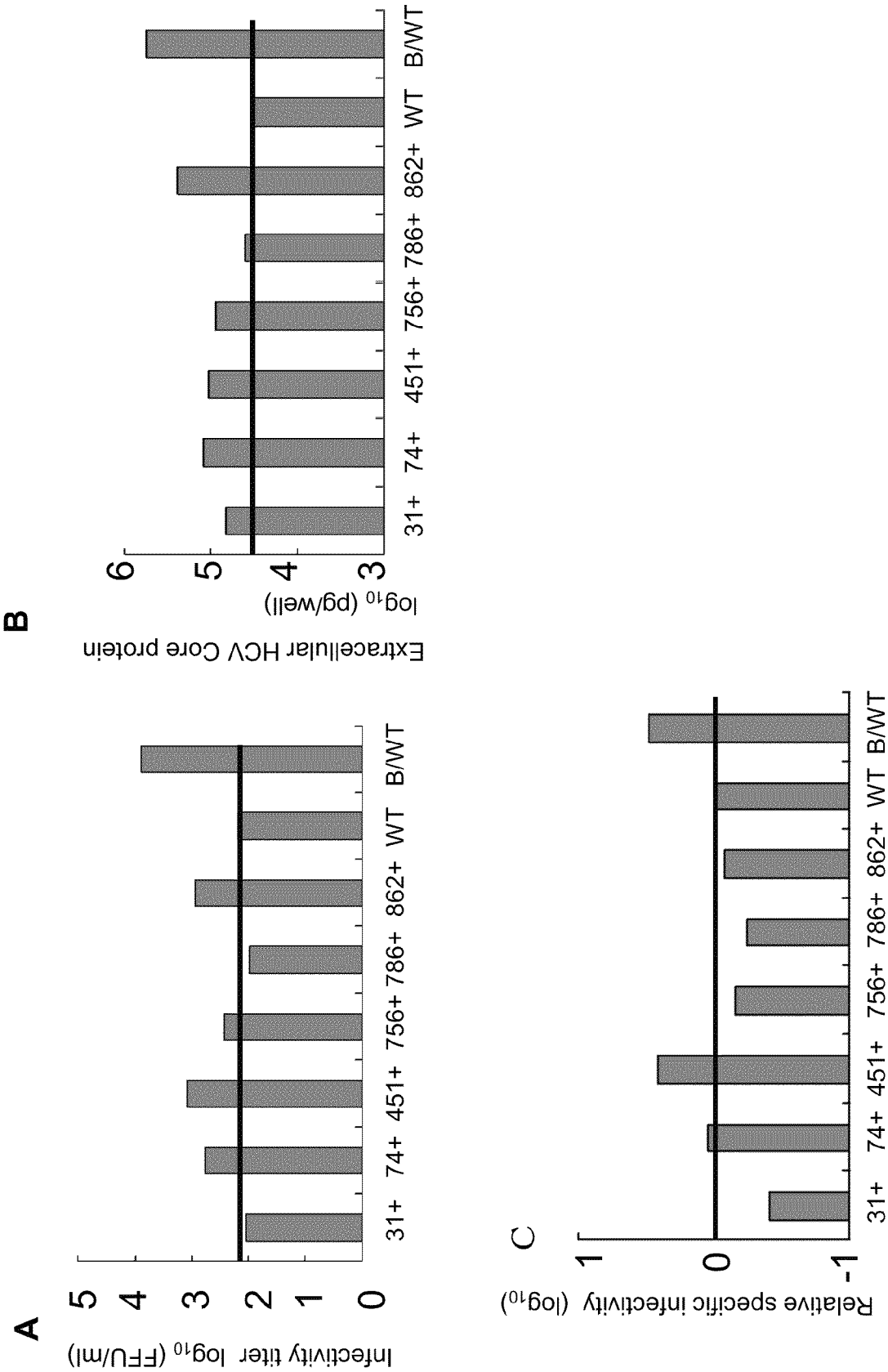
FIG. 12 shows the infectivity titer and the virus production amount of the HCV variants (clones) shown in FIG. 10.

Similarly, full-length genomic HCV RNAs of the 6 types of variant virus strains shown in FIG. 10 (31+(V31A), 74+(K74T), 451+(G451R), 756+(V756A), 786+(V786A), and 862+(Q862R)) and full-length genomic HCV RNAs of JFH1wt and JFH1-B/WT (4 μg each) were separately transfected into the Huh7.5.1 cells ($1 \times 10^6$ cells) by electroporation. The transfected cells were suspended in 10 ml of medium, and the suspension was seeded in a 6-well plate at 2 ml ($2 \times 10^5$ cells)/well. The virus infectivity titer (FFU/ml) and the amount of Core proteins (pg/well) in culture supernatants at 24, 48, 72, and 96 hours after transfection were determined. FIG. 12 shows the assay results for the samples at 72 hours after transfection. The infectivity titers of culture supernatants shows that separate introduction of amino acid mutations, K74T, G451R, and Q862R, into JFH1wt increases the capacity for producing infectious virus particles (FIG. 12A). In addition, the amount of extracellular Core proteins increased to 10 times or more high as that of JFH1wt as a result of introduction of the Q862R mutation (FIG. 12B).

The above assay results show that introduction of the G451R mutation results in the increased virus infectivity and the capacity for producing infectious virus particles, compared with those of JFH1wt. Also, the K74T and Q862R mutations were found to increase the capacity for producing infectious virus particles. However, such mutations were not sufficient to achieve results superior to those of JFH1-B/WT.

Figure 13:
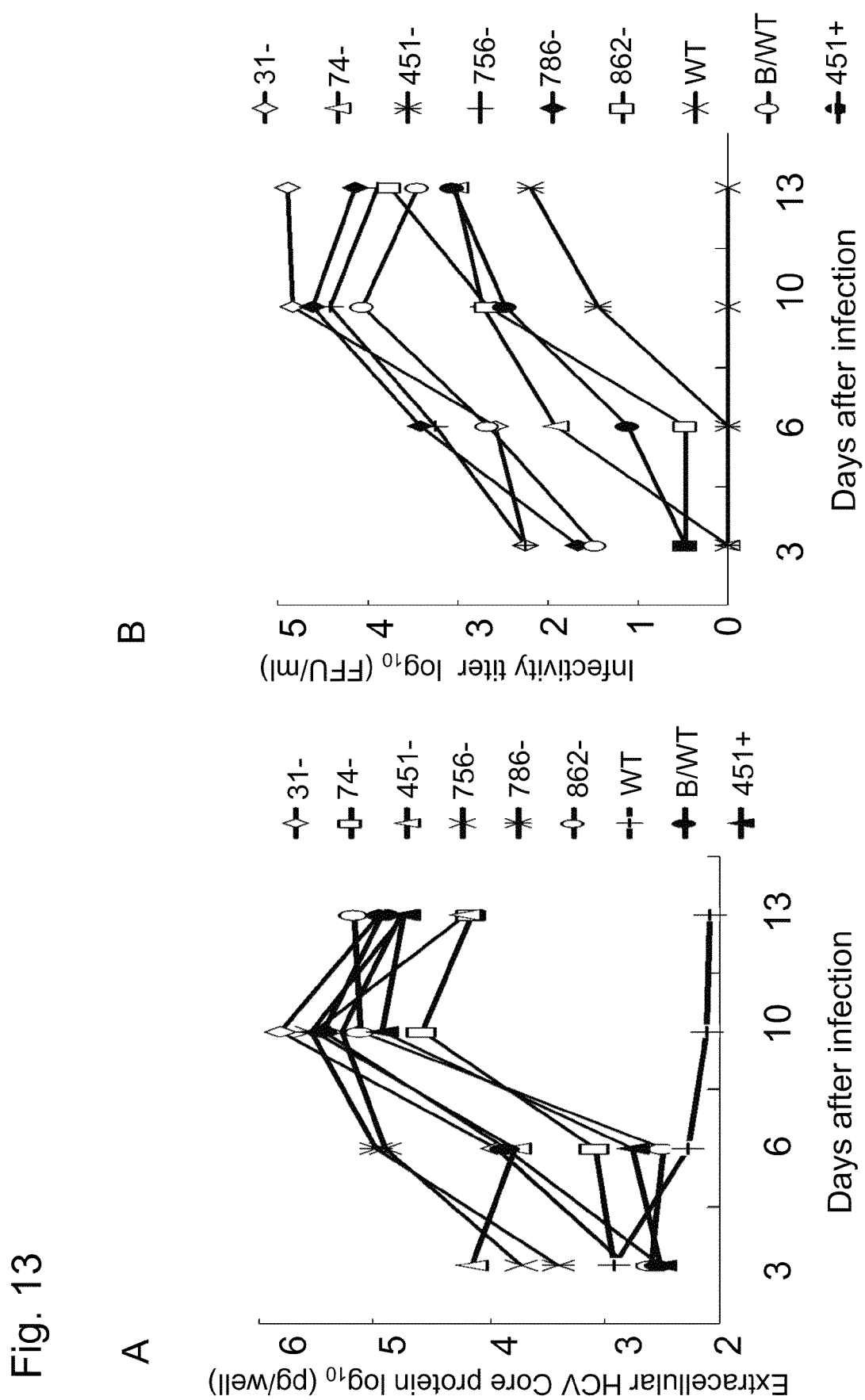
FIG. 13 shows changes over time in the amounts of extracellular Core proteins and the infectivity titers of the HCV variants (clones) shown in FIG. 9 during prolonged culture (prolonged infection). Growth curves of the clones during the prolonged infection are also shown.

In order to examine changes over time in the capacity of virus for infection transmission due to prolonged infection, further, similar experiments as in Example 6 were conducted. The full-length genomic HCV RNAs synthesized from the variant plasmids were transfected into Huh7.5.1 cells, the produced infectious virus particles were allowed to infect the Huh7.5.1 cells at M.O.I. of 0.001, the cells were subjected to prolonged culture with subculturing about 20% of the cells sampled every 3 or 4 days, and the virus production amount and the infectivity titer of the culture supernatant were determined over time. The assay results regarding 31-(A31V), 74-(T74K), 451-(R451G), 756-(A756V), 786-(A786V), 862-(R862Q), 451+(G451R), JFH1wt, and JFH1-B/WT are summarized in FIG. 13. The assay results regarding 31+(V31A), 74+(K74T), 451+(G451R), 756+(V756A), 786+(V786A), 862+(Q862R), JFH1wt, and JFH1-B/WT are summarized in FIG. 14.

As a result, increase of the amount of Core proteins in the culture supernatant was delayed in the variant 451-(R451G), in which the amino acid at position 451 had been restored to wild-type G (glycine) (FIG. 13A). This indicates that the G451R mutation is associated with the capacity for infection transmission. In addition, the infectivity titers of the variant 451-(R451G), in which the amino acid at position 451 was restored to wild-type G (glycine); the variant 74-(T74K), in which amino acid at position 74 was restored to wild-type K (lysine); and the variant 862-(R862Q), in which amino acid at position 862 was restored to wild-type Q (glutamine), were lowered compared with JFH1-B/WT (FIG. 13B).

Figure 14:
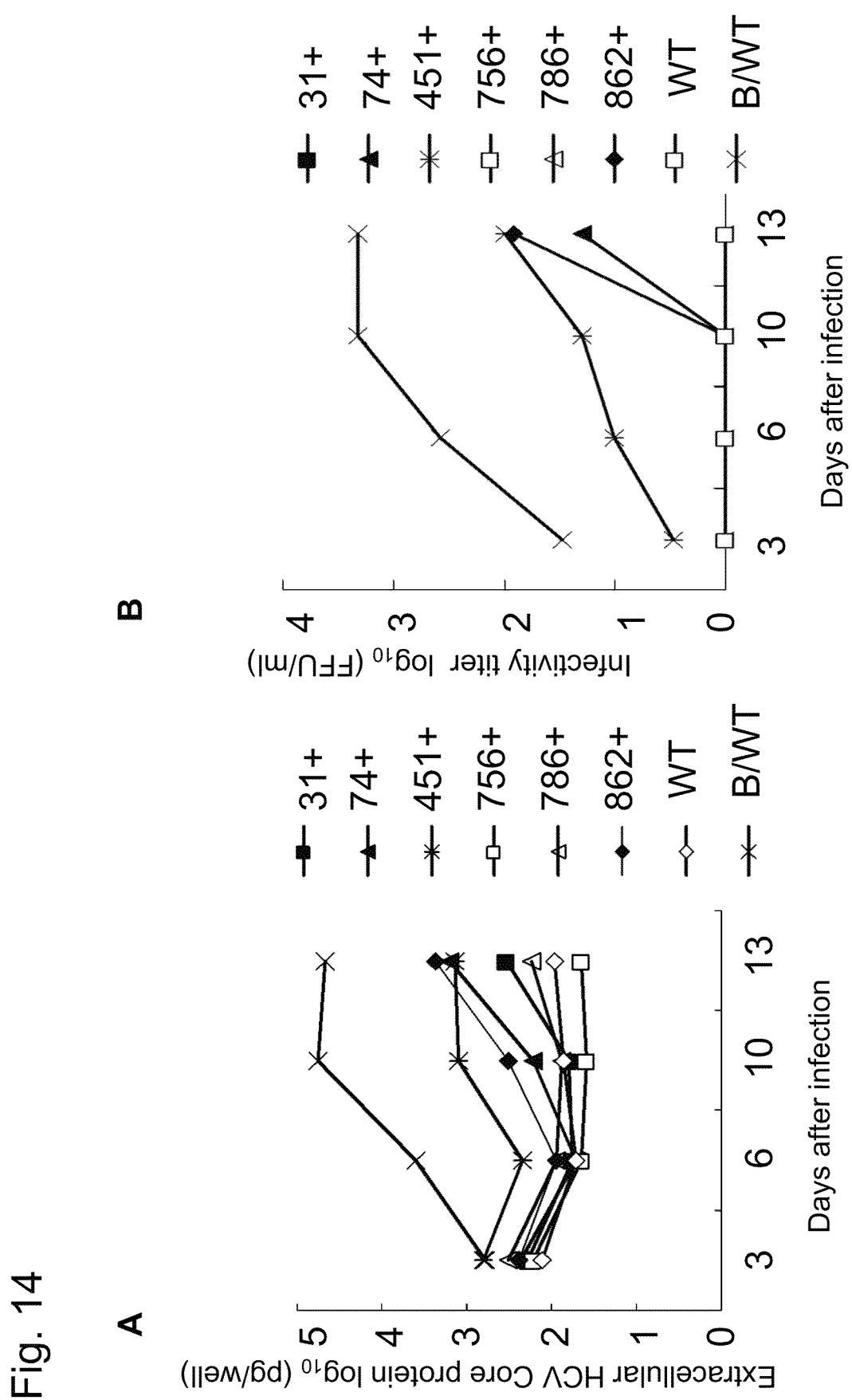
FIG. 14 shows changes over time in the amounts of extracellular Core proteins and the infectivity titers of the HCV variants (clones) shown in FIG. 10 during prolonged culture (prolonged infection). Growth curves of the clones during the prolonged infection are also shown.

As shown in FIG. 14, the patterns in increases in the amount of Core proteins and the infectivity titer of the culture supernatant show that the K74T, G451R, and Q862R mutations contribute to the increase of the capacity for transmission of infection (FIGS. 14A and 14B). In particular, introduction of the G451R mutation results in a significant increase in both the amount of Core proteins and the infectivity titer, compared with JFH1wt. Also, the capacity for producing infectious virus particles significantly increased even in the case of prolonged infection (prolonged culture).

As a result of the analysis above, the K74T, G451R, and Q862R mutations were found to enhance the capacity for HCV production. The full-length genome sequence of the variant 862+(Q862R) (also referred to as "JFH1-Q862R") is shown in SEQ ID NO: 5.

Example 8

Figure 15:
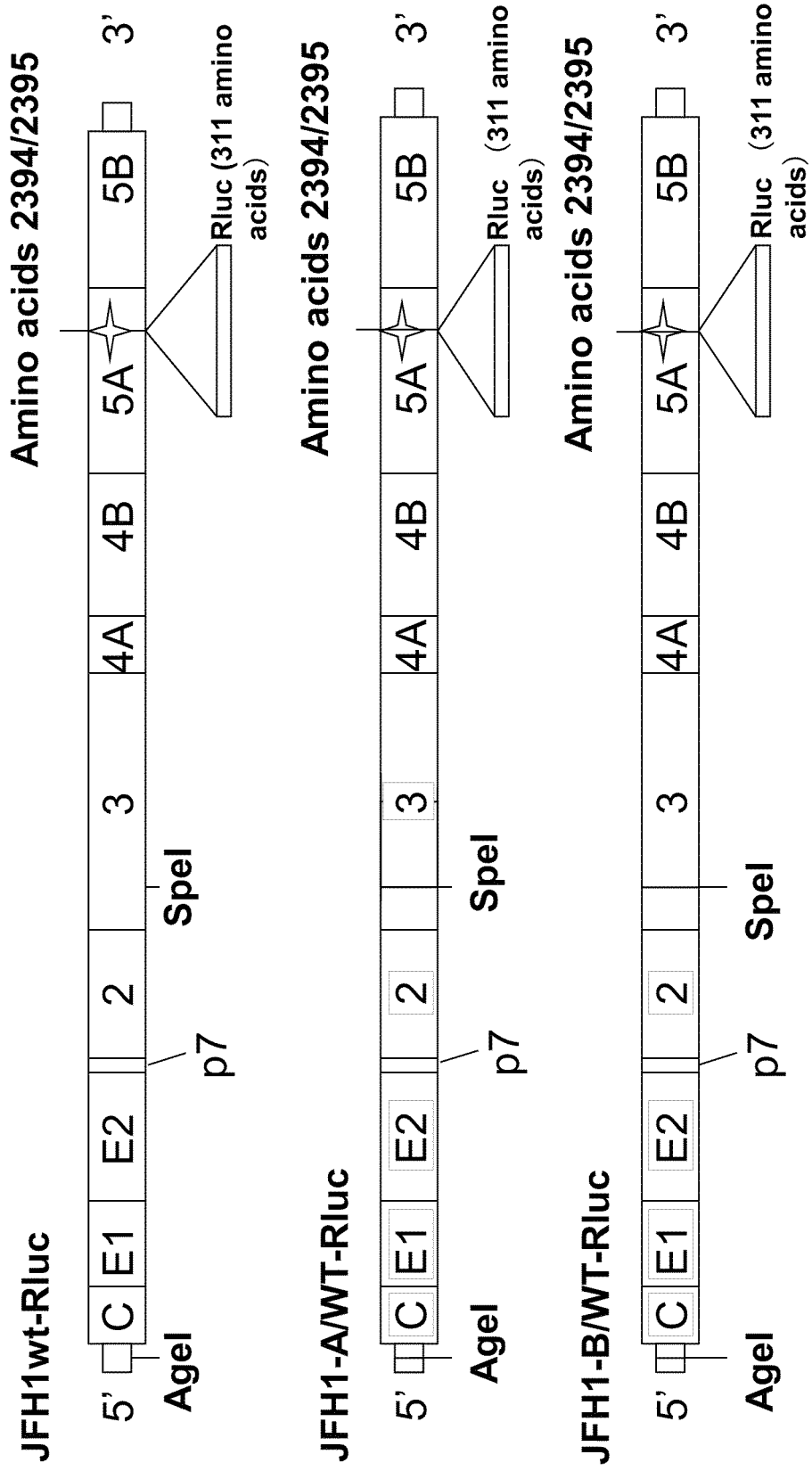
FIG. 15 shows a structural diagram of a replicon prepared by incorporating a reporter gene into the full-length HCV genome sequence. The reporter gene (Rluc) is inserted between amino acids at positions 2394 and 2395 within the polyprotein precursor-coding region (Core to NS5B) of the replicon.

Preparation of Variant Comprising Reporter Gene Incorporated Into Full-Length Genome Sequence In order to easily detect HCV infection and growth, a variant comprising the full-length HCV genome sequence comprising the luciferase gene incorporated therein as a reporter gene was prepared. The structure of the variant prepared is shown in FIG. 15.

Specifically, DNA fragments derived from the full-length genome of JFH1wt (wild-type), and the adapted variants JFH1-A/WT and JFH1-B/WT, which encode an HCV polyprotein precursor comprising *Renilla reniformis* luciferase of 311 amino acids inserted between the amino acid residues at position 2394 (amino acid 2394) and position 2395 (amino acid 2395) as counted from the first amino acid methionine at the N terminus of the HCV polyprotein precursor, was functionally ligated downstream of the T7 promoter to prepare plasmid vectors (pJFH1wt-Rluc, pJFH1-A/WT-Rluc, and pJFH1-B/WT-RLuc) as described below. Incidentally, the above-mentioned insertion site may be specified to be between the amino acids at position 2395 and position 2396, or between the amino acids at position 2396 and position 2397.

At the outset, a *Renilla reniformis* luciferase gene fragment was amplified using the *Renilla reniformis* luciferase gene (SEQ ID NO: 9) inserted into the plasmid pGL4.27 (Promega) as a template and two primers having the XhoI recognition site (ctcgag) at the end: 5'-ctcgagATGGCTTC-CAAGGTGTACGACCCC-3' (SEQ ID NO: 14) and 5'-ctc-gagCTGCTCGTTCTTCAGCACGCGCTC-3' (SEQ ID NO: 15). The amplified gene fragment was digested with XhoI.

The plasmids pJFH-1, pJFH1-A/WT, and pJFH1-B/WT, into which full-length genome sequences of JFH1wt, JFH1-A/WT, and JFH1-B/WT had been cloned, respectively, were digested with AbsI restriction enzyme that recognizes the nucleotide sequence 5'-CCTCGAGG-3' at the site between position 7523 and position 7527 counted from the 5' end, the XhoI-digested fragment of the *Renilla reniformis* luciferase gene amplification product obtained above was inserted and cloned into the restriction site of the plasmids, and then clones having vectors in which *Renilla reniformis* luciferase had been functionally ligated were selected. The thus-obtained variants into which the *Renilla reniformis* luciferase (also be referred to as "Rluc") gene had been introduced are designated as JFH1wt-Rluc, JFH1-A/WT-Rluc, and JFH1-B/WT-Rluc, respectively. The full-length genome sequence of JFH1-A/WT-Rluc (SEQ ID NO: 6), that of JFH1-B/WT-Rluc (SEQ ID NO: 7), and that of JFH1wt-Rluc (SEQ ID NO: 8) cloned into the vectors were verified via sequence determination.

When preparing JFH1wt-Rluc, JFH1-A/WT-Rluc, and JFH1-B/WT-Rluc, as described above, the *Renilla reniformis* luciferase gene (933 bp) with the XhoI recognition sites (ctcgag) added to the 5' end and the 3' end was digested with XhoI, and the gene fragment was inserted into the AbsI cleavage site of pJFH-1, pJFH1-A/WT, or pJFH1-B/WT. In JFH1wt-Rluc, JFH1-A/WT-Rluc, and JFH1-B/WT-Rluc, the *Renilla reniformis* luciferase protein is inserted between the amino acids at position 2394 and position 2395 as counted from first amino acid methionine at the N terminus of the polyprotein precursor of JFH1wt, JFH1-A/WT, or JFH1-B/WT. The insertion site may be specified to be between the amino acids at position 2395 and position 2396, or between the amino acids at position 2396 and position 2397.

Subsequently, the recombinant vector pJFH1wt-Rluc, pJFH1-A/WT-Rluc, or pJFH1-B/WT-RLuc, into which the above-mentioned sequence has been cloned, was digested with XbaI to cleave the insert. After treatment with Mung Bean Nuclease, HCV RNA of the full-length genome sequence was synthesized using the MEGAscript T7 kit (Ambion) and the insert. JFH1wt-Rluc, JFH1-A/WT-Rluc, and JFH1-B/WT-Rluc have 10,617-bp genome sequences comprising the corresponding full-length HCV genome sequence (9,678 bp), 933-bp *Renilla reniformis* luciferase gene, and 6-bp XhoI recognition site (ctcgag) added. The HCV RNAs synthesized from pJFH1wt, pJFH1wt-Rluc, pJFH1-A/WT-Rluc, and pJFH1-B/WT-Rluc were transfected into the Huh7.5.1 cells in the same manner as in Example 5, and the infectivity titers of the culture supernatants were determined 72 hours thereafter. The infectivity titers were determined by staining cells using an anti-HCV-Core (CP14) monoclonal antibody and measuring the number of foci in the same manner as in Example 5.

Figure 16:
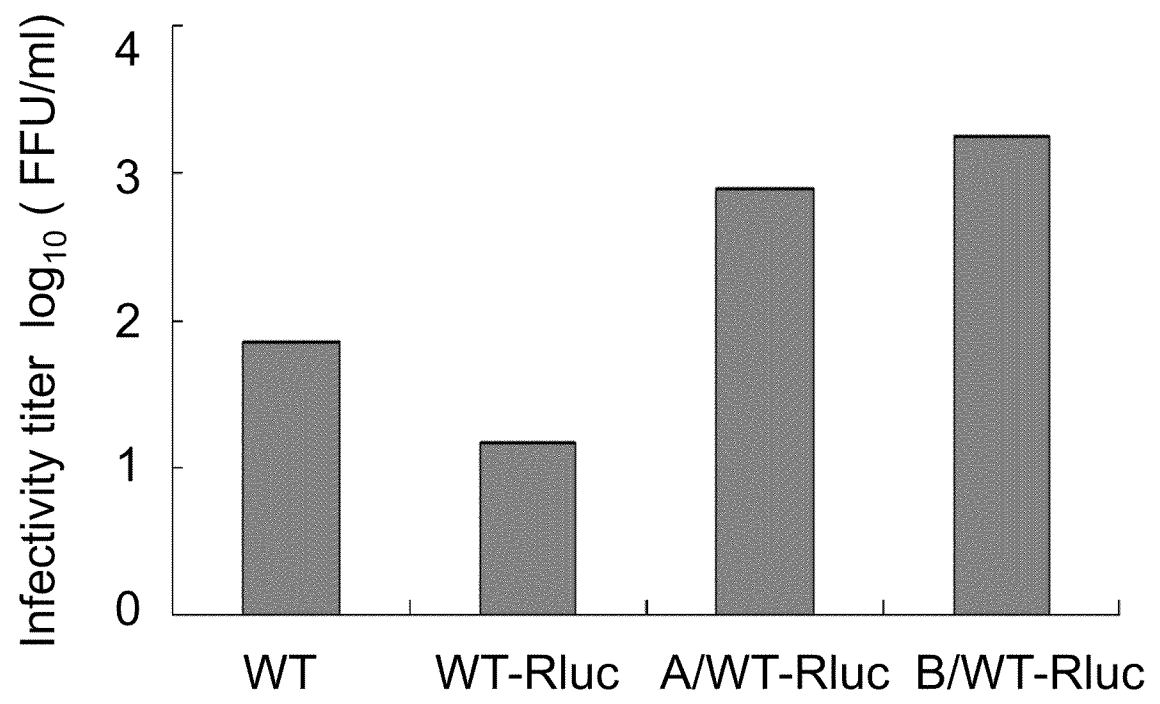

As a result, in the case of the integration of the Rluc gene into the wild-type JFH1wt strain, the capacity for virus production was found to become about 10 times lower than that of the wild-type JFH1wt strain (FIG. 16). In contrast, in the case where the Rluc gene was incorporated into variant JFH1-A/WT or JFH1-B/WT, the infectivity titer was found to be about 100 times or more high as that of JFH1wt-Rluc (FIG. 16).

Figure 17:
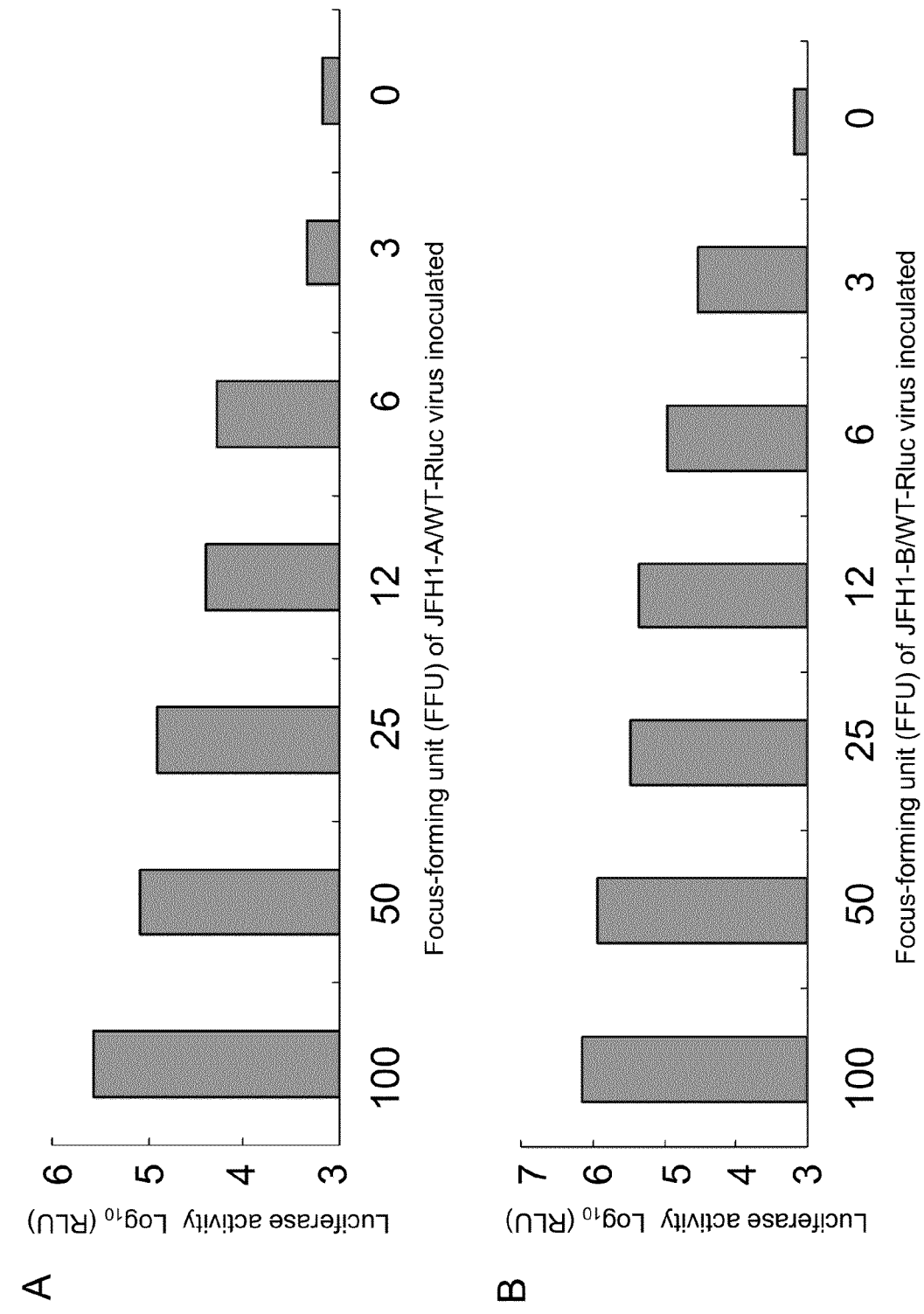
FIG. 17 shows the results of measurement of luciferase activity 72 hours after infection of Huh7.5.1 cells with JFH-A/WT-Rluc (FIG. 17A) and with JFH-B/WT-Rluc (FIG.

Further, the correlation between the amount of HCV particles produced from the full-length genome sequence comprising the Rluc gene incorporated therein and the luciferase activity was analyzed. Huh7.5.1 cells were seeded in a 48-well plate at $1.0 \times 10^4$ cells/well. After 24 hours, the cells were infected for 2 hours with JFH-A/WT-Rluc and JFH-B/WT-Rluc at 100, 50, 25, 12, 6, 3, and 0 FFU (focus-forming unit). The cells were washed twice with PBS (−) after infection, and a fresh medium was added in amounts of 200 μl/well. The cells were collected from the plate 72 hours after virus infection, and luciferase activity was then assayed. Luciferase activity was assayed using the *Renilla Luciferase* Assay System (Promega) in accordance with the accompanying protocols. Specifically, a culture supernatant was removed, the cells were washed twice with 200 μl of PBS (−), 200 μl of a lysis buffer included in the kit (the *Renilla Luciferase* Assay system; Promega) was added, and the mixture was agitated at room temperature for 15 minutes to lyse the cells. 20 μl of the lysate was transferred to a luciferase assay plate, 100 μl of the substrate was added, and the luminescence was assayed using Glomax luminometer (Promega). As a result, luciferase activity correlating with the amount of viruses was detected (FIG. 17).

Example 9

Inhibitory Effects of Interferon on HCV Infection and Growth

Interferon, the inhibitory effects of which on HCV infection and growth are known, was used as a test drug to conduct an experiment for confirming the effectiveness of a screening system for an anti-HCV substance using the JFH1 variant comprising a reporter gene incorporated into the full-length HCV genome sequence (Example 8).

Huh7.5.1 cells were seeded in two 48-well plates at $1.2 \times 10^4$ cells/well 24 hours before virus infection. On the following day, 100 FFU of the viruses JFH-A/WT-Rluc or JFH-B/WT-Rluc were added thereto, and the cells were infected therewith for 2 hours. After infection, the cells were washed twice with PBS (−) and then cultured in a medium supplemented with interferon α (IFN-α) (Universal Type I Interferon; PBL InterferonSource) at the concentrations shown in FIG. 18 (0, 1, 4, 20, or 100 U/ml) for 72 hours. The virus infectivity titer of one of the above two virus-infected plates was determined by the virus titer assay (focus forming assay) as described in Example 5. Luciferase activity of the other plate was assayed by the method described in Example 8. The results are shown in FIG. 18.

Interferon α inhibited HCV infection in a dose-dependent manner (FIG. 18B). As a result of luciferase assays, a strong correlation was observed between the luciferase activity and the infectivity titer (FIG. 18A). The results indicate that the use of JFH1wt or a variant thereof comprising the Rluc gene incorporated therein enables efficient screening for anti-HCV substances, such as interferon, by assaying the infection inhibition rate using luciferase activity as an indicator.

SEQUENCE LISTING FREE TEXT

SEQ ID NOs: 3 to 8: JFH1 variants
SEQ ID NOs: 10 to 18: primers

The invention claimed is:

1. A nucleic acid comprising a sequence encoding a polyprotein precursor of the hepatitis C virus JFH1 strain having one or more amino acid substitutions, wherein the polyprotein precursor comprises at least substitution of glutamine at position 862 with arginine, as determined with reference to the amino acid sequence as shown in SEQ ID NO: 2 in the Sequence Listing.

2. The nucleic acid according to claim 1, comprising the 5'-untranslated region and the 3'-untranslated region of the genome of the hepatitis C virus JFH1 strain.

3. The nucleic acid according to claim 1 or 2, wherein the polyprotein precursor is selected from the group consisting of (a) to (f):
(a) a polyprotein precursor having substitutions of lysine at position 74 with threonine, tyrosine at position 297 with histidine, alanine at position 330 with threonine, serine at position 395 with proline, asparagine at position 417 with serine, aspartic acid at position 483 with glycine, alanine at position 501 with threonine, glutamine at position 862 with arginine, glutamine at position 931 with arginine, and serine at position 961 with alanine, as determined with reference to the amino acid sequence as shown in SEQ ID NO: 2 in the Sequence Listing;
(b) a polyprotein precursor having substitutions of valine at position 31 with alanine, lysine at position 74 with threonine, glycine at position 451 with arginine, valine at position 756 with alanine, valine at position 786 with alanine, and glutamine at position 862 with arginine, as determined with reference to the amino acid sequence as shown in SEQ ID NO: 2 in the Sequence Listing;
(c) a polyprotein precursor having substitutions of lysine at position 74 with threonine, glycine at position 451 with arginine, valine at position 756 with alanine, valine at position 786 with alanine, and glutamine at position 862 with arginine, as determined with reference to the amino acid sequence as shown in SEQ ID NO: 2 in the Sequence Listing;
(d) a polyprotein precursor having substitutions of valine at position 31 with alanine, lysine at position 74 with threonine, glycine at position 451 with arginine, valine at position 786 with alanine, and glutamine at position 862 with arginine, as determined with reference to the amino acid sequence as shown in SEQ ID NO: 2 in the Sequence Listing;
(e) a polyprotein precursor having substitutions of valine at position 31 with alanine, lysine at position 74 with threonine, glycine at position 451 with arginine, valine at position 756 with alanine, and glutamine at position 862 with arginine, as determined with reference to the amino acid sequence as shown in SEQ ID NO: 2 in the Sequence Listing; and
(f) a polyprotein precursor having only one substitution of glutamine at position 862 with arginine, as determined with reference to the amino acid sequence as shown in SEQ ID NO: 2 in the Sequence Listing.

4. The nucleic acid according to claim 2, which consists of the nucleotide sequence as shown in SEQ ID NO: 3, 4, or 5 in the Sequence Listing.

5. The nucleic acid according to claim 1, wherein a nucleic acid encoding a reporter protein is inserted into a region encoding the NS5A protein in the polyprotein precursor.

6. The nucleic acid according to claim 5, wherein the reporter protein is incorporated into the sequence of amino acids at positions 2394 to 2397 of the amino acid sequence as shown in SEQ ID NO: 2 in the Sequence Listing to be translated as a fusion protein.

7. The nucleic acid according to claim 6, which consists of the nucleotide sequence as shown in SEQ ID NO: 6 or 7 in the Sequence Listing.

8. A hepatitis C virus particle which contains the nucleic acid according to claim 1.

9. A cultured cell which produces the hepatitis C virus particle according to claim 8.

10. An immunogenic composition comprising the hepatitis C virus particle according to claim 8.

\* \* \* \* \*

SEQUENCE LISTING

```
<160> NUMBER OF SEQ ID NOS: 18

<210> SEQ ID NO 1
<211> LENGTH: 9678
<212> TYPE: DNA
```

-continued

```
<213> ORGANISM: Hepatitis C virus JFH1 strain
<220> FEATURE:
<221> NAME/KEY: CDS
<222> LOCATION: (341)..(9442)

<400> SEQUENCE: 1
acctgcccct aataggggcg acactccgcc atgaatcact cccctgtgag gaactactgt      60
cttcacgcag aaagcgccta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
cgcttgcgag tgccccggga ggtctcgtag accgtgcacc atg agc aca aat cct      355
                                            Met Ser Thr Asn Pro
                                            1               5 aaa cct caa aga aaa acc aaa aga aac acc aac cgt cgc cca gaa gac      403
Lys Pro Gln Arg Lys Thr Lys Arg Asn Thr Asn Arg Arg Pro Glu Asp
                10                  15                  20 gtt aag ttc ccg ggc ggc ggc cag atc gtt ggc gga gta tac ttg ttg      451
Val Lys Phe Pro Gly Gly Gly Gln Ile Val Gly Gly Val Tyr Leu Leu
            25                  30                  35 ccg cgc agg ggc ccc agg ttg ggt gtg cgc acg aca agg aaa act tcg      499
Pro Arg Arg Gly Pro Arg Leu Gly Val Arg Thr Thr Arg Lys Thr Ser
        40                  45                  50 gag cgg tcc cag cca cgt ggg aga cgc cag ccc atc ccc aaa gat cgg      547
Glu Arg Ser Gln Pro Arg Gly Arg Arg Gln Pro Ile Pro Lys Asp Arg
    55                  60                  65 cgc tcc act ggc aag gcc tgg gga aaa cca ggt cgc ccc tgg ccc cta      595
Arg Ser Thr Gly Lys Ala Trp Gly Lys Pro Gly Arg Pro Trp Pro Leu
70                  75                  80                  85 tat ggg aat gag gga ctc ggc tgg gca gga tgg ctc ctg tcc ccc cga      643
Tyr Gly Asn Glu Gly Leu Gly Trp Ala Gly Trp Leu Leu Ser Pro Arg
                90                  95                  100 ggc tct cgc ccc tcc tgg ggc ccc act gac ccc cgg cat agg tcg cgc      691
Gly Ser Arg Pro Ser Trp Gly Pro Thr Asp Pro Arg His Arg Ser Arg
            105                 110                 115 aac gtg ggt aaa gtc atc gac acc cta acg tgt ggc ttt gcc gac ctc      739
Asn Val Gly Lys Val Ile Asp Thr Leu Thr Cys Gly Phe Ala Asp Leu
        120                 125                 130 atg ggg tac atc ccc gtc gta ggc gcc ccg ctt agt ggc gcc gcc aga      787
Met Gly Tyr Ile Pro Val Val Gly Ala Pro Leu Ser Gly Ala Ala Arg
    135                 140                 145 gct gtc gcg cac ggc gtg aga gtc ctg gag gac ggg gtt aat tat gca      835
Ala Val Ala His Gly Val Arg Val Leu Glu Asp Gly Val Asn Tyr Ala
150                 155                 160                 165 aca ggg aac cta ccc ggt ttc ccc ttt tct atc ttc ttg ctg gcc ctg      883
Thr Gly Asn Leu Pro Gly Phe Pro Phe Ser Ile Phe Leu Leu Ala Leu
                170                 175                 180 ttg tcc tgc atc acc gtt ccg gtc tct gct gcc cag gtg aag aat acc      931
Leu Ser Cys Ile Thr Val Pro Val Ser Ala Ala Gln Val Lys Asn Thr
            185                 190                 195 agt agc agc tac atg gtg acc aat gac tgc tcc aat gac agc atc act      979
Ser Ser Ser Tyr Met Val Thr Asn Asp Cys Ser Asn Asp Ser Ile Thr
        200                 205                 210 tgg cag ctc gag gct gcg gtt ctc cac gtc ccc ggg tgc gtc ccg tgc     1027
Trp Gln Leu Glu Ala Ala Val Leu His Val Pro Gly Cys Val Pro Cys
    215                 220                 225 gag aga gtg ggg aat acg tca cgg tgt tgg gtg cca gtc tcg cca aac     1075
Glu Arg Val Gly Asn Thr Ser Arg Cys Trp Val Pro Val Ser Pro Asn
```

| | | | | | | | | | | | | | | | |
|---|---|---|---|---|---|---|---|---|---|---|---|---|---|---|---|
| 230 | | | | | 235 | | | | | 240 | | | | | 245 |

```
atg gct gtg cgg cag ccc ggt gcc ctc acg cag ggt ctg cgg acg cac      1123
Met Ala Val Arg Gln Pro Gly Ala Leu Thr Gln Gly Leu Arg Thr His
                250                 255                 260 atc gat atg gtt gtg atg tcc gcc acc ttc tgc tct gct ctc tac gtg      1171
Ile Asp Met Val Val Met Ser Ala Thr Phe Cys Ser Ala Leu Tyr Val
                265                 270                 275 ggg gac ctc tgt ggc ggg gtg atg ctc gcg gcc cag gtg ttc atc gtc      1219
Gly Asp Leu Cys Gly Gly Val Met Leu Ala Ala Gln Val Phe Ile Val
                280                 285                 290 tcg ccg cag tac cac tgg ttt gtg caa gaa tgc aat tgc tcc atc tac      1267
Ser Pro Gln Tyr His Trp Phe Val Gln Glu Cys Asn Cys Ser Ile Tyr
295                 300                 305 cct ggc acc atc act gga cac cgc atg gca tgg gac atg atg atg aac      1315
Pro Gly Thr Ile Thr Gly His Arg Met Ala Trp Asp Met Met Met Asn
310                 315                 320                 325 tgg tcg ccc acg gcc acc atg atc ctg gcg tac gtg atg cgc gtc ccc      1363
Trp Ser Pro Thr Ala Thr Met Ile Leu Ala Tyr Val Met Arg Val Pro
                330                 335                 340 gag gtc atc ata gac atc gtt agc ggg gct cac tgg ggc gtc atg ttc      1411
Glu Val Ile Ile Asp Ile Val Ser Gly Ala His Trp Gly Val Met Phe
                345                 350                 355 ggc ttg gcc tac ttc tct atg cag gga gcg tgg gcg aag gtc att gtc      1459
Gly Leu Ala Tyr Phe Ser Met Gln Gly Ala Trp Ala Lys Val Ile Val
                360                 365                 370 atc ctt ctg ctg gcc gct ggg gtg gac gcg ggc acc acc acc gtt gga      1507
Ile Leu Leu Leu Ala Ala Gly Val Asp Ala Gly Thr Thr Thr Val Gly
                375                 380                 385 ggc gct gtt gca cgt tcc acc aac gtg att gcc ggc gtg ttc agc cat      1555
Gly Ala Val Ala Arg Ser Thr Asn Val Ile Ala Gly Val Phe Ser His
390                 395                 400                 405 ggc cct cag cag aac att cag ctc att aac acc aac ggc agt tgg cac      1603
Gly Pro Gln Gln Asn Ile Gln Leu Ile Asn Thr Asn Gly Ser Trp His
                410                 415                 420 atc aac cgt act gcc ttg aat tgc aat gac tcc ttg aac acc ggc ttt      1651
Ile Asn Arg Thr Ala Leu Asn Cys Asn Asp Ser Leu Asn Thr Gly Phe
                425                 430                 435 ctc gcg gcc ttg ttc tac acc aac cgc ttt aac tcg tca ggg tgt cca      1699
Leu Ala Ala Leu Phe Tyr Thr Asn Arg Phe Asn Ser Ser Gly Cys Pro
                440                 445                 450 ggg cgc ctg tcc gcc tgc cgc aac atc gag gct ttc cgg ata ggg tgg      1747
Gly Arg Leu Ser Ala Cys Arg Asn Ile Glu Ala Phe Arg Ile Gly Trp
455                 460                 465 ggc acc cta cag tac gag gat aat gtc acc aat cca gag gat atg agg      1795
Gly Thr Leu Gln Tyr Glu Asp Asn Val Thr Asn Pro Glu Asp Met Arg
470                 475                 480                 485 ccg tac tgc tgg cac tac ccc cca aag ccg tgt ggc gta gtc ccc gcg      1843
Pro Tyr Cys Trp His Tyr Pro Pro Lys Pro Cys Gly Val Val Pro Ala
                490                 495                 500 agg tct gtg tgt ggc cca gtg tac tgt ttc acc ccc agc ccg gta gta      1891
Arg Ser Val Cys Gly Pro Val Tyr Cys Phe Thr Pro Ser Pro Val Val
                505                 510                 515 gtg ggc acg acc gac aga cgt gga gtg ccc acc tac aca tgg gga gag      1939
Val Gly Thr Thr Asp Arg Arg Gly Val Pro Thr Tyr Thr Trp Gly Glu
                520                 525                 530 aat gag aca gat gtc ttc cta ctg aac agc acc cga ccg ccg cag ggc      1987
Asn Glu Thr Asp Val Phe Leu Leu Asn Ser Thr Arg Pro Pro Gln Gly
535                 540                 545 tca tgg ttc ggc tgc acg tgg atg aac tcc act ggt ttc acc aag act      2035
```

```
Ser Trp Phe Gly Cys Thr Trp Met Asn Ser Thr Gly Phe Thr Lys Thr
550                 555                 560                 565 tgt ggc gcg cca cct tgc cgc acc aga gct gac ttc aac gcc agc acg    2083
Cys Gly Ala Pro Pro Cys Arg Thr Arg Ala Asp Phe Asn Ala Ser Thr
                    570                 575                 580 gac ttg ttg tgc cct acg gat tgt ttt agg aag cat cct gat gcc act    2131
Asp Leu Leu Cys Pro Thr Asp Cys Phe Arg Lys His Pro Asp Ala Thr
                585                 590                 595 tat att aag tgt ggt tct ggg ccc tgg ctc aca cca aag tgc ctg gtc    2179
Tyr Ile Lys Cys Gly Ser Gly Pro Trp Leu Thr Pro Lys Cys Leu Val
            600                 605                 610 cac tac cct tac aga ctc tgg cat tac ccc tgc aca gtc aat ttt acc    2227
His Tyr Pro Tyr Arg Leu Trp His Tyr Pro Cys Thr Val Asn Phe Thr
            615                 620                 625 atc ttc aag ata aga atg tat gta ggg ggg gtt gag cac agg ctc acg    2275
Ile Phe Lys Ile Arg Met Tyr Val Gly Gly Val Glu His Arg Leu Thr
630                 635                 640                 645 gcc gca tgc aac ttc act cgt ggg gat cgc tgc gac ttg gag gac agg    2323
Ala Ala Cys Asn Phe Thr Arg Gly Asp Arg Cys Asp Leu Glu Asp Arg
                650                 655                 660 gac agg agt cag ctg tct cct ctg ttg cac tct acc acg gaa tgg gcc    2371
Asp Arg Ser Gln Leu Ser Pro Leu Leu His Ser Thr Thr Glu Trp Ala
                665                 670                 675 atc ctg ccc tgc acc tac tca gac tta ccc gct ttg tca act ggt ctt    2419
Ile Leu Pro Cys Thr Tyr Ser Asp Leu Pro Ala Leu Ser Thr Gly Leu
            680                 685                 690 ctc cac ctt cac cag aac atc gtg gac gta caa tac atg tat ggc ctc    2467
Leu His Leu His Gln Asn Ile Val Asp Val Gln Tyr Met Tyr Gly Leu
            695                 700                 705 tca cct gct atc aca aaa tac gtc gtt cga tgg gag tgg gtg gta ctc    2515
Ser Pro Ala Ile Thr Lys Tyr Val Val Arg Trp Glu Trp Val Val Leu
710                 715                 720                 725 tta ttc ctg ctc tta gcg gac gcc aga gtc tgc gcc tgc ttg tgg atg    2563
Leu Phe Leu Leu Leu Ala Asp Ala Arg Val Cys Ala Cys Leu Trp Met
                730                 735                 740 ctc atc ttg ttg ggc cag gcc gaa gca gca ttg gag aag ttg gtc gtc    2611
Leu Ile Leu Leu Gly Gln Ala Glu Ala Ala Leu Glu Lys Leu Val Val
                745                 750                 755 ttg cac gct gcg agt gcg gct aac tgc cat ggc ctc cta tat ttt gcc    2659
Leu His Ala Ala Ser Ala Ala Asn Cys His Gly Leu Leu Tyr Phe Ala
                760                 765                 770 atc ttc ttc gtg gca gct tgg cac atc agg ggt cgg gtg gtc ccc ttg    2707
Ile Phe Phe Val Ala Ala Trp His Ile Arg Gly Arg Val Val Pro Leu
775                 780                 785 acc acc tat tgc ctc act ggc cta tgg ccc ttc tgc cta ctg ctc atg    2755
Thr Thr Tyr Cys Leu Thr Gly Leu Trp Pro Phe Cys Leu Leu Leu Met
790                 795                 800                 805 gca ctg ccc cgg cag gct tat gcc tat gac gca cct gtg cac gga cag    2803
Ala Leu Pro Arg Gln Ala Tyr Ala Tyr Asp Ala Pro Val His Gly Gln
                810                 815                 820 ata ggc gtg ggt ttg ttg ata ttg atc acc ctc ttc aca ctc acc ccg    2851
Ile Gly Val Gly Leu Leu Ile Leu Ile Thr Leu Phe Thr Leu Thr Pro
            825                 830                 835 ggg tat aag acc ctc ctc ggc cag tgt ctg tgg tgg ttg tgc tat ctc    2899
Gly Tyr Lys Thr Leu Leu Gly Gln Cys Leu Trp Trp Leu Cys Tyr Leu
            840                 845                 850 ctg acc ctg ggg gaa gcc atg att cag gag tgg gta cca ccc atg cag    2947
Leu Thr Leu Gly Glu Ala Met Ile Gln Glu Trp Val Pro Pro Met Gln
855                 860                 865
```

| | | | | | | | | | | | | | | | | |
|---|---|---|---|---|---|---|---|---|---|---|---|---|---|---|---|---|
| gtg | cgc | ggc | ggc | cgc | gat | ggc | atc | gcg | tgg | gcc | gtc | act | ata | ttc | tgc | 2995 |
| Val | Arg | Gly | Gly | Arg | Asp | Gly | Ile | Ala | Trp | Ala | Val | Thr | Ile | Phe | Cys | |
| 870 | | | | 875 | | | | 880 | | | | | 885 | | | |

| | | | | | | | | | | | | | | | | |
|---|---|---|---|---|---|---|---|---|---|---|---|---|---|---|---|---|
| ccg | ggt | gtg | gtg | ttt | gac | att | acc | aaa | tgg | ctt | ttg | gcg | ttg | ctt | ggg | 3043 |
| Pro | Gly | Val | Val | Phe | Asp | Ile | Thr | Lys | Trp | Leu | Leu | Ala | Leu | Leu | Gly | |
| | | | 890 | | | | | 895 | | | | | 900 | | | |

| | | | | | | | | | | | | | | | | |
|---|---|---|---|---|---|---|---|---|---|---|---|---|---|---|---|---|
| cct | gct | tac | ctc | tta | agg | gcc | gct | ttg | aca | cat | gtg | ccg | tac | ttc | gtc | 3091 |
| Pro | Ala | Tyr | Leu | Leu | Arg | Ala | Ala | Leu | Thr | His | Val | Pro | Tyr | Phe | Val | |
| | | | | 905 | | | | | 910 | | | | | 915 | | |

| | | | | | | | | | | | | | | | | |
|---|---|---|---|---|---|---|---|---|---|---|---|---|---|---|---|---|
| aga | gct | cac | gct | ctg | ata | agg | gta | tgc | gct | ttg | gtg | aag | cag | ctc | gcg | 3139 |
| Arg | Ala | His | Ala | Leu | Ile | Arg | Val | Cys | Ala | Leu | Val | Lys | Gln | Leu | Ala | |
| | 920 | | | | | 925 | | | | | 930 | | | | | |

| | | | | | | | | | | | | | | | | |
|---|---|---|---|---|---|---|---|---|---|---|---|---|---|---|---|---|
| ggg | ggt | agg | tat | gtt | cag | gtg | gcg | cta | ttg | gcc | ctt | ggc | agg | tgg | act | 3187 |
| Gly | Gly | Arg | Tyr | Val | Gln | Val | Ala | Leu | Leu | Ala | Leu | Gly | Arg | Trp | Thr | |
| | | 935 | | | | | 940 | | | | | 945 | | | | |

| | | | | | | | | | | | | | | | | |
|---|---|---|---|---|---|---|---|---|---|---|---|---|---|---|---|---|
| ggc | acc | tac | atc | tat | gac | cac | ctc | aca | cct | atg | tcg | gac | tgg | gcc | gct | 3235 |
| Gly | Thr | Tyr | Ile | Tyr | Asp | His | Leu | Thr | Pro | Met | Ser | Asp | Trp | Ala | Ala | |
| 950 | | | | 955 | | | | | 960 | | | | | 965 | | |

| | | | | | | | | | | | | | | | | |
|---|---|---|---|---|---|---|---|---|---|---|---|---|---|---|---|---|
| agc | ggc | ctg | cgc | gac | tta | gcg | gtc | gcc | gtg | gaa | ccc | atc | atc | ttc | agt | 3283 |
| Ser | Gly | Leu | Arg | Asp | Leu | Ala | Val | Ala | Val | Glu | Pro | Ile | Ile | Phe | Ser | |
| | | | | 970 | | | | | 975 | | | | | 980 | | |

| | | | | | | | | | | | | | | | | |
|---|---|---|---|---|---|---|---|---|---|---|---|---|---|---|---|---|
| ccg | atg | gag | aag | aag | gtc | atc | gtc | tgg | gga | gcg | gag | acg | gct | gca | tgt | 3331 |
| Pro | Met | Glu | Lys | Lys | Val | Ile | Val | Trp | Gly | Ala | Glu | Thr | Ala | Ala | Cys | |
| | | | 985 | | | | | 990 | | | | | 995 | | | |

| | | | | | | | | | | | | | | |
|---|---|---|---|---|---|---|---|---|---|---|---|---|---|---|---|
| ggg | gac | att | cta | cat | gga | ctt | ccc | gtg | tcc | gcc | cga | ctc | ggc | cag | 3376 |
| Gly | Asp | Ile | Leu | His | Gly | Leu | Pro | Val | Ser | Ala | Arg | Leu | Gly | Gln | |
| | | 1000 | | | | | 1005 | | | | | 1010 | | | |

| | | | | | | | | | | | | | | |
|---|---|---|---|---|---|---|---|---|---|---|---|---|---|---|---|
| gag | atc | ctc | ctc | ggc | cca | gct | gat | ggc | tac | acc | tcc | aag | ggg | tgg | 3421 |
| Glu | Ile | Leu | Leu | Gly | Pro | Ala | Asp | Gly | Tyr | Thr | Ser | Lys | Gly | Trp | |
| | | 1015 | | | | | 1020 | | | | | 1025 | | | |

| | | | | | | | | | | | | | | |
|---|---|---|---|---|---|---|---|---|---|---|---|---|---|---|---|
| aag | ctc | ctt | gct | ccc | atc | act | gct | tat | gcc | cag | caa | aca | cga | ggc | 3466 |
| Lys | Leu | Leu | Ala | Pro | Ile | Thr | Ala | Tyr | Ala | Gln | Gln | Thr | Arg | Gly | |
| | | | 1030 | | | | | 1035 | | | | | 1040 | | |

| | | | | | | | | | | | | | | |
|---|---|---|---|---|---|---|---|---|---|---|---|---|---|---|---|
| ctc | ctg | ggc | gcc | ata | gtg | gtg | agt | atg | acg | ggg | cgt | gac | agg | aca | 3511 |
| Leu | Leu | Gly | Ala | Ile | Val | Val | Ser | Met | Thr | Gly | Arg | Asp | Arg | Thr | |
| | | | 1045 | | | | | 1050 | | | | | 1055 | | |

| | | | | | | | | | | | | | | |
|---|---|---|---|---|---|---|---|---|---|---|---|---|---|---|---|
| gaa | cag | gcc | ggg | gaa | gtc | caa | atc | ctg | tcc | aca | gtc | tct | cag | tcc | 3556 |
| Glu | Gln | Ala | Gly | Glu | Val | Gln | Ile | Leu | Ser | Thr | Val | Ser | Gln | Ser | |
| | 1060 | | | | | 1065 | | | | | 1070 | | | | |

| | | | | | | | | | | | | | | |
|---|---|---|---|---|---|---|---|---|---|---|---|---|---|---|---|
| ttc | ctc | gga | aca | acc | atc | tcg | ggg | gtt | ttg | tgg | act | gtt | tac | cac | 3601 |
| Phe | Leu | Gly | Thr | Thr | Ile | Ser | Gly | Val | Leu | Trp | Thr | Val | Tyr | His | |
| | | 1075 | | | | | 1080 | | | | | 1085 | | | |

| | | | | | | | | | | | | | | |
|---|---|---|---|---|---|---|---|---|---|---|---|---|---|---|---|
| gga | gct | ggc | aac | aag | act | cta | gcc | ggc | tta | cgg | ggt | ccg | gtc | acg | 3646 |
| Gly | Ala | Gly | Asn | Lys | Thr | Leu | Ala | Gly | Leu | Arg | Gly | Pro | Val | Thr | |
| | | 1090 | | | | | 1095 | | | | | 1100 | | | |

| | | | | | | | | | | | | | | |
|---|---|---|---|---|---|---|---|---|---|---|---|---|---|---|---|
| cag | atg | tac | tcg | agt | gct | gag | ggg | gac | ttg | gta | ggc | tgg | ccc | agc | 3691 |
| Gln | Met | Tyr | Ser | Ser | Ala | Glu | Gly | Asp | Leu | Val | Gly | Trp | Pro | Ser | |
| | | 1105 | | | | | 1110 | | | | | 1115 | | | |

| | | | | | | | | | | | | | | |
|---|---|---|---|---|---|---|---|---|---|---|---|---|---|---|---|
| ccc | cct | ggg | acc | aag | tct | ttg | gag | ccg | tgc | aag | tgt | gga | gcc | gtc | 3736 |
| Pro | Pro | Gly | Thr | Lys | Ser | Leu | Glu | Pro | Cys | Lys | Cys | Gly | Ala | Val | |
| | | 1120 | | | | | 1125 | | | | | 1130 | | | |

| | | | | | | | | | | | | | | |
|---|---|---|---|---|---|---|---|---|---|---|---|---|---|---|---|
| gac | cta | tat | ctg | gtc | acg | cgg | aac | gct | gat | gtc | atc | ccg | gct | cgg | 3781 |
| Asp | Leu | Tyr | Leu | Val | Thr | Arg | Asn | Ala | Asp | Val | Ile | Pro | Ala | Arg | |
| | | 1135 | | | | | 1140 | | | | | 1145 | | | |

| | | | | | | | | | | | | | | |
|---|---|---|---|---|---|---|---|---|---|---|---|---|---|---|---|
| aga | cgc | ggg | gac | aag | cgg | gga | gca | ttg | ctc | tcc | ccg | aga | ccc | att | 3826 |
| Arg | Arg | Gly | Asp | Lys | Arg | Gly | Ala | Leu | Leu | Ser | Pro | Arg | Pro | Ile | |
| | 1150 | | | | | 1155 | | | | | 1160 | | | | |

| | | | | | | | | | | | | | | |
|---|---|---|---|---|---|---|---|---|---|---|---|---|---|---|---|
| tcg | acc | ttg | aag | ggg | tcc | tcg | ggg | ggg | ccg | gtg | ctc | tgc | cct | agg | 3871 |
| Ser | Thr | Leu | Lys | Gly | Ser | Ser | Gly | Gly | Pro | Val | Leu | Cys | Pro | Arg | |
| | | 1165 | | | | | 1170 | | | | | 1175 | | | |

```
ggc cac gtc gtt ggg ctc ttc cga gca gct gtg tgc tct cgg ggc      3916
Gly His Val Val Gly Leu Phe Arg Ala Ala Val Cys Ser Arg Gly
        1180                1185                1190 gtg gcc aaa tcc atc gat ttc atc ccc gtt gag aca ctc gac gtt      3961
Val Ala Lys Ser Ile Asp Phe Ile Pro Val Glu Thr Leu Asp Val
        1195                1200                1205 gtt aca agg tct ccc act ttc agt gac aac agc acg cca ccg gct      4006
Val Thr Arg Ser Pro Thr Phe Ser Asp Asn Ser Thr Pro Pro Ala
        1210                1215                1220 gtg ccc cag acc tat cag gtc ggg tac ttg cat gct cca act ggc      4051
Val Pro Gln Thr Tyr Gln Val Gly Tyr Leu His Ala Pro Thr Gly
        1225                1230                1235 agt gga aag agc acc aag gtc cct gtc gcg tat gcc gcc cag ggg      4096
Ser Gly Lys Ser Thr Lys Val Pro Val Ala Tyr Ala Ala Gln Gly
        1240                1245                1250 tac aaa gta cta gtg ctt aac ccc tcg gta gct gcc acc ctg ggg      4141
Tyr Lys Val Leu Val Leu Asn Pro Ser Val Ala Ala Thr Leu Gly
        1255                1260                1265 ttt ggg gcg tac cta tcc aag gca cat ggc atc aat ccc aac att      4186
Phe Gly Ala Tyr Leu Ser Lys Ala His Gly Ile Asn Pro Asn Ile
        1270                1275                1280 agg act gga gtc agg acc gtg atg acc ggg gag gcc atc acg tac      4231
Arg Thr Gly Val Arg Thr Val Met Thr Gly Glu Ala Ile Thr Tyr
        1285                1290                1295 tcc aca tat ggc aaa ttt ctc gcc gat ggg ggc tgc gct agc ggc      4276
Ser Thr Tyr Gly Lys Phe Leu Ala Asp Gly Gly Cys Ala Ser Gly
        1300                1305                1310 gcc tat gac atc atc ata tgc gat gaa tgc cac gct gtg gat gct      4321
Ala Tyr Asp Ile Ile Ile Cys Asp Glu Cys His Ala Val Asp Ala
        1315                1320                1325 acc tcc att ctc ggc atc gga acg gtc ctt gat caa gca gag aca      4366
Thr Ser Ile Leu Gly Ile Gly Thr Val Leu Asp Gln Ala Glu Thr
        1330                1335                1340 gcc ggg gtc aga cta act gtg ctg gct acg gcc aca ccc ccc ggg      4411
Ala Gly Val Arg Leu Thr Val Leu Ala Thr Ala Thr Pro Pro Gly
        1345                1350                1355 tca gtg aca acc ccc cat ccc gat ata gaa gag gta ggc ctc ggg      4456
Ser Val Thr Thr Pro His Pro Asp Ile Glu Glu Val Gly Leu Gly
        1360                1365                1370 cgg gag ggt gag atc ccc ttc tat ggg agg gcg att ccc cta tcc      4501
Arg Glu Gly Glu Ile Pro Phe Tyr Gly Arg Ala Ile Pro Leu Ser
        1375                1380                1385 tgc atc aag gga ggg aga cac ctg att ttc tgc cac tca aag aaa      4546
Cys Ile Lys Gly Gly Arg His Leu Ile Phe Cys His Ser Lys Lys
        1390                1395                1400 aag tgt gac gag ctc gcg gcg gcc ctt cgg ggc atg ggc ttg aat      4591
Lys Cys Asp Glu Leu Ala Ala Ala Leu Arg Gly Met Gly Leu Asn
        1405                1410                1415 gcc gtg gca tac tat aga ggg ttg gac gtc tcc ata ata cca gct      4636
Ala Val Ala Tyr Tyr Arg Gly Leu Asp Val Ser Ile Ile Pro Ala
        1420                1425                1430 cag gga gat gtg gtg gtc gtc gcc acc gac gcc ctc atg acg ggg      4681
Gln Gly Asp Val Val Val Val Ala Thr Asp Ala Leu Met Thr Gly
        1435                1440                1445 tac act gga gac ttt gac tcc gtg atc gac tgc aat gta gcg gtc      4726
Tyr Thr Gly Asp Phe Asp Ser Val Ile Asp Cys Asn Val Ala Val
        1450                1455                1460 acc caa gct gtc gac ttc agc ctg gac ccc acc ttc act ata acc      4771
Thr Gln Ala Val Asp Phe Ser Leu Asp Pro Thr Phe Thr Ile Thr
```

-continued

|  |  |  |  |
|---|---|---|---|
| aca cag act gtc cca caa gac gct gtc tca cgc agt cag cgc cgc<br>Thr Gln Thr Val Pro Gln Asp Ala Val Ser Arg Ser Gln Arg Arg<br>           1480                    1485                   1490 | 4816 |

```
                       1465                1470                1475 aca cag act gtc cca caa gac gct gtc tca cgc agt cag cgc cgc        4816
Thr Gln Thr Val Pro Gln Asp Ala Val Ser Arg Ser Gln Arg Arg
            1480                1485                1490 ggg cgc aca ggt aga gga aga cag ggc act tat agg tat gtt tcc        4861
Gly Arg Thr Gly Arg Gly Arg Gln Gly Thr Tyr Arg Tyr Val Ser
            1495                1500                1505 act ggt gaa cga gcc tca gga atg ttt gac agt gta gtg ctt tgt        4906
Thr Gly Glu Arg Ala Ser Gly Met Phe Asp Ser Val Val Leu Cys
            1510                1515                1520 gag tgc tac gac gca ggg gct gcg tgg tac gat ctc aca cca gcg        4951
Glu Cys Tyr Asp Ala Gly Ala Ala Trp Tyr Asp Leu Thr Pro Ala
            1525                1530                1535 gag acc acc gtc agg ctt aga gcg tat ttc aac acg ccc ggc cta        4996
Glu Thr Thr Val Arg Leu Arg Ala Tyr Phe Asn Thr Pro Gly Leu
            1540                1545                1550 ccc gtg tgt caa gac cat ctt gaa ttt tgg gag gca gtt ttc acc        5041
Pro Val Cys Gln Asp His Leu Glu Phe Trp Glu Ala Val Phe Thr
            1555                1560                1565 ggc ctc aca cac ata gac gcc cac ttc ctc tcc caa aca aag caa        5086
Gly Leu Thr His Ile Asp Ala His Phe Leu Ser Gln Thr Lys Gln
            1570                1575                1580 gcg ggg gag aac ttc gcg tac cta gta gcc tac caa gct acg gtg        5131
Ala Gly Glu Asn Phe Ala Tyr Leu Val Ala Tyr Gln Ala Thr Val
            1585                1590                1595 tgc gcc aga gcc aag gcc cct ccc ccg tcc tgg gac gcc atg tgg        5176
Cys Ala Arg Ala Lys Ala Pro Pro Pro Ser Trp Asp Ala Met Trp
            1600                1605                1610 aag tgc ctg gcc cga ctc aag cct acg ctt gcg ggc ccc aca cct        5221
Lys Cys Leu Ala Arg Leu Lys Pro Thr Leu Ala Gly Pro Thr Pro
            1615                1620                1625 ctc ctg tac cgt ttg ggc cct att acc aat gag gtc acc ctc aca        5266
Leu Leu Tyr Arg Leu Gly Pro Ile Thr Asn Glu Val Thr Leu Thr
            1630                1635                1640 cac cct ggg acg aag tac atc gcc aca tgc atg caa gct gac ctt        5311
His Pro Gly Thr Lys Tyr Ile Ala Thr Cys Met Gln Ala Asp Leu
            1645                1650                1655 gag gtc atg acc agc acg tgg gtc cta gct gga gga gtc ctg gca        5356
Glu Val Met Thr Ser Thr Trp Val Leu Ala Gly Gly Val Leu Ala
            1660                1665                1670 gcc gtc gcc gca tat tgc ctg gcg act gga tgc gtt tcc atc atc        5401
Ala Val Ala Ala Tyr Cys Leu Ala Thr Gly Cys Val Ser Ile Ile
            1675                1680                1685 ggc cgc ttg cac gtc aac cag cga gtc gtc gtt gcg ccg gat aag        5446
Gly Arg Leu His Val Asn Gln Arg Val Val Val Ala Pro Asp Lys
            1690                1695                1700 gag gtc ctg tat gag gct ttt gat gag atg gag gaa tgc gcc tct        5491
Glu Val Leu Tyr Glu Ala Phe Asp Glu Met Glu Glu Cys Ala Ser
            1705                1710                1715 agg gcg gct ctc atc gaa gag ggg cag cgg ata gcc gag atg ttg        5536
Arg Ala Ala Leu Ile Glu Glu Gly Gln Arg Ile Ala Glu Met Leu
            1720                1725                1730 aag tcc aag atc caa ggc ttg ctg cag cag gcc tct aag cag gcc        5581
Lys Ser Lys Ile Gln Gly Leu Leu Gln Gln Ala Ser Lys Gln Ala
            1735                1740                1745 cag gac ata caa ccc gct atg cag gct tca tgg ccc aaa gtg gaa        5626
Gln Asp Ile Gln Pro Ala Met Gln Ala Ser Trp Pro Lys Val Glu
            1750                1755                1760 caa ttt tgg gcc aga cac atg tgg aac ttc att agc ggc atc caa        5671
Gln Phe Trp Ala Arg His Met Trp Asn Phe Ile Ser Gly Ile Gln
```

-continued

| | | |
|---|---|---|
| Gln Phe Trp Ala Arg His Met Trp Asn Phe Ile Ser Gly Ile Gln<br>1765 1770 1775 | | |
| tac ctc gca gga ttg tca aca ctg cca ggg aac ccc gcg gtg gct<br>Tyr Leu Ala Gly Leu Ser Thr Leu Pro Gly Asn Pro Ala Val Ala<br>1780 1785 1790 | 5716 | |
| tcc atg atg gca ttc agt gcc gcc ctc acc agt ccg ttg tcg acc<br>Ser Met Met Ala Phe Ser Ala Ala Leu Thr Ser Pro Leu Ser Thr<br>1795 1800 1805 | 5761 | |
| agt acc acc atc ctt ctc aac atc atg gga ggc tgg tta gcg tcc<br>Ser Thr Thr Ile Leu Leu Asn Ile Met Gly Gly Trp Leu Ala Ser<br>1810 1815 1820 | 5806 | |
| cag atc gca cca ccc gcg ggg gcc acc ggc ttt gtc gtc agt ggc<br>Gln Ile Ala Pro Pro Ala Gly Ala Thr Gly Phe Val Val Ser Gly<br>1825 1830 1835 | 5851 | |
| ctg gtg ggg gct gcc gtg ggc agc ata ggc ctg ggt aag gtg ctg<br>Leu Val Gly Ala Ala Val Gly Ser Ile Gly Leu Gly Lys Val Leu<br>1840 1845 1850 | 5896 | |
| gtg gac atc ctg gca gga tat ggt gcg ggc att tcg ggg gcc ctg<br>Val Asp Ile Leu Ala Gly Tyr Gly Ala Gly Ile Ser Gly Ala Leu<br>1855 1860 1865 | 5941 | |
| gtc gca ttc aag atc atg tct ggc gag aag ccc tct atg gaa gat<br>Val Ala Phe Lys Ile Met Ser Gly Glu Lys Pro Ser Met Glu Asp<br>1870 1875 1880 | 5986 | |
| gtc atc aat cta ctg cct ggg atc ctg tct ccg gga gcc ctg gtg<br>Val Ile Asn Leu Leu Pro Gly Ile Leu Ser Pro Gly Ala Leu Val<br>1885 1890 1895 | 6031 | |
| gtg ggg gtc atc tgc gcg gcc att ctg cgc cgc cac gtg gga ccg<br>Val Gly Val Ile Cys Ala Ala Ile Leu Arg Arg His Val Gly Pro<br>1900 1905 1910 | 6076 | |
| ggg gag ggc gcg gtc caa tgg atg aac agg ctt att gcc ttt gct<br>Gly Glu Gly Ala Val Gln Trp Met Asn Arg Leu Ile Ala Phe Ala<br>1915 1920 1925 | 6121 | |
| tcc aga gga aac cac gtc gcc cct act cac tac gtg acg gag tcg<br>Ser Arg Gly Asn His Val Ala Pro Thr His Tyr Val Thr Glu Ser<br>1930 1935 1940 | 6166 | |
| gat gcg tcg cag cgt gtg acc caa cta ctt ggc tct ctt act ata<br>Asp Ala Ser Gln Arg Val Thr Gln Leu Leu Gly Ser Leu Thr Ile<br>1945 1950 1955 | 6211 | |
| acc agc cta ctc aga aga ctc cac aat tgg ata act gag gac tgc<br>Thr Ser Leu Leu Arg Arg Leu His Asn Trp Ile Thr Glu Asp Cys<br>1960 1965 1970 | 6256 | |
| ccc atc cca tgc tcc gga tcc tgg ctc cgc gac gtg tgg gac tgg<br>Pro Ile Pro Cys Ser Gly Ser Trp Leu Arg Asp Val Trp Asp Trp<br>1975 1980 1985 | 6301 | |
| gtt tgc acc atc ttg aca gac ttc aaa aat tgg ctg acc tct aaa<br>Val Cys Thr Ile Leu Thr Asp Phe Lys Asn Trp Leu Thr Ser Lys<br>1990 1995 2000 | 6346 | |
| ttg ttc ccc aag ctg ccc ggc ctc ccc ttc atc tct tgt caa aag<br>Leu Phe Pro Lys Leu Pro Gly Leu Pro Phe Ile Ser Cys Gln Lys<br>2005 2010 2015 | 6391 | |
| ggg tac aag ggt gtg tgg gcc ggc act ggc atc atg acc acg cgc<br>Gly Tyr Lys Gly Val Trp Ala Gly Thr Gly Ile Met Thr Thr Arg<br>2020 2025 2030 | 6436 | |
| tgc cct tgc ggc gcc aac atc tct ggc aat gtc cgc ctg ggc tct<br>Cys Pro Cys Gly Ala Asn Ile Ser Gly Asn Val Arg Leu Gly Ser<br>2035 2040 2045 | 6481 | |
| atg agg atc aca ggg cct aaa acc tgc atg aac acc tgg cag ggg<br>Met Arg Ile Thr Gly Pro Lys Thr Cys Met Asn Thr Trp Gln Gly<br>2050 2055 2060 | 6526 | |

```
acc ttt cct atc aat tgc tac acg gag ggc cag tgc gcg ccg aaa       6571
Thr Phe Pro Ile Asn Cys Tyr Thr Glu Gly Gln Cys Ala Pro Lys
        2065            2070            2075 ccc ccc acg aac tac aag acc gcc atc tgg agg gtg gcg gcc tcg       6616
Pro Pro Thr Asn Tyr Lys Thr Ala Ile Trp Arg Val Ala Ala Ser
        2080            2085            2090 gag tac gcg gag gtg acg cag cat ggg tcg tac tcc tat gta aca       6661
Glu Tyr Ala Glu Val Thr Gln His Gly Ser Tyr Ser Tyr Val Thr
        2095            2100            2105 gga ctg acc act gac aat ctg aaa att cct tgc caa cta cct tct       6706
Gly Leu Thr Thr Asp Asn Leu Lys Ile Pro Cys Gln Leu Pro Ser
        2110            2115            2120 cca gag ttt ttc tcc tgg gtg gac ggt gtg cag atc cat agg ttt       6751
Pro Glu Phe Phe Ser Trp Val Asp Gly Val Gln Ile His Arg Phe
        2125            2130            2135 gca ccc aca cca aag ccg ttt ttc cgg gat gag gtc tcg ttc tgc       6796
Ala Pro Thr Pro Lys Pro Phe Phe Arg Asp Glu Val Ser Phe Cys
        2140            2145            2150 gtt ggg ctt aat tcc tat gct gtc ggg tcc cag ctt ccc tgt gaa       6841
Val Gly Leu Asn Ser Tyr Ala Val Gly Ser Gln Leu Pro Cys Glu
        2155            2160            2165 cct gag ccc gac gca gac gta ttg agg tcc atg cta aca gat ccg       6886
Pro Glu Pro Asp Ala Asp Val Leu Arg Ser Met Leu Thr Asp Pro
        2170            2175            2180 ccc cac atc acg gcg gag act gcg gcg cgg cgc ttg gca cgg gga       6931
Pro His Ile Thr Ala Glu Thr Ala Ala Arg Arg Leu Ala Arg Gly
        2185            2190            2195 tca cct cca tct gag gcg agc tcc tca gtg agc cag cta tca gca       6976
Ser Pro Pro Ser Glu Ala Ser Ser Ser Val Ser Gln Leu Ser Ala
        2200            2205            2210 ccg tcg ctg cgg gcc acc tgc acc acc cac agc aac acc tat gac       7021
Pro Ser Leu Arg Ala Thr Cys Thr Thr His Ser Asn Thr Tyr Asp
        2215            2220            2225 gtg gac atg gtc gat gcc aac ctg ctc atg gag ggc ggt gtg gct       7066
Val Asp Met Val Asp Ala Asn Leu Leu Met Glu Gly Gly Val Ala
        2230            2235            2240 cag aca gag cct gag tcc agg gtg ccc gtt ctg gac ttt ctc gag       7111
Gln Thr Glu Pro Glu Ser Arg Val Pro Val Leu Asp Phe Leu Glu
        2245            2250            2255 cca atg gcc gag gaa gag agc gac ctt gag ccc tca ata cca tcg       7156
Pro Met Ala Glu Glu Glu Ser Asp Leu Glu Pro Ser Ile Pro Ser
        2260            2265            2270 gag tgc atg ctc ccc agg agc ggg ttt cca cgg gcc tta ccg gct       7201
Glu Cys Met Leu Pro Arg Ser Gly Phe Pro Arg Ala Leu Pro Ala
        2275            2280            2285 tgg gca cgg cct gac tac aac ccg ccg ctc gtg gaa tcg tgg agg       7246
Trp Ala Arg Pro Asp Tyr Asn Pro Pro Leu Val Glu Ser Trp Arg
        2290            2295            2300 agg cca gat tac caa ccg ccc acc gtt gct ggt tgt gct ctc ccc       7291
Arg Pro Asp Tyr Gln Pro Pro Thr Val Ala Gly Cys Ala Leu Pro
        2305            2310            2315 ccc ccc aag aag gcc ccg acg cct ccc cca agg aga cgc cgg aca       7336
Pro Pro Lys Lys Ala Pro Thr Pro Pro Pro Arg Arg Arg Arg Thr
        2320            2325            2330 gtg ggt ctg agc gag agc acc ata tca gaa gcc ctc cag caa ctg       7381
Val Gly Leu Ser Glu Ser Thr Ile Ser Glu Ala Leu Gln Gln Leu
        2335            2340            2345 gcc atc aag acc ttt ggc cag ccc ccc tcg agc ggt gat gca ggc       7426
Ala Ile Lys Thr Phe Gly Gln Pro Pro Ser Ser Gly Asp Ala Gly
        2350            2355            2360
```

-continued

| | | |
|---|---|---|
| tcg tcc acg ggg gcg ggc gcc gcc gaa tcc ggc ggt ccg acg tcc<br>Ser Ser Thr Gly Ala Gly Ala Ala Glu Ser Gly Gly Pro Thr Ser<br>2365 2370 2375 | 7471 | |
| cct ggt gag ccg gcc ccc tca gag aca ggt tcc gcc tcc tct atg<br>Pro Gly Glu Pro Ala Pro Ser Glu Thr Gly Ser Ala Ser Ser Met<br>2380 2385 2390 | 7516 | |
| ccc ccc ctc gag ggg gag cct gga gat ccg gac ctg gag tct gat<br>Pro Pro Leu Glu Gly Glu Pro Gly Asp Pro Asp Leu Glu Ser Asp<br>2395 2400 2405 | 7561 | |
| cag gta gag ctt caa cct ccc cag ggg ggg ggg gta gct ccc<br>Gln Val Glu Leu Gln Pro Pro Pro Gln Gly Gly Gly Val Ala Pro<br>2410 2415 2420 | 7606 | |
| ggt tcg ggc tcg ggg tct tgg tct act tgc tcc gag gag gac gat<br>Gly Ser Gly Ser Gly Ser Trp Ser Thr Cys Ser Glu Glu Asp Asp<br>2425 2430 2435 | 7651 | |
| acc acc gtg tgc tgc tcc atg tca tac tcc tgg acc ggg gct cta<br>Thr Thr Val Cys Cys Ser Met Ser Tyr Ser Trp Thr Gly Ala Leu<br>2440 2445 2450 | 7696 | |
| ata act ccc tgt agc ccc gaa gag gaa aag ttg cca atc aac cct<br>Ile Thr Pro Cys Ser Pro Glu Glu Glu Lys Leu Pro Ile Asn Pro<br>2455 2460 2465 | 7741 | |
| ttg agt aac tcg ctg ttg cga tac cat aac aag gtg tac tgt aca<br>Leu Ser Asn Ser Leu Leu Arg Tyr His Asn Lys Val Tyr Cys Thr<br>2470 2475 2480 | 7786 | |
| aca tca aag agc gcc tca cag agg gct aaa aag gta act ttt gac<br>Thr Ser Lys Ser Ala Ser Gln Arg Ala Lys Lys Val Thr Phe Asp<br>2485 2490 2495 | 7831 | |
| agg acg caa gtg ctc gac gcc cat tat gac tca gtc tta aag gac<br>Arg Thr Gln Val Leu Asp Ala His Tyr Asp Ser Val Leu Lys Asp<br>2500 2505 2510 | 7876 | |
| atc aag cta gcg gct tcc aag gtc agc gca agg ctc ctc acc ttg<br>Ile Lys Leu Ala Ala Ser Lys Val Ser Ala Arg Leu Leu Thr Leu<br>2515 2520 2525 | 7921 | |
| gag gag gcg tgc cag ttg act cca ccc cat tct gca aga tcc aag<br>Glu Glu Ala Cys Gln Leu Thr Pro Pro His Ser Ala Arg Ser Lys<br>2530 2535 2540 | 7966 | |
| tat gga ttc ggg gcc aag gag gtc cgc agc ttg tcc ggg agg gcc<br>Tyr Gly Phe Gly Ala Lys Glu Val Arg Ser Leu Ser Gly Arg Ala<br>2545 2550 2555 | 8011 | |
| gtt aac cac atc aag tcc gtg tgg aag gac ctc ctg gaa gac cca<br>Val Asn His Ile Lys Ser Val Trp Lys Asp Leu Leu Glu Asp Pro<br>2560 2565 2570 | 8056 | |
| caa aca cca att ccc aca acc atc atg gcc aaa aat gag gtg ttc<br>Gln Thr Pro Ile Pro Thr Thr Ile Met Ala Lys Asn Glu Val Phe<br>2575 2580 2585 | 8101 | |
| tgc gtg gac ccc gcc aag ggg ggt aag aaa cca gct cgc ctc atc<br>Cys Val Asp Pro Ala Lys Gly Gly Lys Lys Pro Ala Arg Leu Ile<br>2590 2595 2600 | 8146 | |
| gtt tac cct gac ctc ggc gtc cgg gtc tgc gag aaa atg gcc ctc<br>Val Tyr Pro Asp Leu Gly Val Arg Val Cys Glu Lys Met Ala Leu<br>2605 2610 2615 | 8191 | |
| tat gac att aca caa aag ctt cct cag gcg gta atg gga gct tcc<br>Tyr Asp Ile Thr Gln Lys Leu Pro Gln Ala Val Met Gly Ala Ser<br>2620 2625 2630 | 8236 | |
| tat ggc ttc cag tac tcc cct gcc caa cgg gtg gag tat ctc ttg<br>Tyr Gly Phe Gln Tyr Ser Pro Ala Gln Arg Val Glu Tyr Leu Leu<br>2635 2640 2645 | 8281 | |
| aaa gca tgg gcg gaa aag aag gac ccc atg ggt ttt tcg tat gat<br>Lys Ala Trp Ala Glu Lys Lys Asp Pro Met Gly Phe Ser Tyr Asp | 8326 | |

|     |     |     |     |     |     |     |     |     |     |     |     |     |     |     |      |
|---|---|---|---|---|---|---|---|---|---|---|---|---|---|---|---|
|     |     | 2650 |     |     |     | 2655 |     |     |     |     | 2660 |     |     |     |      |
| acc | cga | tgc | ttc | gac | tca | acc | gtc | act | gag | aga | gac | atc | agg | acc | 8371 |
| Thr | Arg | Cys | Phe | Asp | Ser | Thr | Val | Thr | Glu | Arg | Asp | Ile | Arg | Thr |      |
|     |     | 2665 |     |     |     | 2670 |     |     |     |     | 2675 |     |     |     |      |
| gag | gag | tcc | ata | tac | cag | gcc | tgc | tcc | ctg | ccc | gag | gag | gcc | cgc | 8416 |
| Glu | Glu | Ser | Ile | Tyr | Gln | Ala | Cys | Ser | Leu | Pro | Glu | Glu | Ala | Arg |      |
|     |     | 2680 |     |     |     | 2685 |     |     |     |     | 2690 |     |     |     |      |
| act | gcc | ata | cac | tcg | ctg | act | gag | aga | ctt | tac | gta | gga | ggg | ccc | 8461 |
| Thr | Ala | Ile | His | Ser | Leu | Thr | Glu | Arg | Leu | Tyr | Val | Gly | Gly | Pro |      |
|     |     | 2695 |     |     |     | 2700 |     |     |     |     | 2705 |     |     |     |      |
| atg | ttc | aac | agc | aag | ggt | caa | acc | tgc | ggt | tac | aga | cgt | tgc | cgc | 8506 |
| Met | Phe | Asn | Ser | Lys | Gly | Gln | Thr | Cys | Gly | Tyr | Arg | Arg | Cys | Arg |      |
|     |     | 2710 |     |     |     | 2715 |     |     |     |     | 2720 |     |     |     |      |
| gcc | agc | ggg | gtg | cta | acc | act | agc | atg | ggt | aac | acc | atc | aca | tgc | 8551 |
| Ala | Ser | Gly | Val | Leu | Thr | Thr | Ser | Met | Gly | Asn | Thr | Ile | Thr | Cys |      |
|     |     | 2725 |     |     |     | 2730 |     |     |     |     | 2735 |     |     |     |      |
| tat | gtg | aaa | gcc | cta | gcg | gcc | tgc | aag | gct | gcg | ggg | ata | gtt | gcg | 8596 |
| Tyr | Val | Lys | Ala | Leu | Ala | Ala | Cys | Lys | Ala | Ala | Gly | Ile | Val | Ala |      |
|     |     | 2740 |     |     |     | 2745 |     |     |     |     | 2750 |     |     |     |      |
| ccc | aca | atg | ctg | gta | tgc | ggc | gat | gac | cta | gta | gtc | atc | tca | gaa | 8641 |
| Pro | Thr | Met | Leu | Val | Cys | Gly | Asp | Asp | Leu | Val | Val | Ile | Ser | Glu |      |
|     |     | 2755 |     |     |     | 2760 |     |     |     |     | 2765 |     |     |     |      |
| agc | cag | ggg | act | gag | gag | gac | gag | cgg | aac | ctg | aga | gcc | ttc | acg | 8686 |
| Ser | Gln | Gly | Thr | Glu | Glu | Asp | Glu | Arg | Asn | Leu | Arg | Ala | Phe | Thr |      |
|     |     | 2770 |     |     |     | 2775 |     |     |     |     | 2780 |     |     |     |      |
| gag | gcc | atg | acc | agg | tac | tct | gcc | cct | cct | ggt | gat | ccc | ccc | aga | 8731 |
| Glu | Ala | Met | Thr | Arg | Tyr | Ser | Ala | Pro | Pro | Gly | Asp | Pro | Pro | Arg |      |
|     |     | 2785 |     |     |     | 2790 |     |     |     |     | 2795 |     |     |     |      |
| ccg | gaa | tat | gac | ctg | gag | cta | ata | aca | tcc | tgt | tcc | tca | aat | gtg | 8776 |
| Pro | Glu | Tyr | Asp | Leu | Glu | Leu | Ile | Thr | Ser | Cys | Ser | Ser | Asn | Val |      |
|     |     | 2800 |     |     |     | 2805 |     |     |     |     | 2810 |     |     |     |      |
| tct | gtg | gcg | ttg | ggc | ccg | cgg | ggc | cgc | cgc | aga | tac | tac | ctg | acc | 8821 |
| Ser | Val | Ala | Leu | Gly | Pro | Arg | Gly | Arg | Arg | Arg | Tyr | Tyr | Leu | Thr |      |
|     |     | 2815 |     |     |     | 2820 |     |     |     |     | 2825 |     |     |     |      |
| aga | gac | cca | acc | act | cca | ctc | gcc | cgg | gct | gcc | tgg | gaa | aca | gtt | 8866 |
| Arg | Asp | Pro | Thr | Thr | Pro | Leu | Ala | Arg | Ala | Ala | Trp | Glu | Thr | Val |      |
|     |     | 2830 |     |     |     | 2835 |     |     |     |     | 2840 |     |     |     |      |
| aga | cac | tcc | cct | atc | aat | tca | tgg | ctg | gga | aac | atc | atc | cag | tat | 8911 |
| Arg | His | Ser | Pro | Ile | Asn | Ser | Trp | Leu | Gly | Asn | Ile | Ile | Gln | Tyr |      |
|     |     | 2845 |     |     |     | 2850 |     |     |     |     | 2855 |     |     |     |      |
| gct | cca | acc | ata | tgg | gtt | cgc | atg | gtc | cta | atg | aca | cac | ttc | ttc | 8956 |
| Ala | Pro | Thr | Ile | Trp | Val | Arg | Met | Val | Leu | Met | Thr | His | Phe | Phe |      |
|     |     | 2860 |     |     |     | 2865 |     |     |     |     | 2870 |     |     |     |      |
| tcc | att | ctc | atg | gtc | caa | gac | acc | ctg | gac | cag | aac | ctc | aac | ttt | 9001 |
| Ser | Ile | Leu | Met | Val | Gln | Asp | Thr | Leu | Asp | Gln | Asn | Leu | Asn | Phe |      |
|     |     | 2875 |     |     |     | 2880 |     |     |     |     | 2885 |     |     |     |      |
| gag | atg | tat | gga | tca | gta | tac | tcc | gtg | aat | cct | ttg | gac | ctt | cca | 9046 |
| Glu | Met | Tyr | Gly | Ser | Val | Tyr | Ser | Val | Asn | Pro | Leu | Asp | Leu | Pro |      |
|     |     | 2890 |     |     |     | 2895 |     |     |     |     | 2900 |     |     |     |      |
| gcc | ata | att | gag | agg | tta | cac | ggg | ctt | gac | gcc | ttt | tct | atg | cac | 9091 |
| Ala | Ile | Ile | Glu | Arg | Leu | His | Gly | Leu | Asp | Ala | Phe | Ser | Met | His |      |
|     |     | 2905 |     |     |     | 2910 |     |     |     |     | 2915 |     |     |     |      |
| aca | tac | tct | cac | cac | gaa | ctg | acg | cgg | gtg | gct | tca | gcc | ctc | aga | 9136 |
| Thr | Tyr | Ser | His | His | Glu | Leu | Thr | Arg | Val | Ala | Ser | Ala | Leu | Arg |      |
|     |     | 2920 |     |     |     | 2925 |     |     |     |     | 2930 |     |     |     |      |
| aaa | ctt | ggg | gcg | cca | ccc | ctc | agg | gtg | tgg | aag | agt | cgg | gct | cgc | 9181 |
| Lys | Leu | Gly | Ala | Pro | Pro | Leu | Arg | Val | Trp | Lys | Ser | Arg | Ala | Arg |      |
|     |     | 2935 |     |     |     | 2940 |     |     |     |     | 2945 |     |     |     |      |
| gca | gtc | agg | gcg | tcc | ctc | atc | tcc | cgt | gga | ggg | aaa | gcg | gcc | gtt | 9226 |

```
Ala Val Arg Ala Ser Leu Ile Ser Arg Gly Gly Lys Ala Ala Val
            2950                2955                2960 tgc ggc cga tat ctc ttc aat tgg gcg gtg aag acc aag ctc aaa     9271
Cys Gly Arg Tyr Leu Phe Asn Trp Ala Val Lys Thr Lys Leu Lys
            2965                2970                2975 ctc act cca ttg ccg gag gcg cgc cta ctg gac tta tcc agt tgg     9316
Leu Thr Pro Leu Pro Glu Ala Arg Leu Leu Asp Leu Ser Ser Trp
            2980                2985                2990 ttc acc gtc ggc gcc ggc ggg ggc gac att ttt cac agc gtg tcg     9361
Phe Thr Val Gly Ala Gly Gly Gly Asp Ile Phe His Ser Val Ser
            2995                3000                3005 cgc gcc cga ccc cgc tca tta ctc ttc ggc cta ctc ctt ttc         9406
Arg Ala Arg Pro Arg Ser Leu Leu Phe Gly Leu Leu Leu Phe
            3010                3015                3020 gta ggg gta ggc ctc ttc cta ctc ccc gct cgg tag agcggcacac      9452
Val Gly Val Gly Leu Phe Leu Leu Pro Ala Arg
            3025                3030 actaggtaca ctccatagct aactgttcct tttttttttt tttttttttt tttttttttt    9512
tttttttttt ttctttttt tttttttccc tctttcttcc cttctcatct tattctactt    9572
tctttcttgg tggctccatc ttagccctag tcacggctag ctgtgaaagg tccgtgagcc   9632
gcatgactgc agagagtgcc gtaactggtc tctctgcaga tcatgt                  9678

<210> SEQ ID NO 2
<211> LENGTH: 3033
<212> TYPE: PRT
<213> ORGANISM: Hepatitis C virus JFH1 strain

<400> SEQUENCE: 2

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
                20                  25                  30

Gly Val Tyr Leu Leu Pro Arg Arg Gly Pro Arg Leu Gly Val Arg Thr
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
130                 135                 140

Ser Gly Ala Ala Arg Ala Val Ala His Gly Val Arg Val Leu Glu Asp
145                 150                 155                 160

Gly Val Asn Tyr Ala Thr Gly Asn Leu Pro Gly Phe Pro Phe Ser Ile
                165                 170                 175

Phe Leu Leu Ala Leu Leu Ser Cys Ile Thr Val Pro Val Ser Ala Ala
            180                 185                 190

Gln Val Lys Asn Thr Ser Ser Ser Tyr Met Val Thr Asn Asp Cys Ser
        195                 200                 205

Asn Asp Ser Ile Thr Trp Gln Leu Glu Ala Ala Val Leu His Val Pro
```

-continued

```
              210                 215                 220
Gly Cys Val Pro Cys Glu Arg Val Gly Asn Thr Ser Arg Cys Trp Val
225                 230                 235                 240

Pro Val Ser Pro Asn Met Ala Val Arg Gln Pro Gly Ala Leu Thr Gln
                245                 250                 255

Gly Leu Arg Thr His Ile Asp Met Val Met Ser Ala Thr Phe Cys
                260                 265                 270

Ser Ala Leu Tyr Val Gly Asp Leu Cys Gly Val Met Leu Ala Ala
            275                 280                 285

Gln Val Phe Ile Val Ser Pro Gln Tyr His Trp Phe Val Gln Glu Cys
            290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Val Met Arg Val Pro Glu Val Ile Ile Asp Ile Val Ser Gly Ala His
                340                 345                 350

Trp Gly Val Met Phe Gly Leu Ala Tyr Phe Ser Met Gln Gly Ala Trp
                355                 360                 365

Ala Lys Val Ile Val Ile Leu Leu Leu Ala Ala Gly Val Asp Ala Gly
                370                 375             380

Thr Thr Thr Val Gly Gly Ala Val Ala Arg Ser Thr Asn Val Ile Ala
385                 390                 395                 400

Gly Val Phe Ser His Gly Pro Gln Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Thr Asn Arg Phe Asn
                435                 440                 445

Ser Ser Gly Cys Pro Gly Arg Leu Ser Ala Cys Arg Asn Ile Glu Ala
                450                 455                 460

Phe Arg Ile Gly Trp Gly Thr Leu Gln Tyr Glu Asp Asn Val Thr Asn
465                 470                 475                 480

Pro Glu Asp Met Arg Pro Tyr Cys Trp His Tyr Pro Lys Pro Cys
                485                 490                 495

Gly Val Val Pro Ala Arg Ser Val Cys Gly Pro Val Tyr Cys Phe Thr
                500                 505                 510

Pro Ser Pro Val Val Gly Thr Thr Asp Arg Arg Gly Val Pro Thr
                515                 520                 525

Tyr Thr Trp Gly Glu Asn Glu Thr Asp Val Phe Leu Leu Asn Ser Thr
                530                 535                 540

Arg Pro Pro Gln Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
                580                 585                 590

His Pro Asp Ala Thr Tyr Ile Lys Cys Gly Ser Gly Pro Trp Leu Thr
                595                 600                 605

Pro Lys Cys Leu Val His Tyr Pro Tyr Arg Leu Trp His Tyr Pro Cys
                610                 615                 620

Thr Val Asn Phe Thr Ile Phe Lys Ile Arg Met Tyr Val Gly Gly Val
625                 630                 635                 640
```

```
Glu His Arg Leu Thr Ala Ala Cys Asn Phe Thr Arg Gly Asp Arg Cys
            645                 650                 655

Asp Leu Glu Asp Arg Asp Arg Ser Gln Leu Ser Pro Leu Leu His Ser
            660                 665                 670

Thr Thr Glu Trp Ala Ile Leu Pro Cys Thr Tyr Ser Asp Leu Pro Ala
            675                 680                 685

Leu Ser Thr Gly Leu Leu His Leu His Gln Asn Ile Val Asp Val Gln
            690                 695                 700

Tyr Met Tyr Gly Leu Ser Pro Ala Ile Thr Lys Tyr Val Val Arg Trp
705                 710                 715                 720

Glu Trp Val Val Leu Phe Leu Leu Leu Ala Asp Ala Arg Val Cys
            725                 730                 735

Ala Cys Leu Trp Met Leu Ile Leu Leu Gly Gln Ala Glu Ala Leu
            740                 745                 750

Glu Lys Leu Val Val Leu His Ala Ala Ser Ala Ala Asn Cys His Gly
            755                 760                 765

Leu Leu Tyr Phe Ala Ile Phe Phe Val Ala Ala Trp His Ile Arg Gly
            770                 775                 780

Arg Val Val Pro Leu Thr Thr Tyr Cys Leu Thr Gly Leu Trp Pro Phe
785                 790                 795                 800

Cys Leu Leu Leu Met Ala Leu Pro Arg Gln Ala Tyr Ala Tyr Asp Ala
            805                 810                 815

Pro Val His Gly Gln Ile Gly Val Gly Leu Leu Ile Leu Thr Leu
            820                 825                 830

Phe Thr Leu Thr Pro Gly Tyr Lys Thr Leu Leu Gly Gln Cys Leu Trp
            835                 840                 845

Trp Leu Cys Tyr Leu Leu Thr Leu Gly Glu Ala Met Ile Gln Glu Trp
            850                 855                 860

Val Pro Pro Met Gln Val Arg Gly Gly Arg Asp Gly Ile Ala Trp Ala
865                 870                 875                 880

Val Thr Ile Phe Cys Pro Gly Val Val Phe Asp Ile Thr Lys Trp Leu
            885                 890                 895

Leu Ala Leu Leu Gly Pro Ala Tyr Leu Leu Arg Ala Ala Leu Thr His
            900                 905                 910

Val Pro Tyr Phe Val Arg Ala His Ala Leu Ile Arg Val Cys Ala Leu
            915                 920                 925

Val Lys Gln Leu Ala Gly Gly Arg Tyr Val Gln Val Ala Leu Leu Ala
            930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
            965                 970                 975

Pro Ile Ile Phe Ser Pro Met Glu Lys Lys Val Ile Val Trp Gly Ala
            980                 985                 990

Glu Thr Ala Ala Cys Gly Asp Ile Leu His Gly Leu Pro Val Ser Ala
            995                 1000                1005

Arg Leu Gly Gln Glu Ile Leu Leu Gly Pro Ala Asp Gly Tyr Thr
            1010                1015                1020

Ser Lys Gly Trp Lys Leu Leu Ala Pro Ile Thr Ala Tyr Ala Gln
            1025                1030                1035

Gln Thr Arg Gly Leu Leu Gly Ala Ile Val Val Ser Met Thr Gly
            1040                1045                1050
```

```
Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Lys
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Ile Ser Thr Leu Lys Gly Ser Ser Gly Gly Pro Val
    1160                1165                1170

Leu Cys Pro Arg Gly His Val Val Gly Leu Phe Arg Ala Ala Val
    1175                1180                1185

Cys Ser Arg Gly Val Ala Lys Ser Ile Asp Phe Ile Pro Val Glu
    1190                1195                1200

Thr Leu Asp Val Val Thr Arg Ser Pro Thr Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Val Ala Tyr
    1235                1240                1245

Ala Ala Gln Gly Tyr Lys Val Leu Val Leu Asn Pro Ser Val Ala
    1250                1255                1260

Ala Thr Leu Gly Phe Gly Ala Tyr Leu Ser Lys Ala His Gly Ile
    1265                1270                1275

Asn Pro Asn Ile Arg Thr Gly Val Arg Thr Val Met Thr Gly Glu
    1280                1285                1290

Ala Ile Thr Tyr Ser Thr Tyr Gly Lys Phe Leu Ala Asp Gly Gly
    1295                1300                1305

Cys Ala Ser Gly Ala Tyr Asp Ile Ile Cys Asp Glu Cys His
    1310                1315                1320

Ala Val Asp Ala Thr Ser Ile Leu Gly Ile Gly Thr Val Leu Asp
    1325                1330                1335

Gln Ala Glu Thr Ala Gly Val Arg Leu Thr Val Leu Ala Thr Ala
    1340                1345                1350

Thr Pro Pro Gly Ser Val Thr Thr Pro His Pro Asp Ile Glu Glu
    1355                1360                1365

Val Gly Leu Gly Arg Glu Gly Glu Ile Pro Phe Tyr Gly Arg Ala
    1370                1375                1380

Ile Pro Leu Ser Cys Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Leu Asn Ala Val Ala Tyr Tyr Arg Gly Leu Asp Val Ser
    1415                1420                1425

Ile Ile Pro Ala Gln Gly Asp Val Val Val Val Ala Thr Asp Ala
    1430                1435                1440

Leu Met Thr Gly Tyr Thr Gly Asp Phe Asp Ser Val Ile Asp Cys
```

1445                1450                1455

Asn Val Ala Val Thr Gln Ala Val Asp Phe Ser Leu Asp Pro Thr
        1460                1465                1470

Phe Thr Ile Thr Thr Gln Thr Val Pro Gln Asp Ala Val Ser Arg
        1475                1480                1485

Ser Gln Arg Arg Gly Arg Thr Gly Arg Gly Arg Gln Gly Thr Tyr
        1490                1495                1500

Arg Tyr Val Ser Thr Gly Glu Arg Ala Ser Gly Met Phe Asp Ser
        1505                1510                1515

Val Val Leu Cys Glu Cys Tyr Asp Ala Gly Ala Ala Trp Tyr Asp
        1520                1525                1530

Leu Thr Pro Ala Glu Thr Thr Val Arg Leu Arg Ala Tyr Phe Asn
        1535                1540                1545

Thr Pro Gly Leu Pro Val Cys Gln Asp His Leu Glu Phe Trp Glu
        1550                1555                1560

Ala Val Phe Thr Gly Leu Thr His Ile Asp Ala His Phe Leu Ser
        1565                1570                1575

Gln Thr Lys Gln Ala Gly Glu Asn Phe Ala Tyr Leu Val Ala Tyr
        1580                1585                1590

Gln Ala Thr Val Cys Ala Arg Ala Lys Ala Pro Pro Pro Ser Trp
        1595                1600                1605

Asp Ala Met Trp Lys Cys Leu Ala Arg Leu Lys Pro Thr Leu Ala
        1610                1615                1620

Gly Pro Thr Pro Leu Leu Tyr Arg Leu Gly Pro Ile Thr Asn Glu
        1625                1630                1635

Val Thr Leu Thr His Pro Gly Thr Lys Tyr Ile Ala Thr Cys Met
        1640                1645                1650

Gln Ala Asp Leu Glu Val Met Thr Ser Thr Trp Val Leu Ala Gly
        1655                1660                1665

Gly Val Leu Ala Ala Val Ala Ala Tyr Cys Leu Ala Thr Gly Cys
        1670                1675                1680

Val Ser Ile Ile Gly Arg Leu His Val Asn Gln Arg Val Val Val
        1685                1690                1695

Ala Pro Asp Lys Glu Val Leu Tyr Glu Ala Phe Asp Glu Met Glu
        1700                1705                1710

Glu Cys Ala Ser Arg Ala Ala Leu Ile Glu Glu Gly Gln Arg Ile
        1715                1720                1725

Ala Glu Met Leu Lys Ser Lys Ile Gln Gly Leu Leu Gln Gln Ala
        1730                1735                1740

Ser Lys Gln Ala Gln Asp Ile Gln Pro Ala Met Gln Ala Ser Trp
        1745                1750                1755

Pro Lys Val Glu Gln Phe Trp Ala Arg His Met Trp Asn Phe Ile
        1760                1765                1770

Ser Gly Ile Gln Tyr Leu Ala Gly Leu Ser Thr Leu Pro Gly Asn
        1775                1780                1785

Pro Ala Val Ala Ser Met Met Ala Phe Ser Ala Ala Leu Thr Ser
        1790                1795                1800

Pro Leu Ser Thr Ser Thr Thr Ile Leu Leu Asn Ile Met Gly Gly
        1805                1810                1815

Trp Leu Ala Ser Gln Ile Ala Pro Pro Ala Gly Ala Thr Gly Phe
        1820                1825                1830

Val Val Ser Gly Leu Val Gly Ala Ala Val Gly Ser Ile Gly Leu
        1835                1840                1845

-continued

```
Gly Lys Val Leu Val Asp Ile Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Ser Met Glu Asp Val Ile Asn Leu Leu Pro Gly Ile Leu Ser Pro
    1880                1885                1890

Gly Ala Leu Val Val Gly Val Ile Cys Ala Ala Ile Leu Arg Arg
    1895                1900                1905

His Val Gly Pro Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Thr Glu Ser Asp Ala Ser Gln Arg Val Thr Gln Leu Leu Gly
    1940                1945                1950

Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp
    1970                1975                1980

Val Trp Asp Trp Val Cys Thr Ile Leu Thr Asp Phe Lys Asn Trp
    1985                1990                1995

Leu Thr Ser Lys Leu Phe Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
    2075                2080                2085

Val Ala Ala Ser Glu Tyr Ala Glu Val Thr Gln His Gly Ser Tyr
    2090                2095                2100

Ser Tyr Val Thr Gly Leu Thr Thr Asp Asn Leu Lys Ile Pro Cys
    2105                2110                2115

Gln Leu Pro Ser Pro Glu Phe Phe Ser Trp Val Asp Gly Val Gln
    2120                2125                2130

Ile His Arg Phe Ala Pro Thr Pro Lys Pro Phe Phe Arg Asp Glu
    2135                2140                2145

Val Ser Phe Cys Val Gly Leu Asn Ser Tyr Ala Val Gly Ser Gln
    2150                2155                2160

Leu Pro Cys Glu Pro Glu Pro Asp Ala Asp Val Leu Arg Ser Met
    2165                2170                2175

Leu Thr Asp Pro Pro His Ile Thr Ala Glu Thr Ala Ala Arg Arg
    2180                2185                2190

Leu Ala Arg Gly Ser Pro Pro Ser Glu Ala Ser Ser Ser Val Ser
    2195                2200                2205

Gln Leu Ser Ala Pro Ser Leu Arg Ala Thr Cys Thr Thr His Ser
    2210                2215                2220

Asn Thr Tyr Asp Val Asp Met Val Asp Ala Asn Leu Leu Met Glu
    2225                2230                2235
```

```
Gly Gly Val Ala Gln Thr Glu Pro Glu Ser Arg Val Pro Val Leu
    2240                2245                2250

Asp Phe Leu Glu Pro Met Ala Glu Glu Ser Asp Leu Glu Pro
    2255                2260                2265

Ser Ile Pro Ser Glu Cys Met Leu Pro Arg Ser Gly Phe Pro Arg
    2270                2275                2280

Ala Leu Pro Ala Trp Ala Arg Pro Asp Tyr Asn Pro Pro Leu Val
    2285                2290                2295

Glu Ser Trp Arg Arg Pro Asp Tyr Gln Pro Pro Thr Val Ala Gly
    2300                2305                2310

Cys Ala Leu Pro Pro Lys Lys Ala Pro Thr Pro Pro Pro Arg
    2315                2320                2325

Arg Arg Arg Thr Val Gly Leu Ser Glu Ser Thr Ile Ser Glu Ala
    2330                2335                2340

Leu Gln Gln Leu Ala Ile Lys Thr Phe Gly Gln Pro Pro Ser Ser
    2345                2350                2355

Gly Asp Ala Gly Ser Ser Thr Gly Ala Gly Ala Ala Glu Ser Gly
    2360                2365                2370

Gly Pro Thr Ser Pro Gly Glu Pro Ala Pro Ser Glu Thr Gly Ser
    2375                2380                2385

Ala Ser Ser Met Pro Pro Leu Glu Gly Glu Pro Gly Asp Pro Asp
    2390                2395                2400

Leu Glu Ser Asp Gln Val Glu Leu Gln Pro Pro Gln Gly Gly
    2405                2410                2415

Gly Val Ala Pro Gly Ser Gly Ser Gly Ser Trp Ser Thr Cys Ser
    2420                2425                2430

Glu Glu Asp Asp Thr Thr Val Cys Cys Ser Met Ser Tyr Ser Trp
    2435                2440                2445

Thr Gly Ala Leu Ile Thr Pro Cys Ser Pro Glu Glu Glu Lys Leu
    2450                2455                2460

Pro Ile Asn Pro Leu Ser Asn Ser Leu Leu Arg Tyr His Asn Lys
    2465                2470                2475

Val Tyr Cys Thr Thr Ser Lys Ser Ala Ser Gln Arg Ala Lys Lys
    2480                2485                2490

Val Thr Phe Asp Arg Thr Gln Val Leu Asp Ala His Tyr Asp Ser
    2495                2500                2505

Val Leu Lys Asp Ile Lys Leu Ala Ala Ser Lys Val Ser Ala Arg
    2510                2515                2520

Leu Leu Thr Leu Glu Glu Ala Cys Gln Leu Thr Pro Pro His Ser
    2525                2530                2535

Ala Arg Ser Lys Tyr Gly Phe Gly Ala Lys Glu Val Arg Ser Leu
    2540                2545                2550

Ser Gly Arg Ala Val Asn His Ile Lys Ser Val Trp Lys Asp Leu
    2555                2560                2565

Leu Glu Asp Pro Gln Thr Pro Ile Pro Thr Thr Ile Met Ala Lys
    2570                2575                2580

Asn Glu Val Phe Cys Val Asp Pro Ala Lys Gly Gly Lys Lys Pro
    2585                2590                2595

Ala Arg Leu Ile Val Tyr Pro Asp Leu Gly Val Arg Val Cys Glu
    2600                2605                2610

Lys Met Ala Leu Tyr Asp Ile Thr Gln Lys Leu Pro Gln Ala Val
    2615                2620                2625

Met Gly Ala Ser Tyr Gly Phe Gln Tyr Ser Pro Ala Gln Arg Val
```

```
                  2630              2635              2640
Glu Tyr Leu Leu Lys Ala Trp Ala Glu Lys Lys Asp Pro Met Gly
        2645              2650              2655
Phe Ser Tyr Asp Thr Arg Cys Phe Asp Ser Thr Val Thr Glu Arg
        2660              2665              2670
Asp Ile Arg Thr Glu Glu Ser Ile Tyr Gln Ala Cys Ser Leu Pro
        2675              2680              2685
Glu Glu Ala Arg Thr Ala Ile His Ser Leu Thr Glu Arg Leu Tyr
        2690              2695              2700
Val Gly Gly Pro Met Phe Asn Ser Lys Gly Gln Thr Cys Gly Tyr
        2705              2710              2715
Arg Arg Cys Arg Ala Ser Gly Val Leu Thr Thr Ser Met Gly Asn
        2720              2725              2730
Thr Ile Thr Cys Tyr Val Lys Ala Leu Ala Ala Cys Lys Ala Ala
        2735              2740              2745
Gly Ile Val Ala Pro Thr Met Leu Val Cys Gly Asp Asp Leu Val
        2750              2755              2760
Val Ile Ser Glu Ser Gln Gly Thr Glu Glu Asp Glu Arg Asn Leu
        2765              2770              2775
Arg Ala Phe Thr Glu Ala Met Thr Arg Tyr Ser Ala Pro Pro Gly
        2780              2785              2790
Asp Pro Pro Arg Pro Glu Tyr Asp Leu Glu Leu Ile Thr Ser Cys
        2795              2800              2805
Ser Ser Asn Val Ser Val Ala Leu Gly Pro Arg Gly Arg Arg Arg
        2810              2815              2820
Tyr Tyr Leu Thr Arg Asp Pro Thr Thr Pro Leu Ala Arg Ala Ala
        2825              2830              2835
Trp Glu Thr Val Arg His Ser Pro Ile Asn Ser Trp Leu Gly Asn
        2840              2845              2850
Ile Ile Gln Tyr Ala Pro Thr Ile Trp Val Arg Met Val Leu Met
        2855              2860              2865
Thr His Phe Phe Ser Ile Leu Met Val Gln Asp Thr Leu Asp Gln
        2870              2875              2880
Asn Leu Asn Phe Glu Met Tyr Gly Ser Val Tyr Ser Val Asn Pro
        2885              2890              2895
Leu Asp Leu Pro Ala Ile Ile Glu Arg Leu His Gly Leu Asp Ala
        2900              2905              2910
Phe Ser Met His Thr Tyr Ser His His Glu Leu Thr Arg Val Ala
        2915              2920              2925
Ser Ala Leu Arg Lys Leu Gly Ala Pro Pro Leu Arg Val Trp Lys
        2930              2935              2940
Ser Arg Ala Arg Ala Val Arg Ala Ser Leu Ile Ser Arg Gly Gly
        2945              2950              2955
Lys Ala Ala Val Cys Gly Arg Tyr Leu Phe Asn Trp Ala Val Lys
        2960              2965              2970
Thr Lys Leu Lys Leu Thr Pro Leu Pro Glu Ala Arg Leu Leu Asp
        2975              2980              2985
Leu Ser Ser Trp Phe Thr Val Gly Ala Gly Gly Gly Asp Ile Phe
        2990              2995              3000
His Ser Val Ser Arg Ala Arg Pro Arg Ser Leu Leu Phe Gly Leu
        3005              3010              3015
Leu Leu Leu Phe Val Gly Val Gly Leu Phe Leu Leu Pro Ala Arg
        3020              3025              3030
```

<210> SEQ ID NO 3
<211> LENGTH: 9678
<212> TYPE: DNA
<213> ORGANISM: Artificial
<220> FEATURE:
<223> OTHER INFORMATION: JFH1 variant
<220> FEATURE:
<223> OTHER INFORMATION: JFH1-A/WT

<400> SEQUENCE: 3

| | | | | | |
|---|---|---|---|---|---|
| acctgcccct | aatagggggcg | acactccgcc | atgaatcact | cccctgtgag | gaactactgt | 60 |
| cttcacgcag | aaagcgccta | gccatggcgt | tagtatgagt | gtcgtacagc | ctccaggccc | 120 |
| cccctcccg | ggagagccat | agtggtctgc | ggaaccggtg | agtgcaccgg | aattgccggg | 180 |
| aagactgggt | cctttcttgg | atacacccac | tctatgcccg | ccatttggg | cgtgcccccg | 240 |
| caagactgct | agccgagtag | cgttgggttg | cgaaaggcct | tgtggtactg | cctgataggg | 300 |
| cgcttgcgag | tgccccggga | ggtctcgtag | accgtgcacc | atgagcacaa | atcctaaacc | 360 |
| tcaaagaaaa | accaaaagaa | acaccaaccg | tcgcccagaa | gacgttaagt | tcccgggcgg | 420 |
| cggccagatc | gttggcggag | tatacttgtt | gccgcgcagg | ggccccaggt | tgggtgtgcg | 480 |
| cacgacaagg | aaaacttcgg | agcggtccca | gccacgtggg | agacgccagc | ccatccccaa | 540 |
| agatcggcgc | tccactggca | cggcctgggg | taaaccaggt | cgccctggc | ccctatatgg | 600 |
| gaatgaggga | ctcggctggg | caggatggct | cctgtccccc | cgaggctctc | gcccctcctg | 660 |
| gggcccccact | gacccccggc | ataggtgcgc | caacgtgggt | aaagtcatcg | acaccctaac | 720 |
| gtgtggcttt | gccgacctca | tgggtgacat | ccccgtcgta | ggcgccccgc | ttagtggcgc | 780 |
| cgccagagct | gtcgcgcacg | gcgtgagagt | cctggaggac | ggggttaatt | atgcaacagg | 840 |
| gaacctacct | ggtttcccct | tttctatctt | cttgctggcc | ctgttgtcct | gcatcaccgt | 900 |
| tccggtctct | gctgcccagg | tgaagaatac | cagtagcagc | tacatggtga | ccaatgactg | 960 |
| ctccaatgac | agcatcactt | ggcagctcga | ggctgcggtt | tccacgtcc | ccgggtgcgt | 1020 |
| cccgtgcgag | agagtgggga | atacgtcacg | tgttgggtg | ccagtctcgc | caaacatggc | 1080 |
| tgtgcggcag | cccggtgccc | tcacgcaggg | tctgcgacg | cacatcgata | tggttgtgat | 1140 |
| gtccgccacc | ttctgctctg | ctctctacgt | gggggacctc | tgtggcgggg | tgatgctcgc | 1200 |
| ggcccaggtg | ttcatcgtct | cgccgcagca | ccactggttt | gtgcaggaat | gcaattgctc | 1260 |
| catctaccct | ggcaccatca | ctggacaccg | catggcatgg | gacatgatga | tgaactggtc | 1320 |
| gcccacgacc | accatgatcc | tggcgtacgt | gatgcgcgtc | cccgaggtca | tcatagacat | 1380 |
| cgttagcggg | gctcactggg | gcgtcatgtt | cggcttggcc | tacttctcta | tgcagggagc | 1440 |
| gtgggcgaag | gtcattgtca | tccttctgct | ggccgctggg | gtggacgcgg | gcaccaccac | 1500 |
| cgttggaggc | gccgttgcac | gtcccaccaa | cgtgattgcc | ggcgtgttca | gccatggccc | 1560 |
| tcagcagaac | attcagctca | ttaacaccag | cggcagttgg | cacatcaacc | gtactgcctt | 1620 |
| gaattgcaat | gactccttga | acaccggctt | tctcgcggcc | ttgttctaca | ccaaccgctt | 1680 |
| taactcgtca | gggtgtccag | ggcgcctgtc | cgcctgccgc | aacatcgagg | ctttccggat | 1740 |
| agggtgggc | accctacagt | acgaggataa | tgtcaccaat | ccagagggta | tgaggccgta | 1800 |
| ctgctggcac | taccccccaa | agccgtgtgg | cgtagtcccc | acgaggtctg | tgtgtggccc | 1860 |
| agtgtactgt | ttcaccccca | gcccggtagt | agtgggcacg | accgacagac | gtggagtgcc | 1920 |
| cacctacaca | tgggggagaga | atgagacaga | tgtcttccta | ctgaacagca | cccgaccgcc | 1980 |

```
gcagggctca tggttcggct gcacgtggat gaactccact ggtttcacca agacttgtgg    2040
cgcgccacct tgccgcacca gagctgactt caacgccagc acggacttgt tgtgccctac    2100
ggattgtttt aggaagcatc ctgatgccac ttatattaag tgtggttctg ggccctggct    2160
cacaccaaag tgcctggtcc actaccctta cagactctgg cattacccct gcacagtcaa    2220
ttttaccatc ttcaagataa gaatgtatgt aggggggtt gagcacaggc tcacggccgc     2280
atgcaacttc actcgtgggg atcgctgcga cttggaggac agggacagga gtcagctgtc    2340
tcctctgttg cactctacca cggaatgggc catcctgccc tgcacctact cagacttacc    2400
cgctttgtca actggtcttc tccaccttca ccagaacatc gtggacgtac aatacatgta    2460
tggcctctca cctgctatca caaaatacgt cgttcgatgg gagtgggtgg tactcttatt    2520
cctgctctta gcggacgcca gagtctgcgc ctgcttgtgg atgctcatct tgttgggcca    2580
ggccgaagca gcattggaga agttggtcgt cttgcacgct gcgagtgcgg ctaactgcca    2640
tggcctccta tattttgcca tcttcttcgt ggcagcttgg cacatcaggg gtcgggtggt    2700 cccttgacc acctattgcc ttactggcct atggcccttc tgcctactgc tcatggcact     2760
gccccggcag gcttatgcct atgacgcacc tgtgcacgga cagataggcg tgggtttgtt    2820
gatattgatc accctcttca cactcacccc ggggtataag accctcctcg gccagtgtct    2880
gtggtggttg tgctatctcc tgaccctggg ggaagccatg attcgggagt gggtaccacc    2940
catgcaggtg cgcggcggcc gcgatggcat cgcgtgggcc gtcactatat ctgcccggg     3000 cgtggtgttt gacattacca aatggctttt ggcgttgctt gggcctgctt acctcttaag    3060
ggccgctttg acccatgtgc cgtacttcgt cagagctcac gctctgataa gggtatgcgc    3120
tttggtgaag cggctcgcgg ggggtaggta tgttcaggtg gcgctgttgg cccttggcag    3180
gtggactggc acctacatct atgaccacct cacacctatg gcggactggg ccgctagcgg    3240
cctgcgcgac ttagcggtcg ccgtggaacc catcatcttc agtccgatgg agaagaaggt    3300
catcgtctgg ggagcggaga cggctgcatg tggggacatt ctacatggac ttcccgtgtc    3360
cgcccgactc ggccaggaga tcctcctcgg cccagctgat ggctacacct caaggggtg     3420 gaagctcctt gctcccatca ctgcttatgc ccagcaaaca cgaggcctcc tgggcgccat    3480
agtggtgagt atgacggggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acgaggtccg gtcacgcaga tgtactcgag    3660
tgctgagggg gacttggtag gctggcccag ccccccctggg accaagtctt ggagccgtg    3720 caagtgtgga gccgtcgacc tatatctggt cacgcggaac gctgatgtca tcccggctcg    3780
gagacgcggg gataagcggg gagcattgct ctccccgaga cccatttcga ccttgaaggg    3840
gtcctcgggg gggccggtgc tctgccctag gggccacgtc gttgggctct ccgagcagc    3900 tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca agtactagt gcttaacccc tcggtagctg ccaccctggg    4140 gtttgggcg tacctatcca aggcacatgg catcaatccc aacattagga ctggagtcag     4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg gaacggtcct tgatcaagca gagacagccg gggtcagact    4380
```

-continued

```
aactgtgctg gctacggcca cacccccgg gtcagtgaca acccccccatc ccgatataga    4440
agaggtaggc ctcgggcggg agggtgagat ccccttctat gggagggcga ttcccctatc    4500
ctgcatcaag ggagggagac acctgatttt ctgccactca agaaaaagt gtgacgagct     4560
cgcggcggcc cttcggggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag acgctgtctc    4800
acgcagtcag cgccgcgggc gcacaggtag aggaagacag ggcacttata ggtatgtttc    4860
cactggtgaa cgagcctcag gaatgtttga cagtgtagtg ctttgtgagt gctacgacgc    4920
aggggctgcg tggtacgatc tcacaccagc ggagaccacc gtcaggctta gagcgtatt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtaccta gtagcctacc aagctacggt gtgcgccaga gccaaggccc ctccccgtc    5160
ctgggacgcc atgtggaagt gcctggcccg actcaagcct acgcttgcgg gccccacacc    5220
tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctggcagccg tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcggct ctcatcgaag aggggcagcg    5520
gatagccgag atgttgaagt ccaagatcca aggcttgctg cagcaggcct ctaagcaggc    5580
ccaggacata caacccgcta tgcaggcttc atggccccaaa gtggaacaat tgggccag    5640
acacatgtgg aacttcatta gcggcatcca atacctcgca ggattgtcaa cactgccagg    5700
gaaccccgcg gtggcttcca tgatggcatt cagtgccgcc ctcaccagtc cgttgtcgac    5760
cagtaccacc atccttctca acatcatggg aggctggtta gcgtcccaga tcgcaccacc    5820
cgcggggcc accggctttg tcgtcagtgg cctggtgggg gctgccgtgg gcagcatagg    5880
cctgggtaag gtgctggtgg acatcctggc aggatatggt gcgggcattt cgggggccct    5940
cgtcgcattc aagatcatgt ctggcgagaa gccctctatg gaagatgtca tcaatctact    6000
gcctgggatc ctgtctccgg gagccctggt ggtgggggtc atctgcgcgg ccattctgcg    6060
ccgccacgtg ggaccggggg agggcgcggt ccaatggatg aacaggctta ttgccttgc    6120
ttccagagga aaccacgtcg cccctactca ctacgtgacg gagtcggatg cgtcgcagcg    6180
tgtgacccaa ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360
gcccggcctc cccttcatct cttgtcaaaa ggggtacaag ggtgtgtggg ccggcactgg    6420
catcatgacc acgcgctgcc cttgcggcgc caacatctct ggcaatgtcc gcctgggctc    6480
tatgaggatc acagggccta aaacctgcat gaacacctgg caggggacct ttcctatcaa    6540
ttgctacacg gagggccagt gcgcgccgaa acccccacg aactacaaga ccgccatctg    6600
gagggtggcg gcctcggagt acgcggaggt gacgcagcat gggtcgtact cctatgtaac    6660
aggactgacc actgacaatc tgaaaattcc ttgccaacta ccttctccag agttttctc    6720
```

```
ctgggtggac ggtgtgcaga tccataggtt tgcacccaca ccaaagccgt ttttccggga    6780
tgaggtctcg ttctgcgttg ggcttaattc ctatgctgtc gggtcccagc ttccctgtga    6840
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260
accgcccacc gttgctggtt gtgctctccc ccccccaag aaggcccga cgcctccccc      7320 aaggagacgc cggacagtgg gtctgagcga gagcaccata tcagaagccc tccagcaact    7380
ggccatcaag acctttggcc agccccctc gagcggtgat gcaggctcgt ccacgggggc     7440
gggcgccgcc gaatccggcg gtccgacgtc ccctggtgag ccggccccct cagagacagg    7500
ttccgcctcc tctatgcccc ccctcgaggg ggagcctgga gatccggacc tggagtctga    7560
tcaggtagag cttcaacctc cccccaggg gggggggta gctcccggtt cgggctcggg      7620
gtcttggtct acttgctccg aggaggacga taccaccgtg tgctgctcca tgtcatactc    7680
ctggaccggg gctctaataa ctccctgtag ccccgaagag gaaaagttgc caatcaaccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccacccca ttctgcaaga tccaagtatg gattcggggc    7980
caaggaggtc cgcagcttgt ccgggagggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggcccc tatgacatt acacaaaagc ttcctcaggc     8220
ggtaatggga gcttcctatg gcttccagta ctcccctgcc caacgggtgg agtatctctt    8280
gaaagcatgg gcgaaaaga aggaccccat gggttttttcg tatgatacc gatgcttcga     8340 ctcaaccgtc actgagagag acatcaggac cgaggagtcc atataccagg cctgctccct    8400
gcccgaggag gcccgcactg ccatacactc gctgactgag agactttacg taggagggcc    8460
catgttcaac agcaagggtc aaacctgcgg ttacagacgt tgccgcgcca gcggggtgct    8520
aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640
aagccagggg actgaggagg acgagcggaa cctgagagcc ttcacggagg ccatgaccag    8700
gtactctgcc cctcctggtg atccccccag accggaatat gacctggagc taataacatc    8760
ctgttcctca aatgtgtctg tggcgttggg cccgcggggc cgccgcagat actacctgac    8820
cagagaccca accactccac tcgcccgggc tgcctgggaa acagttagac actcccctat    8880
caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tcctttggac cttccagcca taattgagag    9060
gttacacggg cttgacgcct tttctatgca cacatactct caccacgaac tgacgcgggt    9120
```

```
ggcttcagcc ctcagaaaac ttggggcgcc acccctcagg gtgtggaaga gtcgggctcg      9180
cgcagtcagg gcgtccctca tctcccgtgg agggaaagcg gccgtttgcg gccgatatct      9240
cttcaattgg gcggtgaaga ccaagctcaa actcactcca ttgccggagg cgcgcctact      9300
ggacttatcc agttggttca ccgtcggcgc cggcgggggc gacattttc acagcgtgtc       9360 gcgcgcccga ccccgctcat tactcttcgg cctactccta cttttcgtag gggtaggcct      9420
cttcctactc cccgctcggt agagcggcac acactaggta cactccatag ctaactgttc      9480
cttttttttt tttttttttt tttttttttt tttttttttt ttttcttttt ttttttttc      9540 cctctttctt cccttctcat cttattctac tttctttctt ggtggctcca tcttagccct      9600
agtcacggct agctgtgaaa ggtccgtgag ccgcatgact gcagagagtg ccgtaactgg      9660
tctctctgca gatcatgt                                                    9678

<210> SEQ ID NO 4
<211> LENGTH: 9678
<212> TYPE: DNA
<213> ORGANISM: Artificial
<220> FEATURE:
<223> OTHER INFORMATION: JFH1 variant
<220> FEATURE:
<223> OTHER INFORMATION: JFH1-B/WT

<400> SEQUENCE: 4
acctgcccct aatagggcg acactccgcc atgaatcact cccctgtgag gaactactgt         60
cttcacgcag aaagcgccta gccatggcgt tagtatgagt gtcgtacagc ctccaggccc       120
ccccctcccg ggagagccat agtggtctgc ggaaccggtg agtacaccgg aattgccggg       180
aagactgggt cctttcttgg ataaacccac tctatgcccg gccatttggg cgtgcccccg       240
caagactgct agccgagtag cgttgggttg cgaaaggcct tgtggtactg cctgataggg       300
cgcttgcgag tgccccggga ggtctcgtag accgtgcacc atgagcacaa atcctaaacc       360
tcaaagaaaa accaaaagaa acaccaaccg tcgcccagaa gacgttaagt tcccgggcgg       420
cggccagatc gctggcggag tatacttgtt gccgcgcagg ggccccaggt tgggtgtgcg       480
cacgacaagg aaaacttcgg agcggtccca gccacgtggg agacgccagc ccatccccaa       540
agatcggcgc tccactggca cggcctgggg aaaaccaggt cgcccctggc cctatatgg      600 gaatgaggga ctcggctggg caggatggct cctgtccccc cgaggctctc gccctcctg        660 gggccccact gaccccggc ataggtcgcg caacgtgggt aaagtcatcg acaccctaac       720
gtgtggcttt gccgacctca tggggtacat ccccgtcgta ggcgccccgc ttagtggcgc      780
cgccagagct gtcgcgcacg gcgtgagagt cctggaggac ggggttaatt atgcaacagg      840
gaacctaccc ggtttccct tttctatctt cttgctggcc ctgttgtcct gcatcaccgt       900
tccggtctct gctgcccagg tgaagaatac cagtagcagc tacatggtga ccaatgactg      960
ctccaatgac agcatcactt ggcagctcga ggctgcagtt ctccacgtcc ccgggtgcgt     1020
cccgtgcgag agagtgggga atacgtcacg gtgttgggtg ccagtctcgc caaacatggc     1080
tgtgcggcag cccggtgccc tcacgcaggg tctgcggacg cacatcgata tggttgtgat     1140
gtccgccacc ttctgctctg ctctctacgt ggggggacctc tgtggcgggg tgatgctcgc     1200
ggcccaggtg ttcatcgtct cgccgcagta ccactggttt gtgcaggaat gcaattgctc     1260
catctacccc ggcaccatca ctggacaccg catggcatgg acatgatga tgaactggtc      1320 gcccacggcc accatgatcc tggcgtacgt gatgcgcgtc cccgaggtca tcatagacat     1380
```

```
cgttagcggg gctcactggg gcgtcatgtt cggcttggcc tacttctcta tgcagggagc   1440
gtgggcgaag gtcattgtca tccttctgct ggccgctggg gtggacgcgg gcaccaccac   1500
cgttggggc gctgttgcac gttccaccaa cgtgattgcc ggcgtgttca gccatggccc    1560
tcagcagaac attcagctca ttaacaccaa cggcagctgg cacatcaacc gtactgcctt   1620
gaattgcaat gactccttga acaccggctt tctcgcggcc ttgttctaca ccaaccgctt   1680
taactcgtca aggtgtccag ggcgcctgtc cgcctgccgc aacatcgagg ctttccggat   1740
agggtggggc accctacagt acgaggataa tgtcaccaat ccagaggata tgaggccgta   1800
ctgctggcac taccccccaa agccgtgtgg cgtagtcccc gcgaggtctg tgtgtggccc   1860
agtgtactgt ttcactccca gcccggtagt agtgggcacg accgacagac gtggagtgcc   1920
cacctacaca tggggagaga atgagacaga tgtcttccta ctgaacagca cccgaccgcc   1980
acagggctca tggttcggct gcacgtggat gaactccact ggtttcacca agacttgtgg   2040
cgcgccacct gccgcacca gagctgactt caacgccagc acggacttgt tgtgccctac    2100
ggattgtttt aggaagcatc ctgatgccac ttatattaag tgtggttctg ggccctggct   2160
cacaccaaag tgcctggtcc actacccta cagactctgg cattacccct gcacagtcaa    2220
ttttaccatc ttcaagataa gaatgtatgt aggggggtt gagcacaggc tcacggccgc    2280
atgcaacttc actcgtgggg atcgctgcga cttggaggac agggacagga gtcagctgtc   2340
tcctctgttg cactctacca cggaatgggc catcctgccc tgcacctact cagacttacc   2400
cgctttgtca actggtcttc tccaccttca ccagaacatc gtggacgtac aatacatgta   2460
tggcctctca cctgctatca caaaatacgt cgttcgatgg gagtgggtgg tactcttatt   2520
cctgctctta gcggacgcca gagtctgcgc ctgcctgtgg atgctcatct tgttgggcca   2580
ggccgaagca gcattggaga agttggccgt cttgcacgct cgagtgcgg ctaactgcca    2640
tggcctccta tattttgcca tcttcttcgt ggcagcttgg cacatcaggg gtcgggcggt   2700
cccttgacc acctattgcc tcactggcct atggcccttc tgcctactgc tcatggcact    2760
gcccggcag gcttatgcct atgacgcacc tgtgcacgga cagataggcg tgggtttgtt    2820
gatattgatc accctcttca cactcacccc ggggtataag accctcctcg gccagtgtct   2880
gtggtggttg tgctatctcc tgaccctggg ggaagccatg attcgggagt gggtaccacc   2940
catgcaggtg cgcggcggcc gcgatggcat cgcgtgggcc gtcactatat ctgcccggg    3000
tgtggtgttt gacattacca aatggctttt ggcgttgctt gggcctgctt acctcttaag   3060
ggccgctttg acacatgtgc cgtacttcgt cagagctcac gctctgataa gggtatgcgc   3120
tttggtgaag cagctcgcgg ggggtaggta tgttcaggtg gcgctattgg cccttggcag   3180
gtggactggc acctacatct atgaccacct cacacctatg tcggactggg ccgctagcgg   3240
cctgcgcgac ttagcggtcg ccgtggaacc catcatcttc agtccgatgg agaagaaggt   3300
catcgtctgg ggagcggaga cggctgcatg tggggacatt ctacatggac ttcccgtgtc   3360
cgcccgactc ggccaggaga tcctcctcgg cccagctgat ggctacacct caagggtg    3420
gaagctcctt gctcccatca ctgcttatgc ccagcaaaca cgaggcctcc tgggcgccat   3480
agtggtgagt atgacggggc gtgacaggac agaacaggcc ggggaagtcc aaatcctgtc   3540
cacagtctct cagtccttcc tcggaacaac catctcgggg gttttgtgga ctgtttacca   3600
cggagctggc aacaagactc tagccggctt acggggtccg gtcacgcaga tgtactcgag   3660
tgctgagggg gacttggtag ctggcccag ccccccctggg accaagtctt ggagccgtg    3720
caagtgtgga gccgtcgacc tatatctggt cacgcgaac gctgatgtta tcccggctcg    3780
```

```
gagacgcggg gacaagcggg gagcattgct ctccccgaga cccatttcga ccttgaaggg    3840
gtcctcgggg gggccggtgc tctgccctag gggccacgtc gttgggctct tccgagcagc    3900
tgtgtgctct cggggcgtgg ccaaatccat cgatttcatc cccgttgaga cactcgacgt    3960
tgttacaagg tctcccacct tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca aagtactagt gcttaacccc tcggtagctg ccaccctggg    4140
gtttggggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg aacggtcct tgatcaagca gagacagccg ggtcagact     4380 aactgtgctg gctacggcca cacccccgg gtcagtgaca accccccatc ccgatataga    4440
agaggtaggc ctcgggcggg agggtgagat ccccttctat ggagggcga ttcccctatc     4500 ctgcatcaag ggagggagac acctgatttt ctgccactca agaaaaagt gtgacgagct    4560 cgcggcggcc cttcggggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag acgctgtctc    4800
acgcagtcag cgccgcgggc gcacaggtag aggaagacag ggcacttata ggtatgtttc    4860
cactggtgaa cgagcctcag gaatgtttga cagtgtagtg ctttgtgagt gctacgacgc    4920
aggggctgcg tggtacgatc tcacaccagc ggagaccacc gtcaggctta gagcgtattt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtacctg gtagcctacc aagctacggt gtgcgccaga gccaaggccc ctcccccgtc    5160 ctggacgcc atgtgaagt gcctggcccg actcaagcct acgcttgcgg gccccacacc     5220
tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctggcagccg tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcggct ctcatcgaag aggggcagcg    5520
gatagccgag atgttgaagt ccaagatcca aggcttgctg cagcaggcct ctaagcaggc    5580
ccaggacata caacccgcta tgcaggcttc atggcccaaa gtggaacaat tttgggccag    5640
acacatgtgg aacttcatta gcggcatcca atacctcgca ggattgtcaa cactgccagg    5700 gaacccgcg gtggcttcca tgatggcatt cagtgccgcc ctcaccagtc cgttgtcgac    5760
cagtaccacc atccttctca acatcatggg aggctggtta gcgtcccaga tcgcaccacc    5820
cgcgggggcc accggctttg tcgtcagtgg cctggtgggg gctgccgtgg cagcatagg    5880 cctgggtaag gtgctggtgg acatcctggc aggatatggt gcgggcattt cggggggcct    5940
cgtcgcattc aagatcatgt ctggcgagaa gccctctatg aagatgtca tcaatctact     6000 gcctgggatc ctgtctccgg gagccctggt ggtgggggtc atctgcgcgg ccattctgcg    6060
ccgccacgtg ggaccggggg agggcgcggt ccaatggatg aacaggctta ttgcctttgc    6120
```

```
ttccagagga aaccacgtcg cccctactca ctacgtgacg gagtcggatg cgtcgcagcg    6180
tgtgacccaa ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360
gcccggcctc cccttcatct cttgtcaaaa ggggtacaag ggtgtgtggg ccggcactgg    6420
catcatgacc acgcgctgcc cttgcggcgc caacatctct ggcaatgtcc gcctgggctc    6480
tatgaggatc acagggccta aaacctgcat gaacacctgg caggggacct tcctatcaa    6540
ttgctcacg gagggccagt gcgcgccgaa acccccacg aactacaaga ccgccatctg    6600
gagggtggcg gcctcggagt acgcggaggt gacgcagcat gggtcgtact cctatgtaac    6660
aggactgacc actgacaatc tgaaaattcc ttgccaacta ccttctccag agttttctc    6720
ctgggtggac ggtgtgcaga tccataggtt tgcacccaca ccaaagccgt ttttcgggga    6780
tgaggtctcg ttctgcgttg ggcttaattc ctatgctgtc gggtcccagc ttccctgtga    6840
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260
accgcccacc gttgctggtt gtgctctccc ccccccaag aaggccccga cgcctccccc    7320
aaggagacgc cggacagtgg gtctgagcga gagcaccata tcagaagccc tccagcaact    7380
ggccatcaag accttttggcc agcccccctc gagcggtgat gcaggctcgt ccacggggc    7440
gggcgccgcc gaatccggcg gtccgacgtc ccctggtgag ccggcccct cagagacagg    7500
ttccgcctcc tctatgcccc cctcgaggg ggagcctgga gatccggacc tggagtctga    7560
tcaggtagag cttcaacctc ccccccaggg ggggggggta gctcccggtt cgggctcggg    7620
gtcttggtct acttgctccg aggaggacga taccaccgtg tgctgctcca tgtcatactc    7680
ctggaccggg gctctaataa ctccctgtag ccccgaagag gaaaagttgc aatcaacccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggagggcg tgccagttga ctccacccca ttctgcaaga tccaagtatg gattcggggc    7980
caaggaggtc cgcagcttgt ccgggagggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg gcttccagta ctcccctgcc caacgggtgg agtatctctt    8280
gaaagcatgg gcggaaaaga aggaccccat gggttttttcg tatgatacccc gatgcttcga    8340
ctcaaccgtc actgagagag acatcaggac cgaggagtcc atataccagg cctgctccct    8400
gccccgaggag gcccgcactg ccatacactc gctgactgag agactttacg taggagggcc    8460
catgttcaac agcaagggtc aaacctgcgg ttacagacgt tgccgcgcca gcggggtgct    8520
```

| | |
|---|---:|
| aaccactagc atgggtaaca ccatcacatg ctatgtgaaa gccctagcgg cctgcaaggc | 8580 |
| tgcggggata gttgcgccca caatgctggt atgcggcgat gacctagtag tcatctcaga | 8640 |
| aagccagggg actgaggagg acgagcggaa cctgagagcc ttcacggagg ccatgaccag | 8700 |
| gtactctgcc cctcctggtg atccccccag accggaatat gacctggagc taataacatc | 8760 |
| ctgttcctca aatgtgtctg tggcgttggg cccgcggggc cgccgcagat actacctgac | 8820 |
| cagagaccca accactccac tcgcccgggc tgcctgggaa acagttagac actcccctat | 8880 |
| caattcatgg ctgggaaaca tcatccagta tgctccaacc atatgggttc gcatggtcct | 8940 |
| aatgacacac ttcttctcca ttctcatggt ccaagacacc ctggaccaga acctcaactt | 9000 |
| tgagatgtat ggatcagtat actccgtgaa tcctttggac cttccagcca taattgagag | 9060 |
| gttacacggg cttgacgcct tttctatgca cacatactct caccacgaac tgacgcgggt | 9120 |
| ggcttcagcc ctcagaaaac ttggggcgcc acccctcagg gtgtggaaga gtcgggctcg | 9180 |
| cgcagtcagg gcgtccctca tctcccgtgg agggaaagcg gccgtttgcg gccgatatct | 9240 |
| cttcaattgg gcggtgaaga ccaagctcaa actcactcca ttgccggagg cgcgcctact | 9300 |
| ggacttatcc agttggttca ccgtcggcgc cggcgggggc gacatttttc acagcgtgtc | 9360 |
| gcgcgcccga ccccgctcat tactcttcgg cctactccta cttttcgtag gggtaggcct | 9420 |
| cttcctactc cccgctcggt agagcggcac acactaggta cactccatag ctaactgttc | 9480 |
| cttttttttt tttttttttt tttttttttt tttttttttt ttttcttttt tttttttttc | 9540 |
| cctctttctt cccttctcat cttattctac tttctttctt ggtggctcca tcttagccct | 9600 |
| agtcacggct agctgtgaaa ggtccgtgag ccgcatgact gcagagagtg ccgtaactgg | 9660 |
| tctctctgca gatcatgt | 9678 |

<210> SEQ ID NO 5
<211> LENGTH: 9678
<212> TYPE: DNA
<213> ORGANISM: Artificial
<220> FEATURE:
<223> OTHER INFORMATION: JFH1 variant
<220> FEATURE:
<223> OTHER INFORMATION: JFH1-Q862R

<400> SEQUENCE: 5

| | |
|---|---:|
| acctgcccct aatagggggcg acactccgcc atgaatcact cccctgtgag gaactactgt | 60 |
| cttcacgcag aaagcgccta gccatggcgt tagtatgagt gtcgtacagc ctccaggccc | 120 |
| cccccctcccg ggagagccat agtggtctgc ggaaccggtg agtacaccgg aattgccggg | 180 |
| aagactgggt cctttcttgg ataaacccac tctatgcccg gccatttggg cgtgcccccg | 240 |
| caagactgct agccgagtag cgttgggttg cgaaaggcct tgtggtactg cctgataggg | 300 |
| cgcttgcgag tgccccggga ggtctcgtag accgtgcacc atgagcacaa atcctaaacc | 360 |
| tcaaagaaaa accaaaagaa acaccaaccg tcgcccagaa gacgttaagt tcccgggcgg | 420 |
| cggccagatc gttggcggag tatacttgtt gccgcgcagg ggccccaggt tgggtgtgcg | 480 |
| cacgacaagg aaaacttcgg agcggtccca gccacgtggg agacgccagc ccatccccaa | 540 |
| agatcggcgc tccactggca aggcctgggg aaaaccaggt cgcccctggc ccctatatgg | 600 |
| gaatgaggga ctcggctggg caggatggct cctgtccccc cgaggctctc gcccctcctg | 660 |
| gggcccccact gaccccggc ataggtcgcg caacgtgggg aaagtcatcg acaccctaac | 720 |
| gtgtggcttt gccgacctca tggggtacat ccccgtcgta ggcgccccgc ttagtggcgc | 780 |

```
cgccagagct gtcgcgcacg gcgtgagagt cctggaggac ggggttaatt atgcaacagg      840
gaacctaccc ggtttcccct tttctatctt cttgctggcc ctgttgtcct gcatcaccgt      900
tccggtctct gctgcccagg tgaagaatac cagtagcagc tacatggtga ccaatgactg      960
ctccaatgac agcatcactt ggcagctcga ggctgcggtt ctccacgtcc ccgggtgcgt     1020
cccgtgcgag agagtgggga atacgtcacg gtgttgggtg ccagtctcgc caaacatggc     1080
tgtgcggcag cccggtgccc tcacgcaggg tctgcggacg cacatcgata tggttgtgat     1140
gtccgccacc ttctgctctg ctctctacgt gggggacctc tgtggcgggg tgatgctcgc     1200
ggcccaggtg ttcatcgtct cgccgcagta ccactggttt gtgcaagaat gcaattgctc     1260
catctaccct ggcaccatca ctggacaccg catggcatgg acatgatga tgaactggtc      1320 gcccacggcc accatgatcc tggcgtacgt gatgcgcgtc cccgaggtca tcatagacat     1380
cgttagcggg gctcactggg gcgtcatgtt cggcttggcc tacttctcta tgcagggagc     1440
gtgggcgaag gtcattgtca tccttctgct ggccgctggg gtggacgcgg gcaccaccac     1500
cgttggaggc gctgttgcac gttccaccaa cgtgattgcc ggcgtgttca gccatggccc     1560
tcagcagaac attcagctca ttaacaccaa cggcagttgg cacatcaacc gtactgcctt     1620
gaattgcaat gactccttga acaccggctt tctcgcggcc ttgttctaca ccaaccgctt     1680
taactcgtca gggtgtccag ggcgcctgtc cgcctgccgc aacatcgagg ctttccggat     1740
agggtggggc accctacagt acgaggataa tgtcaccaat ccagaggata tgaggccgta     1800
ctgctggcac tacccccaa agccgtgtgg cgtagtcccc gcgaggtctg tgtgtggccc      1860
agtgtactgt ttcacccca gcccggtagt agtgggcacg accgacagac gtggagtgcc      1920
cacctacaca tggggagaga atgagacaga tgtcttccta ctgaacagca cccgaccgcc     1980
gcagggctca tggttcggct gcacgtggat gaactccact ggtttcacca agacttgtgg     2040
cgcgccacct tgccgcacca gagctgactt caacgccagc acggacttgt tgtgccctac     2100
ggattgtttt aggaagcatc ctgatgccac ttatattaag tgtggttctg ggcctggct      2160 cacaccaaag tgcctggtcc actaccctta cagactctgg cattaccct gcacagtcaa      2220 ttttaccatc ttcaagataa gaatgtatgt aggggggggtt gagcacaggc tcacggccgc     2280
atgcaacttc actcgtgggg atcgctgcga cttggaggac agggacagga gtcagctgtc     2340
tcctctgttg cactctacca cggaatgggc catcctgccc tgcacctact cagacttacc     2400
cgctttgtca actggtcttc tccaccttca ccagaacatc gtggacgtac aatacatgta     2460
tggcctctca cctgctatca caaatacgt cgttcgatgg gagtgggtgg tactcttatt      2520
cctgctctta gcggacgcca gagtctgcgc ctgcttgtgg atgctcatct tgtttgggcca    2580 ggccgaagca gcattggaga agttggtcgt cttgcacgct gcgagtgcgg ctaactgcca     2640
tggcctccta tattttgcca tcttcttcgt ggcagcttgg cacatcaggg tcgggtggt      2700 cccttgacc acctattgcc tcactggcct atgcccttc tgcctactgc tcatggcact       2760
gccccggcag gcttatgcct atgacgcacc tgtgcacgga cagataggcg tgggtttgtt      2820
gatattgatc ccctcttca cactcacccc ggggtataag accctcctcg gccagtgtct      2880
gtggtggttg tgctatctcc tgaccctggg ggaagccatg attcgggagt gggtaccacc      2940
catgcaggtg cgcggcggcc gcgatggcat cgcgtgggcc gtcactatat tctgcccggg      3000
tgtggtgttt gacattacca aatggctttt ggcgttgctt gggcctgctt acctcttaag     3060
ggccgctttg acacatgtgc cgtacttcgt cagagctcac gctctgataa gggtatgcgc     3120
tttggtgaag cagctcgcgg ggggtaggta tgttcaggtg gcgctattgg cccttggcag     3180
```

```
gtggactggc acctacatct atgaccacct cacacctatg tcggactggg ccgctagcgg    3240
cctgcgcgac ttagcggtcg ccgtggaacc catcatcttc agtccgatgg agaagaaggt    3300
catcgtctgg ggagcggaga cggctgcatg tggggacatt ctacatggac ttcccgtgtc    3360
cgcccgactc ggccaggaga tcctcctcgg cccagctgat ggctacacct ccaagggtg    3420 gaagctcctt gctcccatca ctgcttatgc ccagcaaaca cgaggcctcc tgggcgccat    3480
agtggtgagt atgacgggc gtgacaggac agaacaggcc gggaagtcc aaatcctgtc    3540 cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag ctggcccag ccccctggg accaagtctt tggagccgtg    3720
caagtgtgga gccgtcgacc tatatctggt cacgcggaac gctgatgtca tcccggctcg    3780
gagacgcggg gacaagcggg gagcattgct ctccccgaga cccatttcga ccttgaaggg    3840
gtcctcgggg gggccggtgc tctgccctag gggccacgtc gttgggctct tccgagcagc    3900
tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca agtactagt gcttaacccc tcggtagctg ccaccctggg    4140 gtttgggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg aacggtcct tgatcaagca gagacagccg gggtcagact    4380
aactgtgctg gctacggcca cacccccgg gtcagtgaca acccccatc ccgatataga    4440 agaggtaggc ctcgggcggg agggtgagat ccccttctat gggagggcga ttccctatc    4500 ctgcatcaag ggagggagac acctgatttt ctgccactca agaaaaagt gtgacgagct    4560 cgcggcggcc cttcggggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag acgctgtctc    4800
acgcagtcag cgccgcgggc gcacaggtag aggaagacag ggcacttata ggtatgtttc    4860
cactggtgaa cgagcctcag gaatgtttga cagtgtagtg ctttgtgagt gctacgacgc    4920
aggggctgcg tggtacgatc tcacaccagc ggagaccacc gtcaggctta gagcgtattt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtaccta gtagcctacc aagctacggt gtgcgccaga gccaaggccc ctcccccgtc    5160
ctgggacgcc atgtggaagt gcctggccg actcaagcct acgcttgcgg ccccacacc    5220 tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctgcagcgcc tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcgggct ctcatcgaag aggggcagcg    5520
```

```
gatagccgag atgttgaagt ccaagatcca aggcttgctg cagcaggcct ctaagcaggc      5580
ccaggacata caacccgcta tgcaggcttc atgggcccaaa gtggaacaat tttgggccag     5640
acacatgtgg aacttcatta gcggcatcca atacctcgca ggattgtcaa cactgccagg     5700
gaaccccgcg gtggcttcca tgatggcatt cagtgccgcc ctcaccagtc cgttgtcgac     5760
cagtaccacc atccttctca acatcatggg aggctggtta gcgtcccaga tcgcaccacc     5820
cgcgggggcc accggctttg tcgtcagtgg cctggtgggg gctgccgtgg gcagcatagg     5880
cctgggtaag gtgctggtgg acatcctggc aggatatggt gcgggcattt cgggggccct     5940
cgtcgcattc aagatcatgt ctggcgagaa gccctctatg aagatgtca tcaatctact      6000 gcctgggatc ctgtctccgg gagccctggt ggtgggggtc atctgcgcgg ccattctgcg     6060
ccgccacgtg ggaccggggg agggcgcggt ccaatggatg aacaggctta ttgcctttgc     6120
ttccagagga aaccacgtcg cccctactca ctacgtgacg gagtcggatg cgtcgcagcg     6180
tgtgacccaa ctacttggct ctcttactat aaccagccta ctcagaagac tccacaattg     6240
gataactgag gactgcccca tcccatgctc cggatcctgg ctccgcgacg tgtgggactg     6300
ggtttgcacc atcttgacag acttcaaaaa ttggctgacc tctaaattgt tccccaagct     6360 gccccggcctc cccttcatct cttgtcaaaa ggggtacaag ggtgtgtggg ccggcactgg    6420
catcatgacc acgcgctgcc cttgcggcgc caacatctct ggcaatgtcc gcctgggctc     6480
tatgaggatc acagggccta aaacctgcat gaacacctgg caggggacct ttcctatcaa     6540
ttgctacacg gagggccagt gcgcgccgaa acccccacg aactacaaga ccgccatctg      6600
gagggtggcg gcctcggagt acgcggaggt gacgcagcat gggtcgtact cctatgtaac     6660
aggactgacc actgacaatc tgaaaattcc ttgccaacta ccttctccag agttttctc      6720 ctgggtggac ggtgtgcaga tccataggtt tgcacccaca ccaaagccgt ttttccggga     6780
tgaggtctcg ttctgcgttg ggcttaattc ctatgctgtc gggtcccagc ttccctgtga     6840
acctgagccc gacgcagacg tattgaggtc catgctaaca gatccgcccc acatcacggc     6900
ggagactgcg gcgcggcgct tggcacgggg atcacctcca tctgaggcga gctcctcagt     6960
gagccagcta tcagcaccgt cgctgcgggc cacctgcacc acccacagca acacctatga     7020
cgtggacatg gtcgatgcca acctgctcat ggagggcggt gtggctcaga cagagcctga     7080
gtccagggtg cccgttctgg actttctcga gccaatggcc gaggaagaga gcgaccttga     7140
gccctcaata ccatcggagt gcatgctccc caggagcggg tttccacggg ccttaccggc     7200
ttgggcacgg cctgactaca acccgccgct cgtggaatcg tggaggaggc cagattacca     7260 accgccacc gttgctggtt gtgctctccc cccccccaag aaggcccga cgcctccccc       7320 aaggagacgc cggacagtgg gtctgagcga gagcaccata tcagaagccc tccagcaact     7380
ggccatcaag acctttggcc agccccctc gagcggtgat gcaggctcgt ccacgggggc      7440
gggcgccgcc gaatcggcg gtccgacgtc cctggtgag ccggcccct cagagacagg       7500 ttccgcctcc tctatgcccc cctcgaggg ggagcctgga gatccggacc tggagtctga      7560
tcaggtagag cttcaaccctc cccccaggg ggggggggta gctcccggtt cgggctcggg    7620
gtcttggtct acttgctccg aggaggacga taccaccgtg tgctgctcca tgtcatactc     7680
ctggaccggg gctctaataa ctccctgtag ccccgaagag gaaaagttgc caatcaaccc     7740
tttgagtaac tcgctgttgc gataccataa caaggtgtac tgtacaacat caaagagcgc     7800
ctcacagagg gctaaaaagg taactttga caggacgcaa gtgctcgacg cccattatga      7860
ctcagtctta aaggacatca agctagcggc ttccaaggtc agcgcaaggc tcctcacctt     7920
```

| | |
|---|---|
| ggaggaggcg tgccagttga ctccacccca ttctgcaaga tccaagtatg gattcggggc | 7980 |
| caaggaggtc cgcagcttgt ccgggagggc cgttaaccac atcaagtccg tgtggaagga | 8040 |
| cctcctggaa gacccacaaa caccaattcc cacaaccatc atggccaaaa atgaggtgtt | 8100 |
| ctgcgtggac cccgccaagg ggggtaagaa accagctcgc ctcatcgttt accctgacct | 8160 |
| cggcgtccgg gtctgcgaga aaatggccct ctatgacatt acacaaaagc ttcctcaggc | 8220 |
| ggtaatggga gcttcctatg gcttccagta ctcccctgcc caacgggtgg agtatctctt | 8280 |
| gaaagcatgg gcggaaaaga aggaccccat gggttttttcg tatgataccc gatgcttcga | 8340 |
| ctcaaccgtc actgagagag acatcaggac cgaggagtcc atataccagg cctgctccct | 8400 |
| gcccgaggag gcccgcactg ccatacactc gctgactgag agactttacg taggagggcc | 8460 |
| catgttcaac agcaagggtc aaacctgcgg ttacagacgt tgccgcgcca gcggggtgct | 8520 |
| aaccactagc atgggtaaca ccatcacatg ctatgtgaaa gccctagcgg cctgcaaggc | 8580 |
| tgcggggata gttgcgccca atgctggt atgcggcgat gacctagtag tcatctcaga | 8640 |
| aagccagggg actgaggagg acgagcggaa cctgagagcc ttcacggagg ccatgaccag | 8700 |
| gtactctgcc cctcctggtg atccccccag accggaatat gacctggagc taataacatc | 8760 |
| ctgttcctca aatgtgtctg tggcgttggg cccgcggggc cgccgcagat actacctgac | 8820 |
| cagagaccca accactccac tcgcccgggc tgcctgggaa acagttagac actcccctat | 8880 |
| caattcatgg ctgggaaaca tcatccagta tgctccaacc atatgggttc gcatggtcct | 8940 |
| aatgacacac ttcttctcca ttctcatggt ccaagacacc ctggaccaga acctcaactt | 9000 |
| tgagatgtat ggatcagtat actccgtgaa tcctttggac cttccagcca taattgagag | 9060 |
| gttacacggg cttgacgcct tttctatgca cacatactct caccacgaac tgacgcgggt | 9120 |
| ggcttcagcc ctcagaaaac ttgggcgcc accctcagg gtgtggaaga gtcgggctcg | 9180 |
| cgcagtcagg gcgtccctca tctcccgtgg agggaaagcg gccgtttgcg gccgatatct | 9240 |
| cttcaattgg gcggtgaaga ccaagctcaa actcactcca ttgccggagg cgcgcctact | 9300 |
| ggacttatcc agttggttca ccgtcggcgc cggcggggc gacatttttc acagcgtgtc | 9360 |
| gcgcgcccga ccccgctcat tactcttcgg cctactccta cttttcgtag ggtaggcct | 9420 |
| cttcctactc cccgctcggt agagcggcac acactaggta cactccatag ctaactgttc | 9480 |
| cttttttttt tttttttttt tttttttttt tttttttttt ttttcttttt ttttttttc | 9540 |
| cctctttctt cccttctcat cttattctac tttctttctt ggtggctcca tcttagccct | 9600 |
| agtcacggct agctgtgaaa ggtccgtgag ccgcatgact gcagagagtg ccgtaactgg | 9660 |
| tctctctgca gatcatgt | 9678 |

<210> SEQ ID NO 6
<211> LENGTH: 10617
<212> TYPE: DNA
<213> ORGANISM: Artificial
<220> FEATURE:
<223> OTHER INFORMATION: JFH1 variant
<220> FEATURE:
<223> OTHER INFORMATION: JFH1-A/WT-Rluc

<400> SEQUENCE: 6

| | |
|---|---|
| acctgcccct aatagggcg acactccgcc atgaatcact cccctgtgag gaactactgt | 60 |
| cttcacgcag aaagcgccta gccatggcgt tagtatgagt gtcgtacagc ctccaggccc | 120 |
| cccccctcccg ggagagccat agtggtctgc ggaaccggtg agtgcaccgg aattgccggg | 180 |

```
aagactgggt cctttcttgg atacacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacaa atcctaaacc    360
tcaaagaaaa accaaagaa acaccaaccg tcgcccagaa gacgttaagt tcccgggcgg     420
cggccagatc gttggcggag tatacttgtt gccgcgcagg ggcccaggt tgggtgtgcg     480 cacgacaagg aaaacttcgg agcggtccca gccacgtggg agacgccagc ccatccccaa    540
agatcggcgc tccactggca cggcctgggg taaaccaggt cgccctggc ccctatatgg      600 gaatgaggga ctcggctggg caggatggct cctgtccccc cgaggctctc gcccctcctg    660 gggcccact gaccccggc ataggtcgcg caacgtgggt aaagtcatcg acaccctaac     720
gtgtggcttt gccgacctca tggggtacat ccccgtcgta ggcgccccgc ttagtggcgc     780
cgccagagct gtcgcgcacg cgtgagagt cctggaggac ggggttaatt atgcaacagg     840
gaacctacct ggtttcccct tttctatctt cttgctggcc ctgttgtcct gcatcaccgt     900
tccggtctct gctgcccagg tgaagaatac cagtagcagc tacatggtga ccaatgactg    960
ctccaatgac agcatcactt ggcagctcga ggctgcggtt ctccacgtcc ccgggtgcgt    1020
cccgtgcgag agagtgggga atacgtcacg gtgttgggtg ccagtctcgc caaacatggc    1080
tgtgcggcag cccggtgccc tcacgcaggg tctgcggacg cacatcgata tggttgtgat    1140
gtccgccacc ttctgctctg ctctctacgt gggggacctc tgtggcgggg tgatgctcgc    1200
ggcccaggtg ttcatcgtct cgccgcagca ccactggtttt gtgcaggaat gcaattgctc    1260
catctaccct ggcaccatca ctggacaccg catggcatgg acatgatga tgaactggtc     1320 gcccacgacc accatgatcc tggcgtacgt gatgcgcgtc cccgaggtca tcatagacat    1380
cgttagcggg gctcactggg gcgtcatgtt cggcttggcc tacttctcta tgcagggagc    1440
gtgggcgaag gtcattgtca tccttctgct ggccgctggg gtggacgcgg gcaccaccac    1500
cgttggaggc gccgttgcac gtcccaccaa cgtgattgcc ggcgtgttca gccatggccc    1560
tcagcagaac attcagctca ttaacaccag cggcagttgg cacatcaacc gtactgcctt    1620
gaattgcaat gactccttga acaccggctt tctcgcggcc ttgttctaca ccaaccgctt    1680
taactcgtca gggtgtccag ggcgcctgtc cgcctgccgc aacatcgagg cttttccggat   1740 agggtggggc accctacagt acgaggataa tgtcaccaat ccagagggta tgaggccgta    1800
ctgctggcac tacccccaa agccgtgtgg cgtagtcccc acgaggtctg tgtgtggccc     1860
agtgtactgt ttcaccccca gcccggtagt agtgggcacg accgacagac gtggagtgcc    1920
cacctacaca tggggagaga atgagacaga tgtcttccta ctgaacagca cccgaccgcc    1980
gcagggctca tggttcggct gcacgtggat gaactccact ggtttcacca agacttgtgg    2040
cgcgccacct tgccgcacca gagctgactt caacgccagc acggacttgt tgtgccctac    2100
ggattgtttt aggaagcatc ctgatgccac ttatattaag tgtggttctg ggccctggct    2160
cacaccaaag tgcctggtcc actacccta cagactctgg cattacccct gcacagtcaa    2220
ttttaccatc ttcaagataa gaatgtatgt aggggggggtt gagcacaggc tcacggccgc    2280
atgcaacttc actcgtgggg atcgctgcga cttgaggac agggacagga gtcagctgtc    2340
tcctctgttg cactctacca cggaatgggc catcctgccc tgcacctact cagacttacc    2400 cgcttttgtca actggtcttc tccaccttca ccagaacatc gtggacgtac aatacatgta    2460
tggcctctca cctgctatca caaaatacgt cgttcgatgg gagtgggtgg tactcttatt    2520
cctgctctta gcggacgcca gagtctgcgc ctgcttgtgg atgctcatct tgttgggcca    2580
```

```
ggccgaagca gcattggaga agttggtcgt cttgcacgct gcgagtgcgg ctaactgcca    2640
tggcctccta tattttgcca tcttcttcgt ggcagcttgg cacatcaggg gtcgggtggt    2700 cccctttgacc acctattgcc ttactggcct atgcccttc tgcctactgc tcatggcact    2760
gccccggcag gcttatgcct atgacgcacc tgtgcacgga cagataggcg tgggtttgtt    2820
gatattgatc accctcttca cactcacccc ggggtataag accctcctcg gccagtgtct    2880
gtggtggttg tgctatctcc tgaccctggg ggaagccatg attcgggagt gggtaccacc    2940
catgcaggtg cgcggcggcc gcgatggcat cgcgtgggcc gtcactatat tctgcccggg    3000
cgtggtgttt gacattacca aatggctttt ggcgttgctt gggcctgctt acctcttaag    3060
ggccgctttg acccatgtgc cgtacttcgt cagagctcac gctctgataa gggtatgcgc    3120
tttggtgaag cggctcgcgg ggggtaggta tgttcaggtg gcgctgttgg cccttggcag    3180
gtggactggc acctacatct atgaccacct cacacctatg gcggactggg ccgctagcgg    3240
cctgcgcgac ttagcggtcg ccgtggaacc catcatcttc agtccgatgg agaagaaggt    3300
catcgtctgg ggagcggaga cggctgcatg tggggacatt ctacatggac ttcccgtgtc    3360
cgcccgactc ggccaggaga tcctcctcgg cccagctgat ggctacacct ccaagggggtg    3420 gaagctcctt gctcccatca ctgcttatgc ccagcaaaca cgaggcctcc tgggcgccat    3480
agtggtgagt atgacggggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acgaggtccg gtcacgcaga tgtactcgag    3660
tgctgagggg gacttggtag gctggcccag cccccctggg accaagtctt tggagccgtg    3720
caagtgtgga gccgtcgacc tatatctggt cacgcggaac gctgatgtca tcccggctcg    3780
gagacgcggg gataagcggg gagcattgct ctccccgaga cccatttcga ccttgaaggg    3840
gtcctcgggg gggccggtgc tctgccctag gggccacgtc gttgggctct tccgagcagc    3900
tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
gtatgccgcc cagggtaca agtactagt gcttaacccc tcggtagctg ccaccctggg    4140 gtttgggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg gaacggtcct tgatcaagca gagacagccg gggtcagact    4380
aactgtgctg gctacggcca caccccccgg gtcagtgaca acccccccatc ccgatataga    4440 agaggtaggc ctcgggcggg agggtgagat ccccttctat ggggagggcga ttcccctatc    4500 ctgcatcaag ggagggagac acctgatttt ctgccactca aagaaaaagt gtgacgagct    4560
cgcggcggcc cttcggggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag acgctgtctc    4800
acgcagtcag cgccgcgggc gcacaggtag aggaagacag ggcacttata ggtatgtttc    4860
cactggtgaa cgagcctcag gaatgtttga cagtgtagtg ctttgtgagt gctacgacgc    4920
```

```
aggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctcccccgtc   5160
ctgggacgcc atgtggaagt gcctggcccg actcaagcct acgcttgcgg ccccacacc    5220 tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag aggggcagcg   5520
gatagccgag atgttgaagt ccaagatcca aggcttgctg cagcaggcct ctaagcaggc   5580
ccaggacata caacccgcta tgcaggcttc atggcccaaa gtggaacaat tttgggccag   5640
acacatgtgg aacttcatta gcggcatcca atacctcgca ggattgtcaa cactgccagg   5700
gaaccccgcg gtggcttcca tgatggcatt cagtgccgcc ctcaccagtc cgttgtcgac   5760
cagtaccacc atccttctca acatcatggg aggctggtta gcgtcccaga tcgcaccacc   5820
cgcgggggcc accggctttg tcgtcagtgg cctggtgggg gctgccgtgg gcagcatagg   5880
cctgggtaag gtgctggtgg acatcctggc aggatatggt gcgggcattt cgggggccct   5940
cgtcgcattc aagatcatgt ctggcgagaa gccctctatg aagatgtca  tcaatctact   6000 gcctgggatc ctgtctccgg gagccctggt ggtgggggtc atctgcgcgg ccattctgcg   6060
ccgccacgtg gaccgggggg agggcgcggt ccaatggatg aacaggctta ttgcctttgc   6120
ttccagagga aaccacgtcg cccctactca ctacgtgacg gagtcggatg cgtcgcagcg   6180
tgtgacccaa ctacttggct ctcttactat aaccagccta ctcagaagac tccacaattg   6240
gataactgag gactgcccca tcccatgctc cggatcctgg ctccgcgacg tgtgggactg   6300
ggtttgcacc atcttgacag acttcaaaaa ttggctgacc tctaaattgt tccccaagct   6360
gcccggcctc cccttcatct cttgtcaaaa ggggtacaag ggtgtgtggg ccggcactgg   6420
catcatgacc acgcgctgcc cttgcggcgc caacatctct ggcaatgtcc gcctgggctc   6480
tatgaggatc acagggccta aaacctgcat gaacacctgg cagggacct  ttcctatcaa   6540 ttgctacacg gagggccagt gcgcgccgaa accccccacg aactacaaga ccgccatctg   6600
gagggtggcg gcctcggagt acgcggaggt gacgcagcat gggtcgtact cctatgtaac   6660
aggactgacc actgacaatc tgaaaattcc ttgccaacta ccttctccag agttttctc    6720 ctgggtggac ggtgtgcaga tccataggtt tgcacccaca ccaaagccgt ttttccggga   6780
tgaggtctcg ttctgcgttg gcttaattc  ctatgctgtc gggtcccagc ttccctgtga   6840
acctgagccc gacgcagacg tattgaggtc catgctaaca gatccgcccc acatcacggc   6900
ggagactgcg gcgcggcgct tggcacgggg atcacctcca tctgaggcga gctcctcagt   6960
gagccagcta tcagcaccgt cgctgcgggc cacctgcacc acccacagca cacctatga    7020 cgtggacatg gtcgatgcca acctgctcat ggagggcggt gtggctcaga cagagcctga   7080
gtccagggtg cccgttctgg actttctcga gccaatggcc gaggaagaga gcgaccttga   7140
gccctcaata ccatcggagt gcatgctccc caggagcggg tttccacggg ccttaccggc   7200
ttgggcacgc cctgactaca acccgccgct cgtggaatcg tggaggaggc cagattacca   7260
accgccaacc gttgctggtt gtgctctccc ccccccaag  aaggcccga cgcctcccc    7320
```

```
aaggagacgc cggacagtgg gtctgagcga gagcaccata tcagaagccc tccagcaact   7380
ggccatcaag acctttggcc agccccctc  gagcggtgat gcaggctcgt ccacgggggc   7440
gggcgccgcc gaatccggcg gtccgacgtc ccctggtgag ccggcccct  cagagacagg   7500
ttccgcctcc tctatgcccc ccctcgagat ggcttccaag gtgtacgacc cgagcaacg    7560
caaacgcatg atcactgggc ctcagtggtg ggctcgctgc aagcaaatga acgtgctgga   7620
ctccttcatc aactactatg attccgagaa gcacgccgag aacgccgtga ttttctgca    7680
tggtaacgct gcctccagct acctgtggag gcacgtcgtg cctcacatcg agcccgtggc   7740
tagatgcatc atccctgatc tgatcggaat gggtaagtcc ggcaagagcg ggaatggctc   7800
atatcgcctc ctggatcact acaagtacct caccgcttgg ttcgagctgc tgaaccttcc   7860
aaagaaaatc atctttgtgg gccacgactg ggggcttgt  ctggcctttc actactccta   7920
cgagcaccaa gacaagatca aggccatcgt ccatgctgag agtgtcgtgg acgtgatcga   7980
gtcctgggac gagtggcctg acatcgagga ggatatcgcc ctgatcaaga gcgaagaggg   8040
cgagaaaatg gtgcttgaga ataacttctt cgtcgagacc atgctcccaa gcaagatcat   8100
gcggaaactg gagcctgagg agttcgctgc ctacctggag ccattcaagg agaagggcga   8160
ggttagacgg cctacccctct cctggcctcg cgagatccct ctcgttaagg gaggcaagcc   8220
cgacgtcgtc cagattgtcc gcaactacaa cgcctacctt cgggccagcg acgatctgcc   8280
taagatgttc atcgagtccg accctggggtt cttttccaac gctattgtcg agggagctaa   8340
gaagttccct aacaccgagt tcgtgaaggt gaagggcctc cacttcagcc aggaggacgc   8400
tccagatgaa atgggtaagt acatcaagag cttcgtggag cgcgtgctga gaacgagca    8460
gctcgagggg gagcctggag atccggacct ggagtctgat caggtagagc ttcaacctcc   8520
cccccagggg gggggggtag ctcccggttc gggctcgggg tcttggtcta cttgctccga   8580
ggaggacgat accaccgtgt gctgctccat gtcatactcc tggaccgggg ctctaataac   8640
tccctgtagc cccgaagagg aaaagttgcc aatcaaccct ttgagtaact cgctgttgcg   8700
ataccataac aaggtgtact gtacaacatc aaagagcgcc tcacagaggg ctaaaaaggt   8760
aactttttgac aggacgcaag tgctcgacgc ccattatgac tcagtcttaa aggacatcaa   8820
gctagcggct tccaaggtca gcgcaaggct cctcaccttg gaggaggcgt gccagttgac   8880
tccaccccat tctgcaagat ccaagtatgg attcggggcc aaggaggtcc gcagcttgtc   8940
cgggagggcc gttaaccaca tcaagtccgt gtggaaggac ctcctggaag acccacaaac   9000
accaattccc acaaccatca tggccaaaaa tgaggtgttc tgcgtggacc ccgccaaggg   9060
gggtaagaaa ccagctcgcc tcatcgttta ccctgacctc ggcgtccggg tctgcgagaa   9120
aatggccctc tatgacatta cacaaaagct tcctcaggcg gtaatgggag cttcctatgg   9180
cttccagtac tcccctgccc aacgggtgga gtatctcttg aaagcatggg cggaaaagaa   9240
ggaccccatg ggttttttcgt atgatacccg atgcttcgac tcaaccgtca ctgagagaga   9300
catcaggacc gaggagtcca tataccaggc ctgctccctg cccgaggagg cccgcactgc   9360
catacactcg ctgactgaga gactttacgt aggagggccc atgttcaaca gcaagggtca   9420
aacctgcggt tacagacgtt gccgcgccag cggggtgcta accactagca tgggtaacac   9480
catcacatgc tatgtgaaag ccctagcggc ctgcaaggct gcggggatag ttgcgcccac   9540
aatgctggta tgcggcgatg acctagtagt catctcagaa agccagggga ctgaggagga   9600
cgagcggaac ctgagagcct tcacggaggc catgaccagg tactctgccc ctcctggtga   9660
```

```
tccccccaga ccggaatatg acctggagct aataacatcc tgttcctcaa atgtgtctgt    9720
ggcgttgggc ccgcggggcc gccgcagata ctacctgacc agagacccaa ccactccact    9780
cgcccgggct gcctgggaaa cagttagaca ctcccctatc aattcatggc tgggaaacat    9840
catccagtat gctccaacca tatgggttcg catggtccta atgacacact tcttctccat    9900
tctcatggtc caagacaccc tggaccagaa cctcaacttt gagatgtatg gatcagtata   9960
ctccgtgaat cctttggacc ttccagccat aattgagagg ttacgcggc ttgacgcctt   10020
ttctatgcac acatactctc accacgaact gacgcgggtg gcttcagccc tcagaaaact   10080
tggggcgcca cccctcaggg tgtggaagag tcgggctcgc gcagtcaggg cgtccctcat   10140
ctcccgtgga gggaaagcgg ccgtttgcgg ccgatatctc ttcaattggg cggtgaagac   10200
caagctcaaa ctcactccat tgccggaggc gcgcctactg gacttatcca gttggttcac   10260
cgtcggcgcc ggcgggggcg acattttca cagcgtgtcg cgcgcccgac cccgctcatt   10320
actcttcggc ctactcctac ttttcgtagg ggtaggcctc ttcctactcc ccgctcggta   10380
gagcggcaca cactaggtac actccatagc taactgttcc ttttttttt tttttttttt    10440
tttttttttt tttttttttt tttctttttt tttttttttcc ctctttcttc ccttctcatc   10500
ttattctact ttctttcttg gtggctccat cttagcccta gtcacggcta gctgtgaaag   10560
gtccgtgagc cgcatgactg cagagagtgc cgtaactggt ctctctgcag atcatgt     10617
```

```
<210> SEQ ID NO 7
<211> LENGTH: 10617
<212> TYPE: DNA
<213> ORGANISM: Artificial
<220> FEATURE:
<223> OTHER INFORMATION: JFH1 variant
<220> FEATURE:
<223> OTHER INFORMATION: JFH1-B/WT-RLuc

<400> SEQUENCE: 7
```

```
acctgcccct aataggggcg acactccgcc atgaatcact cccctgtgag gaactactgt    60
cttcacgcag aaagcgccta gccatggcgt tagtatgagt gtcgtacagc ctccaggccc   120
cccctcccg ggagagccat agtggtctgc ggaaccggtg agtacaccgg aattgccggg   180
aagactgggt cctttcttgg ataaaccac tctatgcccg gccatttggg cgtgccccg    240
caagactgct agccgagtag cgttgggttg cgaaaggcct tgtggtactg cctgatagg   300
cgcttgcgag tgccccggga ggtctcgtag accgtgcacc atgagcacaa atcctaaacc   360
tcaaagaaa accaaaagaa acaccaaccg tcgcccagaa gacgttaagt tcccgggcgg   420
cggccagatc gctggcggag tatacttgtt gccgcgcagg ggcccaggt tgggtgtgcg   480
cacgacaagg aaaacttcgg agcggtccca gccacgtggg agacgccagc ccatccccaa   540
agatcggcgc tccactggca cggcctgggg aaaaccaggt cgcccctggc ccctatatgg   600
gaatgaggga ctcggctggg caggatggcc cctgtccccc cgaggctctc gcccctcctg   660
gggcccccact gaccccggc ataggtcgcg caacgtgggt aaagtcatcg acaccctaac   720
gtgtggcttt gccgacctca tggggtacat ccccgtcgta ggcgccccgc ttagtggcgc   780
cgccagagct gtcgcgcacg gcgtgagagt cctggaggac gggttaatt atgcaacagg   840
gaacctaccc ggtttcccct tttctatctt cttgctggcc ctgttgtcct gcatcaccgt   900
tccggtctct gctgcccagg tgaagaatac cagtagcagc tacatggtga ccaatgactg   960
ctccaatgac agcatcactt ggcagctcga ggctgcagtt ctccacgtcc ccgggtgcgt  1020
cccgtgcgag agagtgggga atacgtcacg gtgttgggtg ccagtctcgc caaacatggc  1080
```

```
tgtgcggcag cccggtgccc tcacgcaggg tctgcggacg cacatcgata tggttgtgat   1140
gtccgccacc ttctgctctg ctctctacgt gggggacctc tgtggcgggg tgatgctcgc   1200
ggcccaggtg ttcatcgtct cgccgcagta ccactggttt gtgcaggaat gcaattgctc   1260
catctaccct ggcaccatca ctggacaccg catggcatgg acatgatga tgaactggtc    1320
gcccacggcc accatgatcc tggcgtacgt gatgcgcgtc cccgaggtca tcatagacat   1380
cgttagcggg gctcactggg gcgtcatgtt cggcttggcc tacttctcta tgcagggagc   1440
gtgggcgaag gtcattgtca tccttctgct ggccgctggg gtggacgcgg gcaccaccac   1500
cgttgggggc gctgttgcac gttccaccaa cgtgattgcc ggcgtgttca gccatggccc   1560
tcagcagaac attcagctca ttaacaccaa cggcagctgg cacatcaacc gtactgcctt   1620
gaattgcaat gactccttga acaccggctt tctcgcggcc ttgttctaca ccaaccgctt   1680
taactcgtca aggtgtccag ggcgcctgtc cgcctgccgc aacatcgagg ctttccggat   1740
agggtggggc accctacagt acgaggataa tgtcaccaat ccagaggata tgaggccgta   1800
ctgctggcac taccccccaa agccgtgtgg cgtagtcccc gcgaggtctg tgtgtggccc   1860
agtgtactgt ttcactccca gcccggtagt agtgggcacg accgacagac gtggagtgcc   1920
cacctacaca tggggagaga atgagacaga tgtcttccta ctgaacagca cccgaccgcc   1980
acagggctca tggttcggct gcacgtggat gaactccact ggtttcacca agacttgtgg   2040
cgcgccacct tgccgcacca gagctgactt caacgccagc acggacttgt tgtgccctac   2100
ggattgtttt aggaagcatc ctgatgccac ttatattaag tgtggttctg ggccctggct   2160
cacaccaaag tgcctggtcc actaccctta cagactctgg cattacccct gcacagtcaa   2220
ttttaccatc ttcaagataa gaatgtatgt aggggggggtt gagcacaggc tcacggccgc   2280
atgcaacttc actcgtgggg atcgctgcga cttggaggac agggacagga gtcagctgtc   2340
tcctctgttg cactctacca cggaatgggc catcctgccc tgcacctact cagacttacc   2400
cgctttgtca actggtcttc tccaccttca ccagaacatc gtggacgtac aatacatgta   2460
tggcctctca cctgctatca caaaatacgt cgttcgatgg gagtgggtgg tactcttatt   2520
cctgctctta gcggacgcca gagtctgcgc ctgcctgtgg atgctcatct tgttgggcca   2580
ggccgaagca gcattggaga agttggccgt cttgcacgct gcgagtgcgg ctaactgcca   2640
tggcctccta tattttgcca tcttcttcgt ggcagcttgg cacatcaggg gtcgggcggt   2700
cccccttgacc acctattgcc tcactggcct atgggccttc tgcctactgc tcatggcact   2760
gccccggcag gcttatgcct atgacgcacc tgtgcacgga cagataggcg tgggtttgtt   2820
gatattgatc ccctcttca cactcacccc ggggtataag accctcctcg gccagtgtct   2880
gtggtggttg tgctatctcc tgaccctggg ggaagccatg attcgggagt gggtaccacc   2940
catgcaggtg cgcggcggcc gcgatggcat cgcgtgggcc gtcactatat tctgcccggg   3000
tgtggtgttt gacattacca aatggcttt ggcgttgctt gggcctgctt acctcttaag    3060
ggccgctttg acacatgtgc cgtacttcgt cagagctcac gctctgataa gggtatgcgc   3120
tttggtgaag cagctcgcgg ggggtaggta tgttcaggtg cgctattgg cccttggcag    3180
gtggactggc acctacatct atgaccacct cacacctatg tcggactggg ccgctagcgg   3240
cctgcgcgac ttagcggtcg ccgtggaacc catcatcttc agtccgatgg agaagaaggt   3300
catcgtctgg ggagcggaga cggctgcatg tgggggacatt ctacatggac ttcccgtgtc   3360
cgcccgactc ggccaggaga tcctcctcgg cccagctgat ggctacacct ccaaggggtg   3420
```

```
gaagctcctt gctcccatca ctgcttatgc ccagcaaaca cgaggcctcc tgggcgccat    3480
agtggtgagt atgacgggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag gctggcccag ccccctggg accaagtctt tggagccgtg    3720
caagtgtgga gccgtcgacc tatatctggt cacgcggaac gctgatgtta tcccggctcg    3780
gagacgcggg gacaagcggg gagcattgct ctccccgaga cccatttcga ccttgaaggg    3840
gtcctcgggg gggccggtgc tctgccctag gggccacgtc gttgggctct tccgagcagc    3900
tgtgtgctct cggggcgtgg ccaaatccat cgatttcatc cccgttgaga cactcgacgt    3960
tgttacaagg tctcccacct tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca agtactagt gcttaacccc tcggtagctg ccaccctggg    4140
gtttggggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg gaacggtcct tgatcaagca gagacagccg gggtcagact    4380
aactgtgctg gctacggcca cacccccgg gtcagtgaca acccccatc ccgatataga    4440 agaggtaggc ctcgggcggg agggtgagat ccccttctat gggagggcga ttcccctatc    4500
ctgcatcaag ggagggagac acctgatttt ctgccactca aagaaaagt gtgacgagct    4560 cgcggcggcc cttcggggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag cgctgtctc    4800 acgcagtcag cgccgcgggc gcacaggtag aggaagacag ggcacttata ggtatgtttc    4860
cactggtgaa cgagcctcag gaatgtttga cagtgtagtg cttttgtgagt gctacgacgc    4920 aggggctgcg tggtacgatc tcacaccagc ggagaccacc gtcaggctta gagcgtattt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtaccta gtagcctacc aagctacggt gtgcgccaga gccaaggccc ctcccccgtc    5160
ctgggacgcc atgtggaagt gcctggcccg actcaagcct acgcttgcgg ccccacacc    5220 tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctggcagccg tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcggct ctcatcgaag aggggcagcg    5520
gatagccgag atgttgaagt ccaagatcca aggcttgctg cagcaggcct ctaagcaggc    5580
ccaggacata caaccgcta tgcaggcttc atggcccaaa gtggaacaat tttgggccag    5640
acacatgtgg aacttcatta gcggcatcca atacctcgca ggattgtcaa cactgccagg    5700
gaaccccgcg gtgcttcca tgatggcatt cagtgccgcc ctcaccagtc cgttgtcgac    5760
cagtaccacc atccttctca acatcatggg aggctggtta gcgtcccaga tcgcaccacc    5820
```

-continued

```
cgcgggggcc accggctttg tcgtcagtgg cctggtgggg gctgccgtgg gcagcatagg    5880
cctgggtaag gtgctggtgg acatcctggc aggatatggt gcgggcattt cgggggcct    5940 cgtcgcattc aagatcatgt ctggcgagaa gccctctatg aagatgtca tcaatctact    6000 gcctgggatc ctgtctccgg gagccctggt ggtgggggtc atctgcgcgg ccattctgcg    6060
ccgccacgtg ggaccggggg agggcgcggt ccaatggatg aacaggctta ttgcctttgc    6120
ttccagagga accacgtcg cccctactca ctacgtgacg gagtcggatg cgtcgcagcg    6180
tgtgacccaa ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360
gcccggcctc cccttcatct cttgtcaaaa ggggtacaag ggtgtgtggg ccggcactgg    6420
catcatgacc acgcgctgcc cttgcggcgc caacatctct ggcaatgtcc gcctgggctc    6480
tatgaggatc acagggccta aaacctgcat gaacacctgg caggggacct ttcctatcaa    6540
ttgctacacg gagggccagt gcgcgccgaa acccccacg aactacaaga ccgccatctg    6600
gagggtggcg gcctcggagt acgcggaggt gacgcagcat gggtcgtact cctatgtaac    6660
aggactgacc actgacaatc tgaaaattcc ttgccaacta ccttctccag agttttctc    6720 ctgggtggac ggtgtgcaga tccataggtt tgcacccaca ccaaagccgt ttttccggga    6780
tgaggtctcg ttctgcgttg gcttaattc ctatgctgtc gggtcccagc ttccctgtga    6840
acctgagccc gacgcagacg tattgaggtc catgctaaca gatccgcccc acatcacggc    6900
ggagactgcg gcgcggcgct ggcacggggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260 accgccacc gttgctggtt gtgctctccc cccccaag aaggcccga cgcctcccc      7320 aaggagacgc cggacagtgg gtctgagcga gagcaccata tcagaagccc tccagcaact    7380
ggccatcaag acctttggcc agccccctc gagcggtgat gcaggctcgt ccacgggggc    7440
gggcgccgcc gaatccggcg gtccgacgtc ccctggtgag ccggcccct cagagacagg    7500 ttccgcctcc tctatgcccc cctcgagat ggcttccaag gtgtacgacc ccgagcaacg    7560
caaacgcatg atcactgggc tcagtggtg ggctcgctgc aagcaaatga acgtgctgga    7620
ctccttcatc aactactatg attccgagaa gcacgccgag aacgccgtga tttttctgca    7680
tggtaacgct gcctccagct acctgtggag gcacgtcgtg cctcacatcg agcccgtggc    7740
tagatgcatc atccctgatc tgatcggaat gggtaagtcc ggcaagagcg ggaatggctc    7800
atatcgcctc ctggatcact acaagtacct caccgcttgg ttcgagctgc tgaaccttcc    7860
aaagaaaatc atctttgtgg ccacgactg gggggcttgt ctggcctttc actactccta    7920
cgagcaccaa gacaagatca aggccatcgt ccatgctgag agtgtcgtgg acgtgatcga    7980
gtcctgggac gagtggcctg acatcgagga ggatatcgcc ctgatcaaga gcgaagaggg    8040
cgagaaaatg gtgcttgaga ataacttctt cgtcgagacc atgctcccaa gcaagatcat    8100
gcggaaactg gagcctgagg agttcgctgc ctacctggag ccattcaagg agaagggcga    8160
```

```
ggttagacgg cctaccctct cctggcctcg cgagatccct ctcgttaagg gaggcaagcc   8220
cgacgtcgtc cagattgtcc gcaactacaa cgcctacctt cgggccagcg acgatctgcc   8280
taagatgttc atcgagtccg accctgggtt cttttccaac gctattgtcg agggagctaa   8340
gaagttccct aacaccgagt tcgtgaaggt aagggcctc cacttcagcc aggaggacgc    8400
tccagatgaa atgggtaagt acatcaagag cttcgtggag cgcgtgctga agaacgagca   8460
gctcgagggg gagcctggag atccggacct ggagtctgat caggtagagc ttcaacctcc   8520
cccccagggg gggggggtag ctcccggttc gggctcgggg tcttggtcta cttgctccga   8580
ggaggacgat accaccgtgt gctgctccat gtcatactcc tggaccgggg ctctaataac   8640
tccctgtagc cccgaagagg aaaagttgcc aatcaaccct ttgagtaact cgctgttgcg   8700
ataccataac aaggtgtact gtacaacatc aaagagcgcc tcacagaggg ctaaaaaggt   8760
aacttttgac aggacgcaag tgctcgacgc ccattatgac tcagtcttaa aggacatcaa   8820
gctagcggct tccaaggtca gcgcaaggct cctcaccttg gaggaggcgt gccagttgac   8880
tccaccccat tctgcaagat ccaagtatgg attcggggcc aaggaggtcc gcagcttgtc   8940
cgggagggcc gttaaccaca tcaagtccgt gtggaaggac ctcctggaag acccacaaac   9000
accaattccc acaaccatca tggccaaaaa tgaggtgttc tgcgtggacc ccgccaaggg   9060
gggtaagaaa ccagctcgcc tcatcgttta ccctgacctc ggcgtccggg tctgcgagaa   9120
aatggccctc tatgacatta cacaaaagct tcctcaggcg gtaatgggag cttcctatgg   9180
cttccagtac tcccctgccc aacgggtgga gtatctcttg aaagcatggg cggaaaagaa   9240
ggaccccatg ggttttttcgt atgatacccg atgcttcgac tcaaccgtca ctgagagaga   9300
catcaggacc gaggagtcca tataccaggc ctgctccctg cccgaggagg cccgcactgc   9360
catacactcg ctgactgaga gactttacgt aggagggccc atgttcaaca gcaagggtca   9420
aacctgcggt tacagacgtt gccgcgccag cggggtgcta accactagca tgggtaacac   9480
catcacatgc tatgtgaaag ccctagcggc ctgcaaggct gcggggatag ttgcgcccac   9540
aatgctggta tgcggcgatg acctagtagt catctcagaa gccaggggga ctgaggagga   9600
cgagcggaac ctgagagcct tcacggaggc catgaccagg tactctgccc tcctggtgaa   9660 tcccccaga ccggaatatg acctggagct aataacatcc tgttcctcaa atgtgtctgt    9720
ggcgttgggc ccgcggggcc gccgcagata ctacctgacc agagacccaa ccactccact   9780
cgcccgggct gcctgggaaa cagttagaca ctcccctatc aattcatggc tgggaaacat   9840
catccagtat gctccaacca tatgggttcg catggtccta atgacacact tcttctccat   9900
tctcatggtc caagacaccc tggaccagaa cctcaacttt gagatgtatg gatcagtata   9960
ctccgtgaat cctttggacc ttccagccat aattgagagg ttacgcggc ttgacgcctt   10020 ttctatgcac acatactctc accacgaact gacgcgggtg gcttcagccc tcagaaaact   10080
tggggcgcca cccctcaggg tgtggaagag tcgggctcgc gcagtcaggg cgtccctcat   10140
ctcccgtgga gggaaagcgg ccgtttgcgg ccgatatctc ttcaattggg cggtgaagac   10200
caagctcaaa ctcactccat tgccggaggc gcgcctactg gacttatcca gttggttcac   10260
cgtcggcgcc ggcgggggcg acattttcca cagcgtgtcg cgcgcccgac cccgctcatt   10320
actcttcggc ctactcctac ttttcgtagg ggtaggcctc ttcctactcc ccgctcggta   10380
gagcggcaca cactaggtac actccatagc taactgttcc ttttttttt ttttttttt    10440 tttttttttt tttttttttt tttctttttt tttttttcc ctctttcttc ccttctcatc   10500
ttattctact ttctttcttg gtggctccat cttagcccta gtcacggcta gctgtgaaag   10560
```

-continued gtccgtgagc cgcatgactg cagagagtgc cgtaactggt ctctctgcag atcatgt    10617

<210> SEQ ID NO 8
<211> LENGTH: 10617
<212> TYPE: DNA
<213> ORGANISM: Artificial
<220> FEATURE:
<223> OTHER INFORMATION: JFH1 variant
<220> FEATURE:
<223> OTHER INFORMATION: JFH1wt-Rluc

<400> SEQUENCE: 8

| | | | | | |
|---|---|---|---|---|---|
| acctgcccct | aatagggcg | acactccgcc | atgaatcact | ccctgtgag | gaactactgt | 60 |
| cttcacgcag | aaagcgccta | gccatggcgt | tagtatgagt | gtcgtacagc | ctccaggccc | 120 |
| cccctcccg | ggagagccat | agtggtctgc | ggaaccggtg | agtacaccgg | aattgccggg | 180 |
| aagactgggt | cctttcttgg | ataaacccac | tctatgcccg | gccatttggg | cgtgcccccg | 240 |
| caagactgct | agccgagtag | cgttgggttg | cgaaaggcct | tgtggtactg | cctgataggg | 300 |
| cgcttgcgag | tgccccggga | ggtctcgtag | accgtgcacc | atgagcacaa | atcctaaacc | 360 |
| tcaaagaaaa | accaaaagaa | acaccaaccg | tcgcccagaa | gacgttaagt | tcccgggcgg | 420 |
| cggccagatc | gttggcggag | tatacttgtt | gccgcgcagg | ggccccaggt | tgggtgtgcg | 480 |
| cacgacaagg | aaaacttcgg | agcggtccca | gccacgtggg | agacgccagc | ccatccccaa | 540 |
| agatcggcgc | tccactggca | aggcctgggg | aaaaccaggt | cgcccctggc | cctatatgg | 600 |
| gaatgaggga | ctcggctggg | caggatggct | cctgtccccc | cgaggctctc | gcccctcctg | 660 |
| gggcccccact | gacccccggc | ataggtcgcg | caacgtgggt | aaagtcatcg | acaccctaac | 720 |
| gtgtggcttt | gccgacctca | tggggtacat | cccgtcgta | ggcgccccgc | ttagtggcgc | 780 |
| cgccagagct | gtcgcgcacg | gcgtgagagt | cctggaggac | ggggttaatt | atgcaacagg | 840 |
| gaacctaccc | ggtttcccct | tttctatctt | cttgctggcc | ctgttgtcct | gcatcaccgt | 900 |
| tccggtctct | gctgcccagg | tgaagaatac | cagtagcagc | tacatggtga | ccaatgactg | 960 |
| ctccaatgac | agcatcactt | ggcagctcga | ggctgcggtt | ctccacgtcc | ccgggtgcgt | 1020 |
| cccgtgcgag | agagtgggga | atacgtcacg | gtgttgggtg | ccagtctcgc | caaacatggc | 1080 |
| tgtgcggcag | cccggtgccc | tcacgcaggg | tctgcggacg | cacatcgata | tggttgtgat | 1140 |
| gtccgccacc | ttctgctctg | ctctctacgt | ggggacctc | tgtggcgggg | tgatgctcgc | 1200 |
| ggcccaggtg | ttcatcgtct | cgccgcagta | ccactggttt | gtgcaagaat | gcaattgctc | 1260 |
| catctaccct | ggcaccatca | ctggacaccg | catggcatgg | acatgatga | tgaactggtc | 1320 |
| gcccacggcc | accatgatcc | tggcgtacgt | gatgcgcgtc | cccgaggtca | tcatagacat | 1380 |
| cgttagcggg | gctcactggg | gcgtcatgtt | cggcttggcc | tacttctcta | tgcagggagc | 1440 |
| gtgggcgaag | gtcattgtca | tccttctgct | ggccgctggg | gtggacgcgg | gcaccaccac | 1500 |
| cgttggaggc | gctgttgcac | gttccaccaa | cgtgattgcc | ggcgtgttca | gccatggccc | 1560 |
| tcagcagaac | attcagctca | ttaacaccaa | cggcagttgg | cacatcaacc | gtactgcctt | 1620 |
| gaattgcaat | gactccttga | acaccggctt | tctcgcggcc | ttgttctaca | ccaaccgctt | 1680 |
| taactcgtca | gggtgtccag | ggcgcctgtc | cgcctgccgc | aacatcgagg | ctttccggat | 1740 |
| agggtggggc | accctacagt | acgaggataa | tgtcaccaat | ccagaggata | tgaggccgta | 1800 |
| ctgctggcac | taccccccaa | agccgtgtgg | cgtagtcccc | gcgaggtctg | tgtgtggccc | 1860 |
| agtgtactgt | ttcaccccca | gcccggtagt | agtgggcacg | accgacagac | gtggagtgcc | 1920 |

```
cacctacaca tggggagaga atgagacaga tgtcttccta ctgaacagca cccgaccgcc   1980
gcagggctca tggttcggct gcacgtggat gaactccact ggtttcacca agacttgtgg   2040
cgcgccacct tgccgcacca gagctgactt caacgccagc acggacttgt tgtgccctac   2100
ggattgtttt aggaagcatc ctgatgccac ttatattaag tgtggttctg ggccctggct   2160
cacaccaaag tgcctggtcc actacccctta cagactctgg cattacccct gcacagtcaa   2220
ttttaccatc ttcaagataa gaatgtatgt agggggggtt gagcacaggc tcacggccgc   2280
atgcaacttc actcgtgggg atcgctgcga cttggaggac agggacagga gtcagctgtc   2340
tcctctgttg cactctacca cggaatgggc catcctgccc tgcacctact cagacttacc   2400
cgctttgtca actggtcttc tccaccttca ccagaacatc gtggacgtac aatacatgta   2460
tggcctctca cctgctatca caaaatacgt cgttcgatgg gagtgggtgg tactcttatt   2520
cctgctctta gcggacgcca gagtctgcgc ctgcttgtgg atgctcatct tgtttgggcca   2580 ggccgaagca gcattggaga agttggtcgt cttgcacgct gcgagtgcgg ctaactgcca   2640
tggcctccta tattttgcca tcttcttcgt ggcagcttgg cacatcaggg gtcgggtggt   2700 cccccttgacc acctattgcc tcactggcct atggcccttc tgcctactgc tcatggcact   2760
gccccggcag gcttatgcct atgacgcacc tgtgcacgga cagataggcg tgggtttgtt   2820
gatattgatc accctcttca cactcacccc ggggtataag accctcctcg gccagtgtct   2880
gtggtggttg tgctatctcc tgaccctggg ggaagccatg attcaggagt gggtaccacc   2940
catgcaggtg cgcggcggcc gcgatggcat cgcgtgggcc gtcactatat tctgcccggg   3000
tgtggtgttt gacattacca aatggctttt ggcgttgctt gggcctgctt acctcttaag   3060
ggccgctttg acacatgtgc cgtacttcgt cagagctcac gctctgataa gggtatgcgc   3120
tttggtgaag cagctcgcgg gggtaggta tgttcaggtg gcgctattgg ccccttggcag   3180 gtggactggc acctacatct atgaccacct cacacctatg tcggactggg ccgctagcgg   3240
cctgcgcgac ttagcggtcg ccgtggaacc atcatcttc agtccgatgg agaagaaggt   3300
catcgtctgg ggagcggaga cggctgcatg tggggacatt ctacatggac ttcccgtgtc   3360
cgcccgactc ggccaggaga tcctcctcgg cccagctgat ggctacacct caagggtg   3420 gaagctcctt gctcccatca ctgcttatgc ccagcaaaca cgaggcctcc tgggcgccat   3480
agtggtgagt atgacggggc gtgacaggac agaacaggcc ggggaagtcc aaatcctgtc   3540
cacagtctct cagtccttcc tcggaacaac catctcgggg gttttgtgga ctgtttacca   3600
cggagctggc aacaagactc tagccggctt acggggtccg gtcacgcaga tgtactcgag   3660
tgctgagggg gacttggtag ctggcccag ccccctggg accaagtctt tggagccgtg   3720
caagtgtgga gccgtcgacc tatatctggt cacgcggaac gctgatgtca tcccggctcg   3780
gagacgcggg gacaagcggg gagcattgct ctccccgaga cccatttcga ccttgaaggg   3840
gtcctcgggg gggccggtgc tctgccctag ggccacgtc gttgggctct tccgagcagc   3900
tgtgtgctct cggggcgtgg ccaaatccat cgatttcatc cccgttgaga cactcgacgt   3960
tgttacaagg tctcccactt tcagtgacaa cagcacgcca ccggctgtgc cccagaccta   4020
tcaggtcggg tacttgcatg ctccaactgg cagtggaaag agcaccaagg tccctgtcgc   4080
gtatgccgcc cagggtaca agtactagt gcttaacccc tcggtagctg ccaccctggg   4140
gtttggggcg tacctatcca aggcacatgg catcaatccc aacattagga ctggagtcag   4200
gaccgtgatg accggggagg ccatcacgta ctccacatat ggcaaatttc tcgccgatgg   4260
gggctgcgct agcggcgcct atgacatcat catatgcgat gaatgccacg ctgtggatgc   4320
```

```
tacctccatt ctcggcatcg aacggtcct tgatcaagca gagacagccg gggtcagact    4380
aactgtgctg gctacggcca cacccccgg gtcagtgaca accccccatc ccgatataga    4440
agaggtaggc ctcgggcggg agggtgagat ccccttctat gggagggcga ttcccctatc    4500
ctgcatcaag ggagggagac acctgatttt ctgccactca agaaaaagt gtgacgagct    4560
cgcggcggcc cttcggggca tgggcttgaa tgccgtggca tactatagag ggttggacgt    4620
ctccataata ccagctcagg gagatgtggt ggtcgtcgcc accgacgccc tcatgacggg    4680
gtacactgga gactttgact ccgtgatcga ctgcaatgta gcggtcaccc aagctgtcga    4740
cttcagcctg gaccccacct tcactataac cacacagact gtcccacaag acgctgtctc    4800
acgcagtcag cgccgcgggc gcacaggtag aggaagacag ggcacttata ggtatgtttc    4860
cactggtgaa cgagcctcag gaatgtttga cagtgtagtg cttgtgagt gctacgacgc    4920
aggggctgcg tggtacgatc tcacaccagc ggagaccacc gtcaggctta gagcgtattt    4980
caacacgccc ggcctacccg tgtgtcaaga ccatcttgaa ttttgggagg cagttttcac    5040
cggcctcaca cacatagacg cccacttcct ctcccaaaca aagcaagcgg gggagaactt    5100
cgcgtaccta gtagcctacc aagctacggt gtgcgccaga gccaaggccc ctcccccgtc    5160
ctgggacgcc atgtggaagt gcctggcccg actcaagcct acgcttgcgg ccccacacc    5220
tctcctgtac cgtttgggcc ctattaccaa tgaggtcacc ctcacacacc ctgggacgaa    5280
gtacatcgcc acatgcatgc aagctgacct tgaggtcatg accagcacgt gggtcctagc    5340
tggaggagtc ctggcagccg tcgccgcata ttgcctggcg actggatgcg tttccatcat    5400
cggccgcttg cacgtcaacc agcgagtcgt cgttgcgccg gataaggagg tcctgtatga    5460
ggcttttgat gagatggagg aatgcgcctc tagggcggct ctcatcgaag aggggcagcg    5520
gatagccgag atgttgaagt ccaagatcca aggcttgctg cagcaggcct ctaagcaggc    5580
ccaggacata caacccgcta tgcaggcttc atggcccaaa gtggaacaat tttgggccag    5640
acacatgtgg aacttcatta gcggcatcca ataccctcgca ggattgtcaa cactgccagg    5700
gaacccccgcg gtggcttcca tgatggcatt cagtgccgcc ctcaccagtc cgttgtcgac    5760
cagtaccacc atccttctca acatcatggg aggctggtta gcgtcccaga tcgcaccacc    5820
cgcgggggcc accggcttg tcgtcagtgg cctggtgggg gctgccgtgg cagcatagg    5880
cctgggtaag gtgctggtgg acatcctggc aggatatggt gcgggcattt cgggggccct    5940
cgtcgcattc aagatcatgt ctggcgagaa gccctctatg aagatgtca tcaatctact    6000
gcctgggatc ctgtctccgg gagccctggt ggtgggggtc atctgcgcgg ccattctgcg    6060
ccgccacgtg ggaccggggg agggcgcggt ccaatggatg aacaggctta ttgcctttgc    6120
ttccagagga aaccacgtcg cccctactca ctacgtgacg gagtcggatg cgtcgcagcg    6180
tgtgacccaa ctacttggct ctcttactat aaccagccta ctcagaagac tccacaattg    6240
gataactgag gactgcccca tcccatgctc cggatcctgg ctccgcgacg tgtgggactg    6300
ggtttgcacc atcttgacag acttcaaaaa ttggctgacc tctaaattgt tccccaagct    6360
gcccggcctc cccttcatct cttgtcaaaa ggggtacaag ggtgtgtggg ccggcactgg    6420
catcatgacc acgcgctgcc cttgcggcgc caacatctct ggcaatgtcc gcctgggctc    6480
tatgaggatc acagggccta aaacctgcat gaacacctgg caggggacct ttcctatcaa    6540
ttgctacacg gagggccagt gcgcgccgaa accccccacg aactacaaga ccgccatctg    6600
gagggtggcg gcctcggagt acgcggaggt gacgcagcat gggtcgtact cctatgtaac    6660
```

```
aggactgacc actgacaatc tgaaaattcc ttgccaacta ccttctccag agtttttctc    6720
ctgggtggac ggtgtgcaga tccataggtt tgcacccaca ccaaagccgt ttttccggga    6780
tgaggtctcg ttctgcgttg ggcttaattc ctatgctgtc gggtcccagc ttccctgtga    6840
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260 accgccacc  gttgctggtt gtgctctccc ccccccaag  aaggcccga  cgcctccccc    7320 aaggagacgc cggacagtgg gtctgagcga gagcaccata tcagaagccc tccagcaact    7380
ggccatcaag acctttggcc agccccctc  gagcggtgat gcaggctcgt ccacggggc    7440 gggcgccgcc gaatccggcg gtccgacgtc ccctggtgag ccggcccct  cagagacagg    7500 ttccgcctcc tctatgcccc ccctcgagat ggcttccaag gtgtacgacc ccgagcaacg    7560
caaacgcatg atcactgggc tcagtggtg  ggctcgctgc aagcaaatga acgtgctgga    7620
ctccttcatc aactactatg attccgagaa gcacgccgag aacgccgtga ttttctgca    7680 tggtaacgct gcctccagct acctgtggag gcacgtcgtg cctcacatcg agcccgtggc    7740
tagatgcatc atccctgatc tgatcggaat gggtaagtcc ggcaagagcg ggaatggctc    7800
atatcgcctc ctggatcact acaagtacct caccgcttgg ttcgagctgc tgaaccttcc    7860
aaagaaaatc atctttgtgg gccacgactg gggggcttgt ctggcctttc actactccta    7920
cgagcaccaa gacaagatca aggccatcgt ccatgctgag agtgtcgtgg acgtgatcga    7980
gtcctgggac gagtggcctg acatcgagga ggatatcgcc ctgatcaaga gcgaagaggg    8040
cgagaaaatg gtgcttgaga ataacttctt cgtcgagacc atgctcccaa gcaagatcat    8100
gcggaaactg gagcctgagg agttcgctgc ctacctggag ccattcaagg agaagggcga    8160
ggttagacgg cctaccctct cctggcctcg cgagatccct ctcgttaagg gaggcaagcc    8220
cgacgtcgtc cagattgtcc gcaactacaa cgcctacctt cgggccagcg acgatctgcc    8280
taagatgttc atcgagtccg accctggggtt cttttccaac gctattgtcg agggagctaa    8340
gaagttccct aacaccgagt tcgtgaaggt gaagggcctc cacttcagcc aggaggacgc    8400
tccagatgaa atgggtaagt acatcaagag cttcgtggag cgcgtgctga agaacgagca    8460
gctcgagggg gagcctggag atccggacct ggagtctgat caggtagagc ttcaacctcc    8520 ccccagggg  gggggggtag ctcccggttc gggctcgggg tcttggtcta cttgctccga    8580
ggaggacgat accaccgtgt gctgctccat gtcatactcc tggaccgggg ctctaataac    8640
tccctgtagc cccgaagagg aaaagttgcc aatcaaccct ttgagtaact cgctgttgcg    8700
ataccataac aaggtgtact gtacaacatc aaagagcgcc tcacagaggg ctaaaaaggt    8760
aacttttgac aggacgcaag tgctcgacgc ccattatgac tcagtcttaa aggacatcaa    8820
gctagcggct tccaaggtca gcgcaaggct cctcaccttg gaggaggcgt gccagttgac    8880
tccaccccat tctgcaagat ccaagtatgg attcggggcc aaggaggtcc gcagcttgtc    8940 cgggagggc  gttaaccaca tcaagtccgt gtggaaggac ctcctggaag acccacaaac    9000
accaattccc acaaccatca tggccaaaaa tgaggtgttc tgcgtggacc ccgccaaggg    9060
```

-continued

| | |
|---|---|
| gggtaagaaa ccagctcgcc tcatcgttta ccctgacctc ggcgtccggg tctgcgagaa | 9120 |
| aatggccctc tatgacatta cacaaaagct tcctcaggcg gtaatgggag cttcctatgg | 9180 |
| cttccagtac tcccctgccc aacgggtgga gtatctcttg aaagcatggg cggaaaagaa | 9240 |
| ggaccccatg ggttttttcgt atgatacccg atgcttcgac tcaaccgtca ctgagagaga | 9300 |
| catcaggacc gaggagtcca tataccaggc ctgctccctg cccgaggagg cccgcactgc | 9360 |
| catacactcg ctgactgaga gactttacgt aggagggccc atgttcaaca gcaagggtca | 9420 |
| aacctgcggt tacagacgtt gccgcgccag cggggtgcta accactagca tgggtaacac | 9480 |
| catcacatgc tatgtgaaag ccctagcggc ctgcaaggct gcgggatag ttgcgcccac | 9540 |
| aatgctggta tgcggcgatg acctagtagt catctcagaa agccagggga ctgaggagga | 9600 |
| cgagcggaac ctgagagcct tcacggaggc catgaccagg tactctgccc tcctggtga | 9660 |
| tccccccaga ccggaatatg acctggagct aataacatcc tgttcctcaa atgtgtctgt | 9720 |
| ggcgttgggc ccgcggggcc gccgcagata ctacctgacc agagacccaa ccactccact | 9780 |
| cgcccgggct gcctgggaaa cagttagaca ctcccctatc aattcatggc tgggaaacat | 9840 |
| catccagtat gctccaacca tatgggttcg catggtccta atgacacact tcttctccat | 9900 |
| tctcatggtc caagacaccc tggaccagaa cctcaacttt gagatgtatg gatcagtata | 9960 |
| ctccgtgaat cctttggacc ttccagccat aattgagagg ttacgggc ttgacgcctt | 10020 |
| ttctatgcac acatactctc accacgaact gacgcgggtg gcttcagccc tcagaaaact | 10080 |
| tggggcgcca cccctcaggg tgtggaagag tcgggctcgc gcagtcaggg cgtccctcat | 10140 |
| ctcccgtgga gggaaagcgg ccgtttgcgg ccgatatctc ttcaattggg cggtgaagac | 10200 |
| caagctcaaa ctcactccat tgccggaggc gcgcctactg gacttatcca gttggttcac | 10260 |
| cgtcggcgcc ggcggggggcg acattttca cagcgtgtcg cgcgcccgac cccgctcatt | 10320 |
| actcttcggc ctactcctac ttttcgtagg ggtaggcctc ttcctactcc ccgctcggta | 10380 |
| gagcggcaca cactaggtac actccatagc taactgttcc tttttttttt tttttttttt | 10440 |
| tttttttttt tttttttttt tttctttttt ttttttttcc ctctttcttc ccttctcatc | 10500 |
| ttattctact ttctttcttg gtggctccat cttagcccta gtcacggcta gctgtgaaag | 10560 |
| gtccgtgagc cgcatgactg cagagagtgc cgtaactggt ctctctgcag atcatgt | 10617 |

<210> SEQ ID NO 9
<211> LENGTH: 933
<212> TYPE: DNA
<213> ORGANISM: Renilla reniformis
<220> FEATURE:
<223> OTHER INFORMATION: Renilla Luciferase

<400> SEQUENCE: 9

| | |
|---|---|
| atggcttcca aggtgtacga ccccgagcaa cgcaaacgca tgatcactgg gcctcagtgg | 60 |
| tgggctcgct gcaagcaaat gaacgtgctg gactccttca tcaactacta tgattccgag | 120 |
| aagcacgccg agaacgccgt gatttttctg catggtaacg ctgcctccag ctacctgtgg | 180 |
| aggcacgtcg tgcctcacat cgagcccgtg gctagatgca tcatccctga tctgatcgga | 240 |
| atgggtaagt ccggcaagag cgggaatggc tcatatcgcc tcctggatca ctacaagtac | 300 |
| ctcaccgctt ggttcgagct gctgaacctt ccaaagaaaa tcatctttgt gggccacgac | 360 |
| tggggggctt gtctggcctt tcactactcc tacgagcaca agacaagat caaggccatc | 420 |
| gtccatgctg agagtgtcgt ggacgtgatc gagtcctggg acgagtggcc tgacatcgag | 480 |

```
gaggatatcg ccctgatcaa gagcgaagag ggcgagaaaa tggtgcttga gaataacttc      540
ttcgtcgaga ccatgctccc aagcaagatc atgcggaaac tggagcctga ggagttcgct      600
gcctacctgg agccattcaa ggagaagggc gaggttagac ggcctaccct ctcctggcct      660
cgcgagatcc ctctcgttaa gggaggcaag cccgacgtcg tccagattgt ccgcaactac      720
aacgcctacc ttcgggccag cgacgatctg cctaagatgt tcatcgagtc cgaccctggg      780 ttctttttcca acgctattgt cgagggagct aagaagttcc ctaacaccga gttcgtgaag      840
gtgaagggcc tccacttcag ccaggaggac gctccagatg aaatgggtaa gtacatcaag      900
agcttcgtgg agcgcgtgct gaagaacgag cag                                    933
```

```
<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
ctttgactcc gtgatcgacc                                                    20

<210> SEQ ID NO 11
<211> LENGTH: 19
<212> TYPE: DNA
<213> ORGANISM: Artificial
<220> FEATURE:
<223> OTHER INFORMATION: primer

<400> SEQUENCE: 11
ccctgtcttc ctctacctg                                                     19

<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
tggcacccag cacaatgaa                                                     19

<210> SEQ ID NO 13
<211> LENGTH: 25
<212> TYPE: DNA
<213> ORGANISM: Artificial
<220> FEATURE:
<223> OTHER INFORMATION: primer

<400> SEQUENCE: 13
ctaagtcata gtccgcctag aagca                                              25

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
ctcgagatgg cttccaaggt gtacgacccc                                         30

<210> SEQ ID NO 15
<211> LENGTH: 30
```

```
<212> TYPE: DNA
<213> ORGANISM: Artificial
<220> FEATURE:
<223> OTHER INFORMATION: primer

<400> SEQUENCE: 15
ctcgagctgc tcgttcttca gcacgcgctc                                    30

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
ggaacagtta gctatggagt gtacc                                         25

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
tgtcttcacg cagaaagcgc ctag                                          24

<210> SEQ ID NO 18
<211> LENGTH: 25
<212> TYPE: DNA
<213> ORGANISM: Artificial
<220> FEATURE:
<223> OTHER INFORMATION: primer

<400> SEQUENCE: 18
ctgagctggt attatggaga cgtcc                                         25
```